US009951029B2

(12) United States Patent
Baska et al.

(10) Patent No.: US 9,951,029 B2
(45) Date of Patent: Apr. 24, 2018

(54) STYRYL QUINAZOLINE DERIVATIVES AS PHARMACEUTICALLY ACTIVE AGENTS

(71) Applicant: VICHEM CHEMIE KUTATÓ KFT., Budapest (HU)

(72) Inventors: Ferenc Baska, Budapest (HU); György Kéri, Budapest (HU); Lászó Orfi, Budapest (HU); Péter Bánhegyi, Budapest (HU); László Kékesi, Budapest (HU); Lilian Zsákai, Budapest (HU); Anna Sipos, Dunakeszi (HU); Csaba Szántai-kis, Budapest (HU); Judit Dobos, Budapest (HU); Tanneke Den Blaauwen, Amsterdam (NL)

(73) Assignee: Vichem Chemie Kutató Kft., Budapest (HU)

( * ) Notice: Subject to any disclaimer, the term of this patent is extended or adjusted under 35 U.S.C. 154(b) by 0 days.

(21) Appl. No.: 14/911,159

(22) PCT Filed: Aug. 7, 2014

(86) PCT No.: PCT/HU2014/000069
§ 371 (c)(1),
(2) Date: Feb. 9, 2016

(87) PCT Pub. No.: WO2015/019121
PCT Pub. Date: Feb. 12, 2015

(65) Prior Publication Data
US 2016/0194291 A1    Jul. 7, 2016

(30) Foreign Application Priority Data

Aug. 9, 2013    (HU) .................................... 1300477

(51) Int. Cl.
*C07D 239/94*    (2006.01)
*C07D 403/12*    (2006.01)
*C07D 403/04*    (2006.01)
*C07D 413/12*    (2006.01)
*C07D 471/10*    (2006.01)
*C07D 403/14*    (2006.01)
*C07D 409/06*    (2006.01)
*C07D 491/113*    (2006.01)

(52) U.S. Cl.
CPC ......... *C07D 239/94* (2013.01); *C07D 403/04* (2013.01); *C07D 403/12* (2013.01); *C07D 403/14* (2013.01); *C07D 409/06* (2013.01); *C07D 413/12* (2013.01); *C07D 471/10* (2013.01); *C07D 491/113* (2013.01)

(58) Field of Classification Search
CPC .............. C07D 239/94; C07D 491/113; C07D 403/04; C07D 403/12; C07D 403/14; C07D 409/06; C07D 471/10; C07D 413/12
See application file for complete search history.

(56) References Cited

U.S. PATENT DOCUMENTS

| 3,753,981 A | 8/1973 | Breuer et al. |
| 7,790,474 B1 * | 9/2010 | Dasmahapatra ... G01N 33/5011 435/7.1 |
| 2004/0034044 A1 | 2/2004 | Okano et al. |
| 2008/0103163 A1 | 5/2008 | Oyama et al. |

FOREIGN PATENT DOCUMENTS

| WO | 02/062767 A1 | 8/2002 |
| WO | 2004/030671 A2 | 4/2004 |
| WO | 2013178569 | * 12/2013 |

OTHER PUBLICATIONS

Reddy et al.: "Identification and structure-activity relationship studies of 3-methylene-2-norbornanone as potent anti-proliferative agents presumably working through p53 mediated apoptosis", Bioorganic & Medicinal Chemistry Letters, 2004, vol. 14, pp. 5645-5649.

Okano et al.: "Discovery and structure-activity relationships of 4-aminoquinazoline derivatives, a novel class of opioid-receptor like-1 (ORL1) antagonists", Bioorganic & Medicinal Chemistry, 2009, vol. 17, pp. 119-132.

Yakhontov et al.: "Synthesis and Study of Biological Activity of Substituted 4-Amino-2-Styrylquinazolines", Pharmaceutical Chemistry Journal, 1975, vol. 9, pp. 692-698.

Zhukhareva et al.: "Synthesis and Study of the Antiinflammatory Action of Substituted 4-Amino-2-Styrylquinazolines", Pharmaceutical Chemistry Journal, 1977, vol. 11, pp. 1354-1357.

Fadeeva et al.: "Molecular Biological Problems of the Creation of Drugs and Study of Their Action Investigation of the Interaction of DNA With 2-Strylquinoline and 2-Styrylquinazoline Derivatives", Pharmaceutical Chemistry Journal, 1987, vol. 21, pp. 1-4.

Zhikhareva et al.: "Synthesis and Anti-Inflammatory Activity of Substituted 2-Styryl-4-(delta-Diethylamino-alpha-Methylbutylamino)-6-Nitro- and 2-Styryl-4-(delta-Diethylamino-alpha-Methylbutylamino)-6-Aminoquinazolines", Pharmaceutical Chemistry Journal, 1980, vol. 14, pp. 119-123.

(Continued)

*Primary Examiner* — Alexander R Pagano
*Assistant Examiner* — Ebenezer O Sackey
(74) *Attorney, Agent, or Firm* — Jason D. Voight

(57) ABSTRACT

The present invention relates to styryl quinazoline derivatives of the general formula (I) and pharmaceutically acceptable solvates, hydrates, salts, regioisomeric and polymorphic forms thereof as well as pharmaceutical compositions containing at least one of the described compounds as pharmaceutically active agent. The compounds have been identified as new drug candidates for the prevention and/or treatment of diseases related to disfunction(s) of hematopoiesis and cancer or any other form of neo- or hyperplasias related to Fms-like tyrosine kinase 3 (FLT3) containing Internal Tandem Duplications (ITD), especially in the case of myeloid leukemia. The compounds have been also identified as new drug candidates as antibacterial agents (having bactericidal or bacteriostatic activity) which can be used for the prevention and/or treatment of bacterial infectious diseases.

12 Claims, No Drawings

(56) References Cited

OTHER PUBLICATIONS

Margalit et al.: "Targeting cell division: Small-molecule inhibitors of FtsZ GTPase perturb cytokinetic ring assembly and induce bacterial lethality", Proceedings of the National Academy of Sciences, 2004, vol. 101, pp. 11821-11826.

El-Kerdawy et al.: "Synthesis and Biological Testing of Certain Thienyl-vinyl-quinazolines and Thienyl pyridones as Antibacterial Agents", 1976, Acta Pharmaceutica Jugoslavica, vol. 26, pp. 135-140.

Anderson et al.: "Comparison of Small Molecule Inhibitors of the Bacterial Cell Division Protein FtsZ and Identification of a Reliable Cross-Species Inhibitor", ACS Chemical Biology, 2012, vol. 7, pp. 1918-1928.

\* cited by examiner

STYRYL QUINAZOLINE DERIVATIVES AS PHARMACEUTICALLY ACTIVE AGENTS

This is the national stage of International Application PCT/HU2014/000069, filed Aug. 7, 2014.

FIELD OF THE INVENTION

In accordance with the purposes of the present invention, as embodied and broadly described herein, the present invention includes styryl quinazoline derivatives of the general formula (I) and pharmaceutically acceptable solvates, hydrates, salts, regioisomeric and polymorphic forms thereof as well as pharmaceutical compositions containing at least one of the described compounds as pharmaceutically active agent, together with pharmaceutically acceptable carrier, excipient and/or diluents and the use of them for therapeutic or preventive purposes, especially regarding cancer or any other form of neo- or hyperplasias.

Moreover, the present invention provides processes for the preparation of the described compounds. The styryl quinazoline derivatives disclosed in this invention have been identified as new drug candidates for the prevention and/or treatment of diseases related to disfunction(s) of hematopoiesis and cancer or any other form of neo- or hyperplasias related to (depending on) Fms-like tyrosine kinase 3 (FLT3) containing Internal Tandem Duplications (ITD), especially in the case of myeloid leukemia. Accordingly, the styryl quinazoline derivatives of the general formula (I) and pharmaceutically acceptable solvates, hydrates, salts, regioisomeric and polymorphic forms thereof have inhibitory effect on Fms-like tyrosine kinase 3 (FLT3) containing Internal Tandem Duplications (ITD).

The discussed styryl quinazoline compounds have been also identified as new drug candidates as antibacterial agents (having bactericidal or bacteriostatic activity) which can be used for the prevention and/or treatment of bacterial infectious diseases e.g. meningitis of bacterial origin, gastroenteritis of bacterial origin, *E-coli* and *Staphylococcus saprophyticus* caused Urinary Tract Infections (UTI), *E. coli, Shigella* and *Campylobacter* associated Hemolytic-Uremic Syndrome (HUS), infected peritonitis, infectious mastitis, bacteraemia (bacteria caused sepsis), *E. coli, Klebsiella, Pseudomonas, B. fragilis* and *Enterococcus* caused cholecystitis, and common types of pneumonia.

BACKGROUND OF THE INVENTION

Fms-like tyrosine kinase 3 (FLT3), also known as Cluster of Differentiation antigen 135 (CD135), Fetal liver kinase-2 (Flk2) and Stem cell Tyrosine Kinase 1 (STK1) is a human protein (Uniprot ID: P36888) encoded by the human gene FLT3 (HGNC ID: 3765). This protein is specifically appearing on the surface of hematopoietic progenitor cells after they cease to be hematopoietic stem cells related to FLT3 expression. FLT3 regulates the maturation processes in order to develop them into functional blood cells, especially to develop properly functioning lymphocytes, alias T-cells and B-cells. The hematopoietic progenitor cells are multipotent cells, and the dysregulation of their differentiation processes often results pathologic conditions. FLT3 is one the most important regulators of this cellular maturation process, therefore mutations or overexpression of this protein are associated with several types of blood cell malignancies, including acute myeloid leukemia. As more and more information has been gathered about FLT3's role as an oncogene, FLT3's Internal Tandem Duplications (ITD) type of mutation is by now considered as a disease-specific 'driver' mutation. FLT(ITD) is a mutation that is a crucial turning point-like factor that moves differentiation and proliferation processes toward the initiation and progression of acute myeloid leukemia in a disease-specific way. The unique expression pattern of the mutated protein makes it a highly promising target in terms of developing really targeted and protein-specific signal transduction therapies.

FLT3 is a member of receptor tyrosine kinases class III. This class's domain structure significantly differs from the other classes' and the class contains only a few members. The kinase domain of FLT3 is relatively different compared to the mainstream targeted Tyrosine Kinases This fact indicates that the potent inhibitors of FLT3(ITD) are having a rather selective profile among Receptor Tyrosine Kinases. The effectiveness and the selectivity has been proven by in vitro biochemical assays, cellular viability assays and using a wide kinase selectivity panel.

As it was mentioned above, the styryl quinazoline compounds according to the present invention also can be applied as antibacterial agents (having bactericidal or bacteriostatic activity) for the prevention and/or treatment of bacterial infectious diseases such as meningitis of bacterial origin, gastroenteritis of bacterial origin, *E. coli* and *Staphylococcus saprophyticus* caused Urinary Tract Infections (UTI), *E. coli, Shigella* and *Campylobacter* associated Hemolytic-Uremic Syndrome (HUS), infected peritonitis, infectious mastitis, bacteraemia (bacteria caused sepsis), *E. coli, Klebsiella, Pseudomonas, B. fragilis* and *Enterococcus* caused cholecystitis, and common types of pneumonia.

Pathogenic bacteria are a major cause of human death and disease and cause infectious diseases—besides inflammation based pathogenic states mentioned above—such as tetanus, typhoid fever, diphtheria, syphilis, cholera, foodborne illness, leprosy and tuberculosis. Bacterial infections may be treated with antibiotics (antibacterial agents), which are classified as bactericidal if they kill bacteria, or bacteriostatic if they just prevent bacterial growth.

*Escherichia coli* (*E. coli*, named after Theodor Escherich) is a Gram-negative, facultatively anaerobic, rod-shaped bacterium of the genus *Escherichia* that is commonly found in the lower intestine of endothermic organisms.

Most *E. coli* strains are harmless, but certain serotypes are pathogenic to humans or domestic animals. Virulent strains of *E. coli* are the dominant causes of various diseases; such as meningitis, gastroenteritis and UTI and less often can cause HUS, peritonitis, mastitis, bacteraemia and gram-negative pneumonia. Certain strains of *E. coli* produce also potentially lethal toxins, e.g. Enterotoxigenic *E. coli* (ETEC), Enteropathogenic *E. coli* (EPEC), Enteroinvasive *E. coli* (EIEC), Enterohemorrhagic *E. coli* (EHEC), Enteroaggregative *E. coli* (EAEC) which are causative agents of diarrhea and other gastrointestinal symptoms, and Uropathogenic *E. coli* (UPEC) which causes urinary tract inflammation and infection. There are also some *E. coli* strains that contain a polyketide synthase (PKS) genomic island whose function is to encode multiple PKSs, a multi-enzymatic machinery that produces a genotoxic substance, named colibactin. This substance can promote tumorigenesis by DNA damage.

SUMMARY OF THE INVENTION

1. The present invention relates to compounds of general formula (I) and pharmaceutically acceptable salts, solvates, hydrates, regioisomeric and polymorphic forms thereof, (I)

[Structure: quinazoline with R2, R3, R4 substituents on the benzene ring, R1 at position 4, and a vinyl-Q group at position 2]

wherein

R1 is N(R5)(R6), wherein

R5 and R6 are independently selected from the group of hydrogen, alkyl or ALK-N(R7)(R8), wherein ALK is an alkanediyl group and R7 and R8 are independently selected from the group of hydrogen, alkyl, alkylcarbonyl and alkoxycarbonyl; or R7 and R8 taken together with the adjacent N form a saturated heterocyclyl which is optionally substituted with alkyl;

or R5 and R6 taken together with the adjacent N may form a heterocyclyl optionally substituted heterocyclyl-alkyl or a cycloketal group is joined to it;

R2 is hydrogen or halogen;

R3 and R4 are independently selected from the group of hydrogen, halogen, alkoxy or nitro group;

or R3 and R4 together with the carbon atoms they attached to may form an aryl fused to the quinazoline ring;

Q is aryl optionally mono or polysubstituted with halogen, alkyl, dialkylamine, alkoxy, alkylsulfanyl, alkylsulfinyl, or alkylsulfonyl; or heteroaryl group;

2. Compound according to point 1, wherein

R7 and R8 are independently selected form hydrogen, methyl, ethyl, methylcarbonyl and methoxycarbonyl, or R7 and R8 taken together with N form morpholin-4-yl or 4-methylpiperazin-1-yl ring.

3. Compound according to point 1 or 2, wherein R5 and R6 are independently selected form hydrogen, propyl, ethyl-N(R7)(R8), 1-prop-3-yl-N(R7)(R8), pent-1,4-diyl-N(R7)(R8) or R5 and R6 taken together with N form 1,4-dioxa-8-azaspiro[4.5]dec-8-yl or (pyrrolidin-1-ylmethyl)pyrrolidin-1-yl.

4. Compound according to any of points 1 to 3, wherein R2 is hydrogen or bromine.

5. Compound according to any of points 1 to 4, wherein R3 is hydrogen, chlorine, nitro or methoxy.

6. Compound according to any of points 1 to 5, wherein R4 is hydrogen, fluorine, chlorine, bromine or methoxy; or R3 and R4 together with the carbon atoms they attached to may form an aryl fused to the quinazoline ring.

7. Compound according to any of points 1 to 6, wherein Q is phenyl mono or polysubstituted with fluorine, chlorine, methoxy, dimethylamino, i-propyl, methylthio, methylsulfonyl group; or thienyl.

8. Compound according to any of points 1 to 7, wherein R1 is 1-dimethylamino-propane-3-ylamino, 1-diethylamino-propane-3-ylamino, 3-(morpholin-4-yl)propylamino, 3-(4-methylpiperazin-1-yl)propylamino, 1-dimethylamino-2-ethylamino, 1-dimethylamino-2-ethylamino, 1-diethylamino-pentane-4-yl-amino, 1-(tertbutylcarbamate)-propane-3-yl-amino, 1-amino-propane-3-yl-amino, 1-acetylamino-propane-3-yl-amino, 1-(piperidin-4-one-ethylenketal), 2-(pyrrolidin-1-ylmethyl)pyrrolidin-1-yl, propane-3-yl-amino;

R2, R3 and R4 being as defined in point 4 to 6;

Q is 4-methoxy-phenyl, 3-fluoro-phenyl, 4-fluoro-phenyl, 4-chloro-phenyl, 4-(dimethylamino)phenyl, 3,4,5-trimethoxyphenyl, 3,4-difluorophenyl, 4-(methylthio)phenyl, 2-thienyl, 4-isopropylphenyl or 4-(methylsulfonyl)phenyl.

9. Pharmaceutical composition containing as active ingredient one or more compound(s) of general formula (I) according to any of points 1 to 8 together with one or more usual pharmaceutical auxiliary material(s).

10. Compounds according to any of points 1 to 8 for use in the prevention and/or treatment of a disease related to disfunction of hematopoiesis and/or a cancerous, neoplastic or hyperplastic disease.

11. Compounds for use according to point 10, wherein the disfunction of hematopoiesis and the cancer or any other form of neo- or hyperplasias are related to the Fms-like tyrosine kinase 3 (FLT3) containing Internal Tandem Duplications (ITD).

12. Compounds according to any of points 1 to 8 for use in the prevention and/or the treatment of bacterial infectious diseases.

13. Compounds for use according to point 12, wherein the bacterial infectious diseases is selected from meningitis of bacterial origin, gastroenteritis of bacterial origin, *E. coli* and *Staphylococcus saprophyticus* caused Urinary Tract Infections (UTI), *E. coli*, *Shigella* and *Campylobacter* associated Hemolytic-Uremic Syndrome (HUS), infected peritonitis, infectious mastitis, bacteraemia (bacteria caused sepsis), *E. coli*, *Klebsiella*, *Pseudomonas*, *B. fragilis* and *Enterococcus* caused cholecystitis, and common types of pneumonia.

14. The compounds invented can be applied in a method for the prevention and/or the treatment of a disease related to disfunction of hematopoiesis and/or a cancerous, neoplastic or hyperplastic disease, where a compound of general formula (I) according to any of points 1 to 8 is administered to an individual in need thereof. Specifically, the disfunction of hematopoiesis and cancer or any other form of neo- or hyperplasias are related to the Fms-like tyrosine kinase 3 (FLT3) containing Internal Tandem Duplications (ITD).

15. The compounds invented can be applied in a method for the prevention and/or the treatment of bacterial infectious diseases, where a compound of general formula (I) according to any of points 1 to 8 is administered to an individual in need thereof. Specifically, the bacterial infectious diseases is selected from meningitis of bacterial origin, gastroenteritis of bacterial origin, *E. coli* and *Staphylococcus saprophyticus* caused Urinary Tract Infections (UTI), *E. coli*, *Shigella* and *Campylobacter* associated Hemolytic-Uremic Syndrome (HUS), infected peritonitis, infectious mastitis, bacteraemia (bacteria caused sepsis), *E. coli*, *Klebsiella*, *Pseudomonas*, *B. fragilis* and *Enterococcus* caused cholecystitis, and common types of pneumonia.

DETAILED DESCRIPTION OF THE INVENTION

In the context of this description the phrase "cancer" embraces adenocarcinomas (breast, colon, colorectal and colorectal adenocarcinoma, epidermoid, lung bronchioalveolar and lung adenocarcinoma), the cancerous disease of the genital system (including uterine cervix, uterine corpus, ovary, vulva, vagina and other genital female, prostate, testis, penis and other genital male), digestive system (including esophagus, stomach, small intestine, colon, rectum, anus anal canal and anorectum, liver and intrahepatic bile duct, gallbladder and other biliary, pancreas, other digestive organs), respiratory system (including larynx, lung and bronchus, other respiratory organs), breast, urinary system (including urinary bladder, kidney and renal pelvis, ureter and other urinary organs), skin (excluding basal and squamous; including skin melanoma, other nonepithelial skin), endocrine system (including thyroid, other endocrine), oral cavity and pharynx (including tongue, mouth, pharynx, other oral cavity), brain and other nervous system, myeloma, soft tissue (including heart), bones and joints, eye and orbit, and the following diseases: lymphoma (including Hodgkin lymphoma, Non-Hodgkin lymphoma), leukemia (including acute lymphocytic leukemia, chronic lymphocytic leukemia, acute myeloid leukemia, chronic myeloid leukemia, other leukemia), especially acute T-cell leukemia, breast, colon, colorectal and colorectal adenocarcinoma, epidermoid, lung bronchioalveolar and lung adenocarcinoma, prostate.

Hyperplasia (or "hypergenesis") is a general term referring to the proliferation of cells within an organ or tissue beyond that which is ordinarily seen. Hyperplasia may result in the gross enlargement of an organ and the term is sometimes mixed with benign neoplasia/benign tumor.

Neoplasm is an abnormal mass of tissue as a result of neoplasia. Neoplasia is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

FLT3 is naturally expressed by immature hematopoietic (blood cell forming) cells and is important for the normal development of stem cells and the immune system. The ligand for FLT3 synergizes with other growth factors to stimulate proliferation of stem cells, progenitor cells, dendritic cells, and natural killer cells. Mutations of FLT3 (mainly the FLT3[ITD] mutation which is investigated in our case) have been detected in about 30% of patients with acute myelogenous leukemia and a small number of patients with acute lymphocytic leukemia or myelodysplastic syndrome. FLT3 is also expressed in a wild type form at high levels in 70% to 100% of cases of acute myelogenous leukemia and in a high percentage of acute lymphocytic leukemia cases [D. Gary Gilliland and James D. Griffin: The roles of FLT3 in hematopoiesis and leukemia, Sep. 1, 2002; Blood: 100 (5)].

As used herein in the meaning of R1 (i.e. in the meaning of R5, R6, R7 and R8), the term "heterocyclyl" alone or in combination, means a group derived from a saturated, partially unsaturated or aromatic ring system with 4 to 9 carbon atoms and 1 to 4 heteroatom(s) selected from the group of N, O and S [i.e. group of N (nitrogen), O (oxygen) or S (sulfur) atoms]. In a preferred embodiment the term "heterocyclyl" alone or in combination, means a saturated ring system with 4 to 7 carbon atoms and 1 to 3 heteroatom(s) selected from the group of N, O and S. In a more preferred embodiment the term "heterocyclyl" means a saturated ring system with 4 to 6 carbon atoms and 1 to 2 heteroatom(s) selected from the group of N and O. Examples for heterocyclyl (includes but not limited to) are morpholinyl, pyrrolidinyl, piperazinyl, piperidinyl, indolyl, indazolyl, 1,3-benzodioxolyl, dihydro-1,4-benzodioxinyl, furanyl, pyrrolyl, pyridinyl, quinolinyl, isoquinolinyl, pyranyl, oxazinyl, imidazolyl, benzoimidazolyl, pyrazolyl, purinyl, where morpholinyl, pyrrolidinyl, piperazinyl and piperidinyl are preferred.

Those substituted heterocyclyl groups are also within the scope which contain one or more substituent(s) usually applied in the organic chemistry for substitution of heterocyclyl groups. So, the substituted heterocyclyl groups carry one or more, preferably 1 to 4 substituent(s), e.g. 1 to 3 or 1 to 2 substituent(s), independently selected from the group of halogen, alkyl, hydroxyl, hydroxyalkyl [preferably the substituent is alkyl, more preferably methyl].

As used herein the term "aryl", alone or in combinations means an aromatic monocyclic or multicyclic ring system comprising 6 to 14 carbon atoms, preferably 6 to 10 carbon atoms. Non-limiting examples of suitable aryl groups include phenyl, and naphthyl, where phenyl is a preferred embodiment.

Those substituted aryl groups are also within the scope which contain one or more substituent(s) usually applied in the organic chemistry for substitution of aryl groups. So, the substituted aryl groups carry one or more, preferably 1 to 4, e.g. 1 to 3 or 1 to 2 substituent(s), independently selected from the group of halogen, alkyl, alkoxy, amino, optionally mono- or disubstituted with alkyl, amide, acylamino, alkylthio, alkylsulfinyl, alkylsulfonyl and cyano.

In specific embodiments the substituent of the aryl can be optionally substituted alkyl (more preferably propyl, e.g. isopropyl), halogen (e.g. fluoro or chloro), alkoxy (more preferably methoxy), dialkylamino (e.g. dimethylamino), alkylthio (e.g. methylthio), alkylsulfonyl (e.g. methylsulfonyl).

As used herein, the term "alkanediyl" means a bivalent group formed by the removal of 2 hydrogen atoms from different carbon atoms of an C1-6 alkane group, i.e. it can be a straight or branced group, e.g. ethane-1,2-diyl, propane-1,3-diyl and pentane-1,4-diyl group.

As used herein, the term "halogen" means fluorine, chlorine, bromine or iodine.

As used herein, the term "alkyl" alone or in combinations means a straight or branched-chain alkyl group containing from 1 to 6, preferably 1 to 5 carbon atom(s) (i.e. "$C_{1-6}$" or "$C_{1-5}$" alkyl groups), such as methyl, ethyl, propyl, isopropyl, butyl, sec-butyl, t-butyl and pentyl. In special cases this phrase can relate to alkyl groups containing from 1 to 4, or 1 to 3 or 1 to 2 carbon atom(s) (i.e. "$C_{1-4}$" or "$C_{1-3}$" or "$C_{1-2}$" alkyl groups). Those substituted alkyl groups are also within the scope which contain one or more substituent(s) usually applied in the organic chemistry for substitution of alkyl groups. So, the substituted alkyl groups carry one or more, preferably one or two substituent(s), independently selected from the group of halogen, aryl, hydroxyl, carboxyl, benzyloxy, alkoxy, nitro, sulphate, amino, acylamino, monoalkylamino, dialkylamino, alkylthio, alkylsulfinyl, alkylsulfonyl and cyano.

As used herein, the term "alkylcarbonyl" means an alkyl-CO— group.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen. If the alkoxy group is substituted with halogen then it is named as haloalkoxy group.

As used herein, the term "alkoxycarbonyl" means an alkoxy-CO— group [i.e. alkyl-O(CO) group].

As used herein, the term "cycloketal" means a bivalent group of —O—$(CH_2)_n$—O— which is joined to the same carbon atom (e.g. of a ring system), where n is 1 to 4, preferably 2 or 3, more preferably 2.

As used herein in the meaning of Q the term "heteroaryl" means a group derived from an aromatic ring system with 4 to 9 carbon atoms and 1 to 4 heteroatom(s) selected from the group of N, O and S [i.e. group of N (nitrogen), O (oxygen) or S (sulfur) atoms]. In a preferred embodiment the term "heteroaryl", means an aromatic ring system with 4 to 7 carbon atoms and 1 to 3 heteroatom(s) selected from the group of N, O and S. In a more preferred embodiment the term "heteroaryl" means an aromatic ring system with 4 to 5 carbon atoms and 1 to 2 heteroatom(s) selected from the group of N, O and S. In a specific embodiment the heteroatom(s) is (are) sulphur. Examples for heteroaryl are indolyl, imidazolyl, azaindolyl, pyrrolyl, quinolinyl, isoquinolinyl, oxazolyl, thiazolyl, thienyl and pyrimidinyl where thienyl is preferred.

The term "salt" means any ionic compound formed between one of the embodiments of the present invention and an acidic or basic molecule that can donate or accept ionic particle to/from its partner. The quaternary amine salts are also included.

Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

The term "solvate" means a compound formed by the combination of solvent molecules with molecules or ions of the solute (solvation). Solute can be any of the embodiments of the present invention and the solvent can be water (forming hydrates) or any organic solvent.

The phrases of regioisomeric and polymorphic forms have the general meaning usually applied in organic chemistry (see e.g. in March's Advanced Organic Chemistry, John Wiley & Sohns, inc. USA. ISBN 0-471-58589-0).

Materials and Methods:
Synthetic Methods:

Step A: Preparation of mono- or di substituted 2-methylquinazolin-4(3H)-ones

Scheme 1

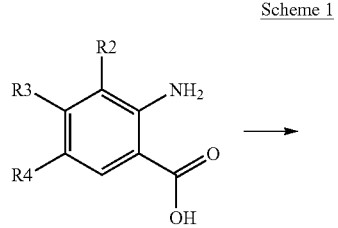

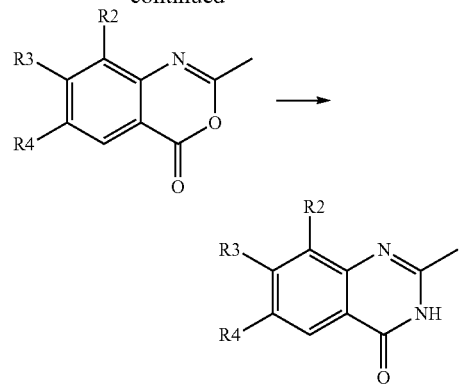

6-chloro-2-methylquinazolin-4(3H)-one 10 g (58 mmol) 2-amino-5-chlorobenzoic acid was solved in 35 ml acetic anhydride and was stirred at reflux temperature for 4 hours. The reaction mixture was cooled down to room temperature and the solvent was rotary evaporated. The crude product was washed with hexane/ether 2:1 and than filtered. The solid 6-chloro-2-methyl-4H-3,1-benzoxazin-4-one (58 mmol) was suspended in 80 ml concentrated ammonium hydroxide and stirred at room temperature overnight. 10% sodium hydoxide solution was given to the reaction mixture resulting a transparent solution. The pH was adjusted to 7 with acetic acid. The product, which was precipitated from the solution, was filtered, washed with water and dried under vacuum overnight.

Preparation of other 2-methylquinazolin-4(3H)-one derivatives were carried out with the same method.

Yield: 8.76 g (77%)

$^1$H NMR (300 MHz, DMSO-$d_6$) δ ppm 7.98 (s, 1H); 7.76 (6 Hz, d, 1H); 7.57 (9 Hz, d, 1H); 2.34 (s, 3H). LC-MS (ESI): m/z (M+H)$^+$ 195, Rt: 2.43 min.

6-fluoro-2-methylquinazolin-4(3H)-one $^1$H NMR (300 MHz, DMSO-$d_6$) δ ppm 12.29 (bs, NH); 7.74-7.63 (m, 3H); 2.34 (s, 3H). LC-MS (ESI): m/z (M+H)$^+$ 179, Rt: 2.01 min.

6-bromo-2-methylquinazolin-4(3H)-one $^1$H NMR (300 MHz, DMSO-$d_6$) δ ppm 8.13 (s, 1H); 7.88 (9 Hz, d, 1H); 7.50 (9 Hz, d, 1H); 2.33 (s, 1H). LC-MS (ESI): m/z (M+H)$^+$ 239, Rt: 2.52 min.

2-methyl-7-nitroquinazolin-4(3H)-one $^1$H NMR (300 MHz, DMSO-$d_6$) δ ppm 12.40 (bs, 1H); 8.29 (d, 1H); 8.26 (s, 1H); 8.16 (d, 1H); 2.40 (s, 3H). LC-MS (ESI): m/z (M+H)$^+$ 206, Rt: 2.34 min.

6,7-dimethoxy-2-methylquinazolin-4(3H)-one $^1$H NMR (300 MHz, DMSO-$d_6$) δ ppm 12.00 (bs, 1H); 7.39 (s, 1H); 7.05 (s, 1H); 3.88 (s, 3H); 3.85 (s, 1H); 2.31 (s, 3H). LC-MS (ESI): m/z (M+H)$^+$ 221, Rt: 0.45 min, 1.78 min.

2-methylbenzo[g]quinazolin-4(3H)-one

The starting 3-amino-2-naphthoic acid was only 85% pure and contained the other regioisomer too. The product was 67% pure to the right isomer. We used this product for the next reaction without purification. LCMS m/z 211 (M+H)+, Rt: 2.40 min (desired compound), 2.61 min (other isomer)

7-chloro-2-methylquinazolin-4(3H)-one $^1$H NMR (300 MHz, DMSO-d$_6$) δ ppm 8.06 (d, 1H); 7.60 (d, 1H); 7.46 (dd, 1H); 3.50 (bs, 1H); 2.35 (s, 3H). LC-MS (ESI): m/z (M+H)+ 195, Rt: 2.48 min.

6,8-dibromo-2-methylquinazolin-4(3H)-one $^1$H NMR (300 MHz, DMSO-d$_6$) δ ppm 8.14 (s, 1H); 8.09 (s, 1H); 3.80 (bs, 1H); 2.32 (s, 3H). LC-MS (ESI): m/z (M+H)+ 319, Rt: 3.27 min.

Step B: Preparation of substituted 2-[(E)-2-phenyl-vinyl]quinazolin-4(3H)-ones

Scheme 2

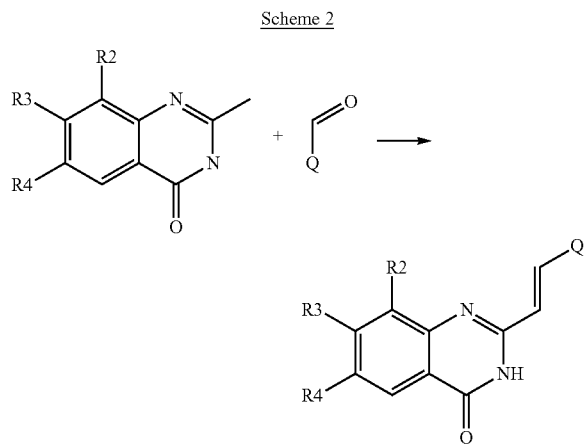

6-chloro-2-[(E)-2-(4-methoxyphenyl)vinyl]quinazolin-4(3H)-one 3 g (15 mmol) 6-chloro-2-methylquinazolin-4(3H)-one was mixed with 3.06 g (22.5 mmol) 4-methoxybenzaldehyde and 1 drop concentrated sulphuric acid was given to this mixture. The reaction was carried out in microwave set at 190° C. Reaction time was 2 hour. The crude product was washed with 5% sodium hydrogen carbonate and filtered. The product was crystallized from dimethyl formamide and dried under vacuum.

Yield: 4.58 g (95%)
$^1$H NMR (300 MHz, DMSO-d$_6$) δ ppm 8.02 (d, 1H); 7.92 (d, 1H); 7.81 (d, 1H); 7.66 (d, 1H); 7.66 (d, 1H); 7.61 (d, 2H); 7.03 (d, 2H); 6.85 (d, 1H); 3.81 (s, 3H). LC-MS (ESI): m/z (M+H)+ 313, Rt: 4.07 min.

Preparation of other 2-[(E)-2-phenylvinyl]quinazolin-4(3H)-one derivatives were carried out with the same method.

6-chloro-2-[(E)-2-(4-fluorophenyl)vinyl]quinazolin-4(3H)-one $^1$H NMR (300 MHz, DMSO-d$_6$) δ ppm 12.47 (bs, 1H); 8.04 (d, 1H); 7.95 (d, 1H); 7.83 (dd, 1H); 7.72 (m, 3H); 7.30 (t, 2H); 6.95 (d, 1H). LC-MS (ESI): m/z (M+H)+ 301, Rt: 4.13 min.

6-chloro-2-[(E)-2-(3,4-difluorophenyl)vinyl]quinazolin-4(3H)-one $^1$H NMR (300 MHz, DMSO-d$_6$) δ ppm 12.48 (bs, 1H); 8.03 (s, 1H); 7.90 (d, 1H); 7.79 (m, 2H); 7.68 (d, 1H); 7.53 (m, 2H); 6.99 (d, 1H). LC-MS (ESI): m/z (M+H)+ 319, Rt: 4.21 min.

6-chloro-2-{(E)-2-[4-(methylthio)phenyl]vinyl}quinazolin-4(3H)-one $^1$H NMR (300 MHz, DMSO-d$_6$) δ ppm 12.40 (bs, 1H); 8.02 (s, 1H); 7.91 (d, 1H); 7.80 (d, 1H); 7.67 (d, 1H); 7.59 (d, 2H); 7.33 (d, 2H); 6.95 (d, 1H); 2.52 (s, 3H). LC-MS (ESI): m/z (M+H)+ 329, Rt: 4.38 min.

6-fluoro-2-[(E)-2-(4-methoxyphenyl)vinyl]quinazolin-4(3H)-one $^1$H NMR (300 MHz, DMSO-d$_6$) δ ppm 12.35 (bs, 1H); 7.90 (d, 1H); 7.71 (m, 3H); 7.61 (d, 2H); 7.03 (d, 2H); 6.84 (d, 1H); 3.81 (s, 3H). LC-MS (ESI): m/z (M+H)+ 297, Rt: 3.70 min.

6-fluoro-2-[(E)-2-(4-fluorophenyl)vinyl]quinazolin-4(3H)-one $^1$H NMR (300 MHz, DMSO-d$_6$) δ ppm 12.42 (bs, 1H); 7.93 (d, 1H); 7.72 (m, 5H); 7.30 (t, 2H); 6.95 (d, 1H). LC-MS (ESI): m/z (M+H)+ 285, Rt: 3.79 min.

6-fluoro-2-[(E)-2-(3,4-difluorophenyl)vinyl]quinazolin-4(3H)-one $^1$H NMR (300 MHz, DMSO-d$_6$) δ ppm 12.44 (bs, 1H); 7.88 (d, 1H); 7.65 (m, 4H); 7.51 (bs, 2H); 6.98 (d, 1H). LC-MS (ESI): (M+H)+ 303, Rt: 3.90 min.

6-bromo-2-[(E)-2-(4-methoxyphenyl)vinyl]quinazolin-4(3H)-one $^1$H NMR (300 MHz, DMSO-d$_6$) δ ppm 12.39 (bs, 1H); 8.16 (s, 1H); 7.95 (s, 1H); 7.94 (d, 1H); 7.61 (bs, 3H); 7.03 (d, 2H); 8.85 (d, 1H); 3.82 (s, 3H). LC-MS (ESI): m/z (M+H)+ 357, Rt: 4.15 min.

6-bromo-2-[(E)-2-(4-fluorophenyl)vinyl]quinazolin-4(3H)-one $^1$H NMR (300 MHz, DMSO-d$_6$) δ ppm 12.47 (bs, 1H); 8.18 (d, 1H); 7.95 (d, 1H); 7.92 (s, 1H); 7.73 (m, 2H); 7.62 (d, 1H); 7.30 (t, 2H); 6.95 (d, 1H). LC-MS (ESI): m/z (M+H)+ 345, Rt: 4.22 min.

6-bromo-2-[(E)-2-(3,4-difluorophenyl)vinyl]quinazolin-4(3H)-one $^1$H NMR (300 MHz, DMSO-d$_6$) δ ppm 12.47 (bs, 1H); 8.18 (s, 1H); 7.91 (d, 1H); 7.93 (s, 1H); 7.78 (t, 1H); 7.61 (d, 1H); 7.52 (bs, 2H); 6.99 (d, 1H). LC-MS (ESI): m/z (M+H)+ 363, Rt: 4.30 min.

2-[(E)-2-(4-methoxyphenyl)vinyl]-7-nitroquinazolin-4(3H)-one $^1$H NMR (300 MHz, DMSO-d$_6$) δ ppm 12.56 (bs, 1H); 8.30 (s, 1H); 8.29 (d, 1H); 8.13 (d, 1H); 7.98 (d, 1H); 7.62

(d, 2H); 7.03 (d, 2H); 6.86 (d, 1H); 3.82 (s, 3H). LC-MS (ESI): m/z (M+H)+ 324, Rt: 3.96 min.

2-[(E)-2-(4-fluorophenyl)vinyl]-7-nitroquinazolin-4(3H)-one $^1$H NMR (300 MHz, DMSO-d$_6$) δ ppm 12.65 (bs, 1H); 8.33 (d, 1H); 8.30 (s, 1H); 8.17 (dd, 1H); 8.02 (d, 1H); 7.74 (m, 2H); 7.32 (t, 2H); 6.97 (d, 1H). LC-MS (ESI): m/z (M+H)+ 312, Rt: 4.01 min.

6,7-dimethoxy-2-[(E)-2-(4-methoxyphenyl)vinyl]quinazolin-4(3H)-one $^1$H NMR (300 MHz, DMSO-d$_6$) δ ppm 8.17 (t, 1H); 8.06 (dd, 1H); 7.87 (d, 1H); 7.74 (m, 3H); 7.64 (dt, 1H); 7.25 (t, 2H); 7.08 (d, 1H); 3.67 (q, 2H); 3.57 (t, 4H); 2.40 (m, 6H); 1.86 (m, 2H). LC-MS (ESI): m/z (M+H)+ 339, Rt: 3.26 min.

6,7-dimethoxy-2-[(E)-2-(4-fluorophenyl)vinyl]quinazolin-4(3H)-one $^1$H NMR (300 MHz, DMSO-d$_6$) δ ppm 12.45 (bs, 1H); 7.88 (d, 1H); 7.69 (m, 2H); 7.45 (s, 1H); 7.30 (t, 2H); 7.14 (s, 1H); 6.91 (d, 1H). LC-MS (ESI): m/z (M+H)+ 327, Rt: 3.40 min.

6,7-dimethoxy-2-[(E)-2-(3,4-difluorophenyl)vinyl]quinazolin-4(3H)-one $^1$H NMR (300 MHz, DMSO-d$_6$) δ ppm LC-MS (ESI): m/z (M+H)+ 345, Rt: 3.52 min.

2-[(E)-2-(4-methoxyphenyl)vinyl]benzo[g]quinazolin-4(3H)-one $^1$H NMR (300 MHz, DMSO-d$_6$) δ ppm 12. (bs, 1H); 8.80 (s, 1H); 8.19 (bs, 2H); 8.08 (d, 1H); 7.95 (d, 1H); 7.64 (d, 2H); 7.58 (t, 2H); 7.04 (d, 2H); 6.89 (d, 1H); 3.82 (s, 3H). LC-MS (ESI): m/z (M+H)+ 329, Rt: 4.03 min.

2-[(E)-2-(4-fluorophenyl)vinyl]benzo[g]quinazolin-4(3H)-one $^1$H NMR (300 MHz, DMSO-d$_6$) δ ppm 11.5 (bs, 1H); 8.82 (s, 1H); 8.31 (s, 1H); 8.13 (d, 1H); 8.10 (d, 1H); 7.92 (d, 1H); 7.75 (m, 2H); 7.67 (t, 1H); 7.60 (t, 1H); 7.32 (t, 2H); 7.01 (d, 1H). LC-MS (ESI): m/z (M+H)+ 317, Rt: 4.18 min.

2-[(E)-2-(4-chlorophenyl)vinyl]benzo[g]quinazolin-4(3H)-one $^1$H NMR (300 MHz, DMSO-d$_6$) δ ppm 11.5 (bs, 1H); 8.82 (s, 1H); 8.24 (s, 1H); 8.19 (d, 1H); 8.10 (d, 1H); 7.99 (d, 1H); 7.70 (m, 3H); 7.55 (m, 3H); 7.6 (d, 1H). LC-MS (ESI): m/z (M+H)+ 333, Rt: 4.53 min.

2-[(E)-2-(3,4-difluorophenyl)vinyl]benzo[g]quinazolin-4(3H)-one $^1$H NMR (300 MHz, DMSO-d$_6$) δ ppm 9.5 (bs, 1H); 8.84 (s, 1H); 8.32 (m, 2H); 8.10 (m, 1H); 7.94 (d, 1H); 7.82 (m, 1H); 7.62 (m, 4H); 7.06 (d, 1H). LC-MS (ESI): m/z (M+H)+ 335, Rt: 4.28 min.

7-chloro-2-[(E)-2-(4-methoxyphenyl)vinyl]quinazolin-4(3H)-one $^1$H NMR (300 MHz, DMSO-d$_6$) δ ppm 12.37 (bs, 1H); 8.09 (d, 1H); 7.92 (d, 1H); 7.68 (d, 1H); 7.62 (d, 2H); 7.48 (dd, 1H); 7.03 (d, 2H); 6.85 (d, 1H); 3.82 (s, 3H). LC-MS (ESI): m/z (M+H)+ 313, Rt: 4.14 min.

7-chloro-2-[(E)-2-(4-fluorophenyl)vinyl]quinazolin-4(3H)-one $^1$H NMR (300 MHz, DMSO-d$_6$) δ ppm 12.46 (bs, 1H); 8.9 (d, 1H); 7.96 (d, 1H); 7.73 (m, 3H); 7.51 (dd, 1H); 7.31 (t, 2H); 6.94 (d, 1H). LC-MS (ESI): m/z (M+H)+ 301, Rt: 4.22 min.

7-chloro-2-{(E)-2-[4-(dimethylamino)phenyl]vinyl}quinazolin-4(3H)-one $^1$H NMR (300 MHz, DMSO-d$_8$) δ ppm 12.23 (s, 1H); 8.06 (d, 1H); 7.87 (d, 1H); 7.63 (s, 1H); 7.45 (m, 3H); 6.72 (m, 3H); 2.99 (s, 6H). LC-MS (ESI): m/z (M+H)+ 301, Rt: 4.22 min.

6,8-dibromo-2-[(E)-2-(4-fluorophenyl)vinyl]quinazolin-4(3H)-one $^1$H NMR (300 MHz, DMSO-d$_6$) δ ppm 12.5 (bs, 1H); 8.21 (bs, 1H); 8.13 (bs, 1H); 7.92 (d, 1H); 7.73 (bs, 2H); 7.28 (t, 2H); 6.93 (t, 2H). LC-MS (ESI): m/z (M+H)+ 423, Rt: 4.93 min.

2-[(E)-2-(4-methoxyphenyl)vinyl]quinazolin-4(3H)-one $^1$H NMR (300 MHz, DMSO-d$_6$) δ ppm 12.25 (bs, NH); 8.09 (d, 1H); 7.90 (d, 1H); 7.79 (t, 1H); 7.66 (m, 3H); 7.45 (t, 1H); 7.02 (d, 2H); 6.87 (d, 1H); 3.78 (s, 3H). LC-MS (ESI): m/z (M+H)+ 279, Rt: 3.42 min.

2-[(E)-2-(4-fluorophenyl)vinyl]quinazolin-4(3H)-one $^1$H NMR (300 MHz, DMSO-d$_6$) δ ppm 12.33 (bs, 1H); 8.11 (d, 1H); 7.95 (d, 1H); 7.72 (m, 4H); 7.48 (t, 1H); 7.30 (t, 2H); 6.99 (d, 1H). LC-MS (ESI): m/z (M+H)+ 267, Rt: 3.57 min.

2-[(E)-2-(3,4-difluorophenyl)vinyl]quinazolin-4(3H)-one $^1$H NMR (300 MHz, DMSO-d$_8$) δ ppm 12.3 (bs, 1H); 8.12 (d, 1H); 7.92 (d, 1H); 7.80 (m, 2H); 7.68 (d, 1H); 7.512 (m, 3H); 7.04 (d, 1H). LC-MS (ESI): m/z (M+H)+ 285, Rt: 3.69 min.

2-[(E)-2-(3-fluorophenyl)vinyl]quinazolin-4(3H)-one $^1$H NMR (300 MHz, DMSO-d$_6$) δ ppm 12. (bs, 1H); 8.12 (d, 1H); 7.97 (d, 1H); 7.83 (t, 1H); 7.71 (d, 1H); 7.50 (m, 4H); 7.26 (t, 1H); 7.10 (d, 1H). LC-MS (ESI): m/z (M+H)+ 267, Rt: 3.61 min.

2-{(E)-2-[(4-(methylthio)phenyl]vinyl}quinazolin-4(3H)-one $^1$H NMR (300 MHz, DMSO-d$_6$) δ ppm 12.27 (bs, 1H); 8.13 (d, 1H); 7.90 (d, 1H); 7.79 (t, 1H); 7.63 (m, 3H); 7.38 (t, 1H); 7.13 (d, 2H); 6.92 (d, 1H); 2.51 (s, 3H). LC-MS (ESI): m/z (M+H)+ 295, Rt: 3.82 min.

2-[(E)-2-(3,4,5-trimethoxyphenyl)vinyl]quinazolin-4(3H)-one $^1$H NMR (300 MHz, DMSO-d$_8$) δ ppm 12.24 (bs, 1H); 8.10 (d, 1H); 7.90 (d, 1H); 7.80 (t, 1H); 7.65 (d, 1H); 7.47

(t, 1H); 7.03 (d, 1H); 7.00 (bs, 2H) 3.85 (s, 6H); 3.71 (s, 3H). LC-MS (ESI): m/z (M+H)+ 339, Rt: 3.30 min.

2-[(E)-2-(4-isopropylphenyl)vinyl]quinazolin-4(3H)-one

¹H NMR (300 MHz, DMSO-d₆) δ ppm 12.32 (bs, 1H); 8.10 (d, 1H); 7.93 (d, 1H); 7.80 (t, 1H); 7.67 (d, 1H); 7.59 (d, 2H); 7.47 (t, 1H); 7.34 (d, 2H); 7.00 (d, 1H); 2.90 (m, 1H); 1.23 (d, 6H). LC-MS (ESI): m/z (M+H)+ 291, Rt: 4.31 min.

2-{(E)-2-[4-(methylsulfonyl)phenyl]vinyl}quinazolin-4(3H)-one

¹H NMR (300 MHz, DMSO-d₆) δ ppm 12.42 (bs, 1H); 8.15 (d, 1H); 8.14-7.13 (m, 5H); 7.83 (t, 1H); 7.71 (d, 1H); 7.52 (t, 1H); 7.19 (d, 1H); 3.26 (s, 3H). LC-MS (ESI): m/z (M+H)+ 327, Rt: 2.96 min.

2-[(E)-2-(2-thienyl)vinyl]quinazolin-4(3H)-one

¹H NMR (300 MHz, DMSO-d₆) δ ppm 12.30 (bs, 1H); 8.12 (d, 1H); 8.10 (s, 1H); 7.79 (t, 1H); 7.66 (m, 2H); 7.46 (m, 2H); 7.16 (bs, 1H); 6.78 (d, 1H). LC-MS (ESI): m/z (M+H)+ 255, Rt: 3.36 min.

6-chloro-2-[(E)-2-(2-thienyl)vinyl]quinazolin-4(3H)-one

¹H NMR (300 MHz, DMSO-d₆) δ ppm 12.40 (bs, 1H); 8.12 (d, 1H); 8.02 (s, 1H); 7.81 (d, 1H); 7.68 (m, 2H); 7.49 (bs, 1H); 7.16 (bs, 1H); 6.72 (d, 1H). LC-MS (ESI): m/z (M+H)+ 289, Rt: 3.99 min.

6-bromo-2-[(E)-2-(2-thienyl)vinyl]quinazolin-4(3H)-one

¹H NMR (300 MHz, DMSO-d₆) δ ppm 12.41 (bs, 1H); 8.13 (d, 1H); 8.15 (s, 1H); 7.92 (d, 1H); 7.70 (d, 1H); 7.59 (d, 1H); 7.49 (d, 1H); 7.16 (dd, 1H); 6.72 (d, 1H). LC-MS (ESI): m/z (M+H)+ 333, Rt: 4.08 min.

2-[(E)-2-(2-thienyl)vinyl]benzo[g]quinazolin-4(3H)-one

¹H NMR (300 MHz, DMSO-d₆) δ ppm 12.06 (bs, 1H); 8.80 (s, 1H); 8.14 (m, 4H); 7.67 (m, 2H); 7.56 (t, 1H); 7.50 (bs, 1H); 7.16 (t, 1H); 6.77 (d, 1H). LC-MS (ESI): m/z (M+H)+ 305, Rt: 4.04 min.

Step C: Preparation of substituted 4-chloro-2-[(E)-2-phenylvinyl]quinazoline and 4-chloro-2-[(E)-2-(2-thienyl)vinyl]quinazoline Scheme 3

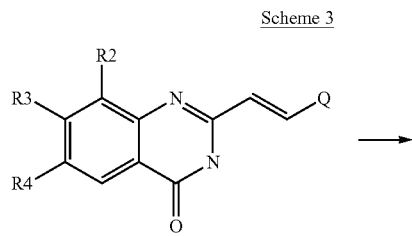

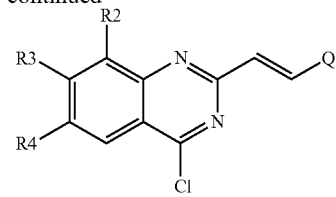

The starting material was dissolved in phosphorous oxychloride and stirred at 90° C. overnight. The reaction mixture was cooled to room temperature and the phosphorous oxychloride was evaporated. The crude product was dissolved in chloroform, washed with cold water and with 10% sodium hydrogen carbonate solution. The organic layer was stirred over magnesium sulfate 1 hour, was evaporated and dried under vacuum. Due to the instability of the intermediates the purity was checked only by TLC.

Step D: Preparation of substituted 2-[(E)-2-phenylvinyl]quinazolin-4-amines and 2-[(E)-2-(2-thienyl)vinyl]quinazolin-4-amine Scheme 4

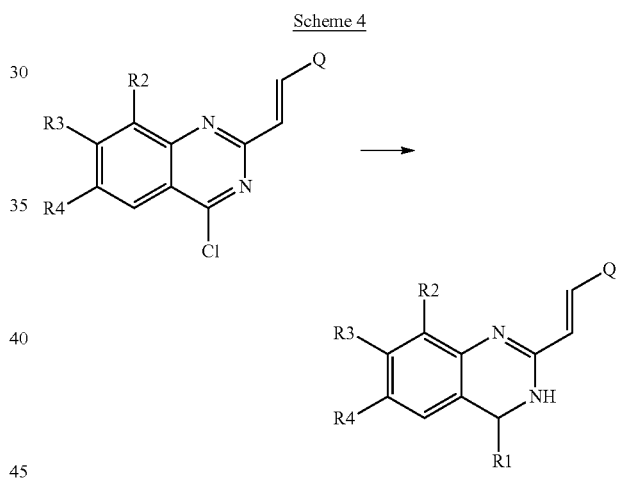

N'-{6-chloro-2-[(E)-2-(4-methoxyphenyl)vinyl]quinazolin-4-yl}-N,N-dimethylpropane-1,3-diamine 0.87 g (2.62 mmol) 4,6-dichloro-2-[(E)-2-(4-methoxyphenyl)vinyl]quinazoline was solved in 10 ml abs. dioxane. 0.45 ml (2.62 mmol) diisopropyl-ethylamine and 0.36 ml (2.88 mmol) N,N-dimethylpropane-1,3-diamine were given to this solution. The reaction was stirred 12 hours under Argon atmosphere at 80° C. The solvent was evaporated under vacuum, and the product was purified by column chromatography or preparative TLC. The product was prepared as oxalate salt.

Preparation of other 2-[(E)-2-phenylvinyl]quinazolin-4-amines and 2-[(E)-2-(2-thienyl)vinyl]quinazolin-4-amine derivatives were carried out with the same method.

Yield: 0.35 g (27%)

¹H NMR (300 MHz, DMSO-d₆) δ ppm. LC-MS (ESI): m/z (M+H)+ 397, Rt: 0.46 min., 1.95 min., 2.13 min.

TABLE 1

| Example | Structure | Name | Formula | Salt |
|---|---|---|---|---|
| 1 | 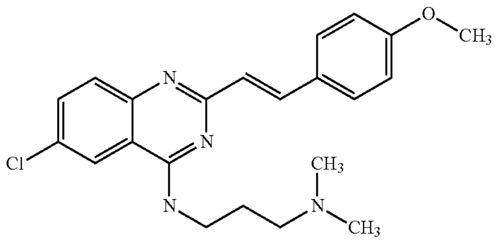 [SMILES: COc1ccc(/C=C/c2nc(NCCCN(C)C)c3cc(Cl)ccc3n2)cc1] | N'-{6-chloro-2-[(E)-2-(4-methoxyphenyl)vinyl]quinazolin-4-yl}-N,N-dimethylpropane-1,3-diamine | C22H25ClN4O | Oxalate |
| 2 | 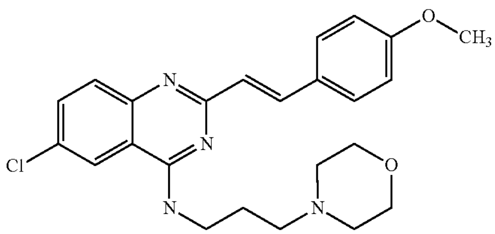 [SMILES: COc1ccc(/C=C/c2nc(NCCCN3CCOCC3)c3cc(Cl)ccc3n2)cc1] | 6-chloro-2-[(E)-2-(4-methoxyphenyl)vinyl]-N-(3-morpholin-4-ylpropyl)quinazolin-4-amine | C24H27ClN4O2 | |
| 3 | 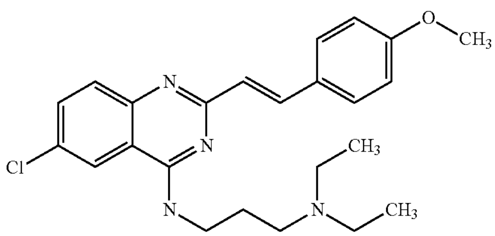 [SMILES: CCN(CC)CCCNc1nc(/C=C/c2ccc(OC)cc2)nc2ccc(Cl)cc12] | N'-{6-chloro-2-[(E)-2-(4-methoxyphenyl)vinyl]quinazolin-4-yl}-N,N-diethylpropane-1,3-diamine | C24H29ClN4O | HCl |
| 4 | 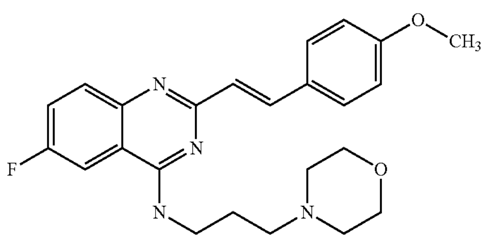 [SMILES: COc1ccc(/C=C/c2nc(NCCCN3CCOCC3)c3cc(F)ccc3n2)cc1] | 6-fluoro-2-[(E)-2-(4-methoxyphenyl)vinyl]-N-(3-morpholin-4-ylpropyl)quinazolin-4-amine | C24H27FN4O2 | |
| 5 | 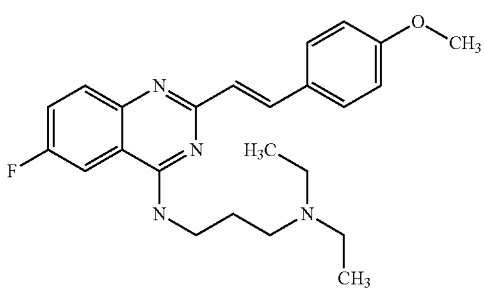 [SMILES: CCN(CC)CCCNc1nc(/C=C/c2ccc(OC)cc2)nc2ccc(F)cc12] | N,N-diethyl-N'-{6-fluoro-2-[(E)-2-(4-methoxyphenyl)vinyl]quinazolin-4-yl}propane-1,3-diamine | C24H29FN4O | |
| 6 | 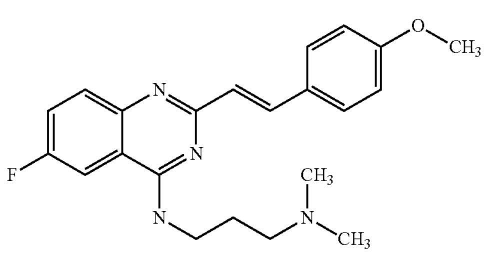 [SMILES: COc1ccc(/C=C/c2nc(NCCCN(C)C)c3cc(F)ccc3n2)cc1] | N'-{6-bromo-2-[(E)-2-(4-methoxyphenyl)vinyl]quinazolin-4-yl}-N,N-dimethylpropane-1,3-diamine | C22H25FN4O | |

TABLE 1-continued

Identification of the prepared compounds.

| Example | Structure | Name | Formula | Salt |
|---|---|---|---|---|
| 7 | 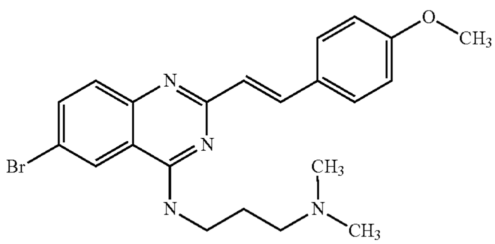 [SMILES: COc1ccc(/C=C/c2nc(NCCCN(C)C)c3cc(Br)ccc3n2)cc1] | N'-{6-bromo-2-[(E)-2-(4-methoxyphenyl)vinyl]quinazolin-4-yl}-N,N-dimethylpropane-1,3-diamine | C22H25BrN4O | Oxalate |
| 8 | 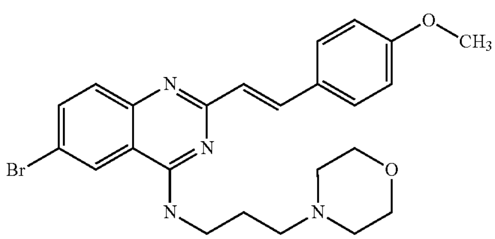 [SMILES: COc1ccc(/C=C/c2nc(NCCCN3CCOCC3)c3cc(Br)ccc3n2)cc1] | 6-bromo-2-[(E)-2-(4-methoxyphenyl)vinyl]-N-(3-morpholin-4-ylpropyl)quinazolin-4-amine | C24H27BrN4O2 | |
| 9 | 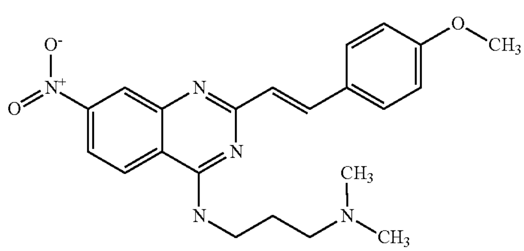 [SMILES: COc1ccc(/C=C/c2nc(NCCCN(C)C)c3ccc([N+](=O)[O-])cc3n2)cc1] | N'-{2-[(E)-2-(4-methoxyphenyl)vinyl]-7-nitroquinazolin-4-yl}-N,N-dimethylpropane-1,3-diamine | C22H25N5O3 | |
| 10 | 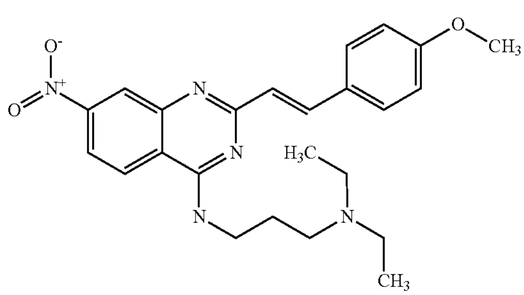 [SMILES: CCN(CC)CCCNc1nc(/C=C/c2ccc(OC)cc2)nc2cc([N+](=O)[O-])ccc12] | N,N-diethyl-N'-{2-[(E)-2-(4-methoxyphenyl)vinyl]-7-nitroquinazolin-4-yl}propane-1,3-diamine | C24H29N5O3 | |
| 11 | 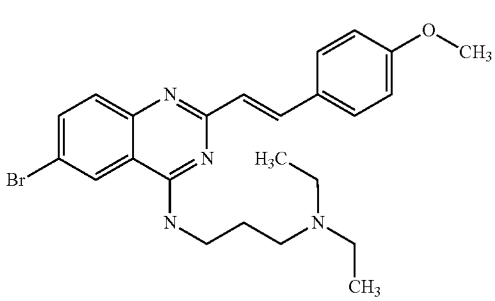 [SMILES: CCN(CC)CCCNc1nc(/C=C/c2ccc(OC)cc2)nc2ccc(Br)cc12] | N'-{6-bromo-2-[(E)-2-(4-methoxyphenyl)vinyl]quinazolin-4-yl}-N,N-diethylpropane-1,3-diamine | C24H29BrN4O | |

TABLE 1-continued

Identification of the prepared compounds.

| Example | Structure | Name | Formula | Salt |
|---|---|---|---|---|
| 12 | 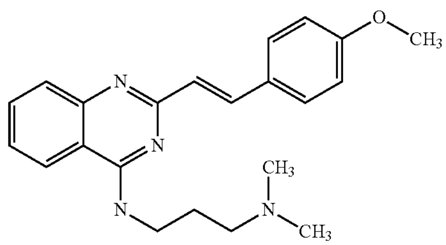 [SMILES: COc1ccc(/C=C/c2nc(NCCCN(C)C)c3ccccc3n2)cc1] | N'-{2-[(E)-2-(4-methoxyphenyl)vinyl]quinazolin-4-yl}-N,N-dimethylpropane-1,3-diamine | C22H26N4O | Fumarate |
| 13 | 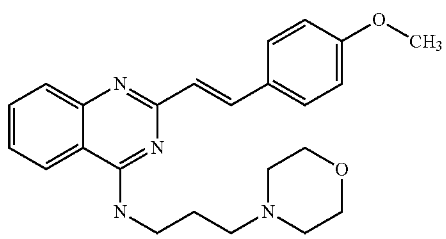 [SMILES: COc1ccc(/C=C/c2nc(NCCCN3CCOCC3)c3ccccc3n2)cc1] | 2-[(E)-2-(4-methoxyphenyl)vinyl]-N-(3-morpholin-4-ylpropyl)quinazolin-4-amine | C24H28N4O2 | Oxalate |
| 14 | 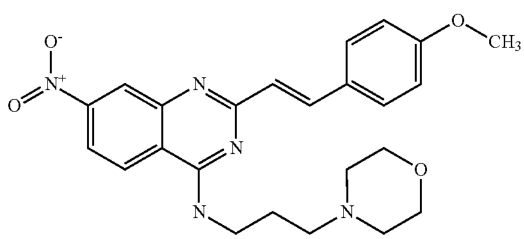 [SMILES: COc1ccc(/C=C/c2nc(NCCCN3CCOCC3)c3ccc([N+](=O)[O-])cc3n2)cc1] | 2-[(E)-2-(4-methoxyphenyl)vinyl]-N-(3-morpholin-4-ylpropyl)-7-nitroquinazolin-4-amine | C24H27N5O4 | Oxalate |
| 15 | 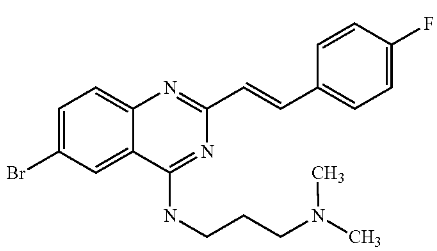 [SMILES: CN(C)CCCNc1nc(/C=C/c2ccc(F)cc2)nc2ccc(Br)cc12] | N'-{6-bromo-2-[(E)-2-(4-fluorophenyl)vinyl]quinazolin-4-yl}-N,N-dimethylpropane-1,3-diamine | C21H22BrFN4 | |
| 16 | 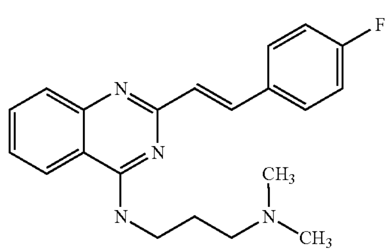 [SMILES: CN(C)CCCNc1nc(/C=C/c2ccc(F)cc2)nc2ccccc12] | N'-{2-[(E)-2-(4-fluorophenyl)vinyl]quinazolin-4-yl}-N,N-dimethylpropane-1,3-diamine | C21H23FN4 | |
| 17 | 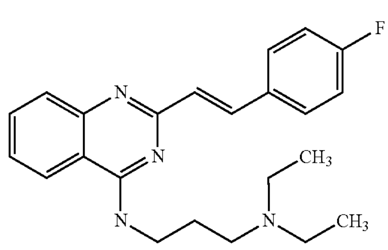 [SMILES: CCN(CC)CCCNc1nc(/C=C/c2ccc(F)cc2)nc2ccccc12] | N,N-diethyl-N'-{2-[(E)-2-(4-fluorophenyl)vinyl]quinazolin-4-yl}propane-1,3-diamine | C23H27FN4 | |

TABLE 1-continued

Identification of the prepared compounds.

| Example | Structure | Name | Formula | Salt |
|---|---|---|---|---|
| 18 | 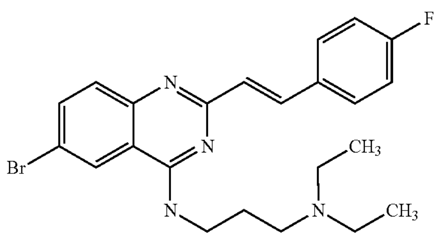 [SMILES: CCN(CC)CCCNc1nc(/C=C/c2ccc(F)cc2)nc2ccc(Br)cc12] | N'-{6-bromo-2-[(E)-2-(4-fluorophenyl)vinyl]quinazolin-4-yl}-N,N-diethylpropane-1,3-diamine | C23H26BrFN4 | |
| 19 | 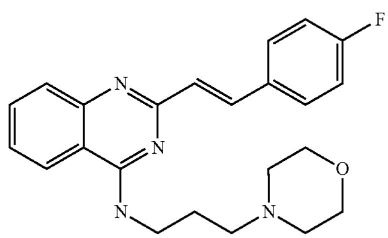 [SMILES: Fc1ccc(/C=C/c2nc(NCCCN3CCOCC3)c3ccccc3n2)cc1] | 2-[(E)-2-(4-fluorophenyl)vinyl]-N-(3-morpholin-4-ylpropyl)quinazolin-4-amine | C23H25FN4O | Oxalate |
| 20 | 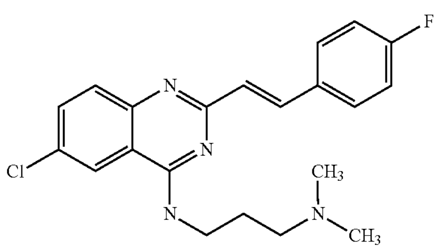 [SMILES: CN(C)CCCNc1nc(/C=C/c2ccc(F)cc2)nc2ccc(Cl)cc12] | N'-{6-chloro-2-[(E)-2-(4-fluorophenyl)vinyl]quinazolin-4-yl}-N,N-dimethylpropane-1,3-diamine | C21H22ClFN4 | Fumarate |
| 21 | 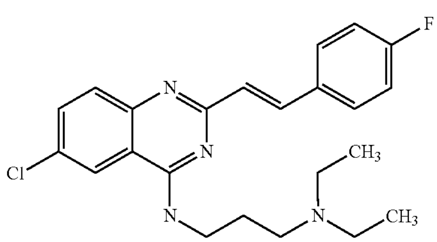 [SMILES: CCN(CC)CCCNc1nc(/C=C/c2ccc(F)cc2)nc2ccc(Cl)cc12] | N'-{6-chloro-2-[(E)-2-(4-fluorophenyl)vinyl]quinazolin-4-yl}-N,N-diethylpropane-1,3-diamine | C23H26ClFN4 | |
| 22 | 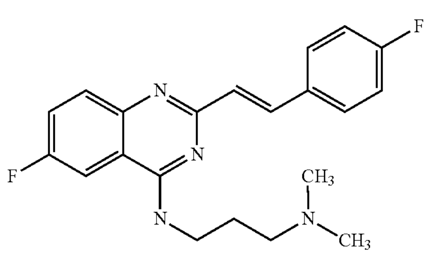 [SMILES: CN(C)CCCNc1nc(/C=C/c2ccc(F)cc2)nc2ccc(F)cc12] | N'-{6-fluoro-2-[(E)-2-(4-fluorophenyl)vinyl]quinazolin-4-yl}-N,N-dimethylpropane-1,3-diamine | C21H22F2N4 | |
| 23 | 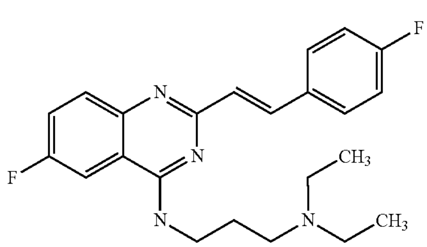 [SMILES: CCN(CC)CCCNc1nc(/C=C/c2ccc(F)cc2)nc2ccc(F)cc12] | N,N-diethyl-N'-{6-fluoro-2-[(E)-2-(4-fluorophenyl)vinyl]quinazolin-4-yl}propane-1,3-diamine | C23H26F2N4 | HCl |

TABLE 1-continued

Identification of the prepared compounds.

| Example | Structure | Name | Formula | Salt |
|---|---|---|---|---|
| 24 | 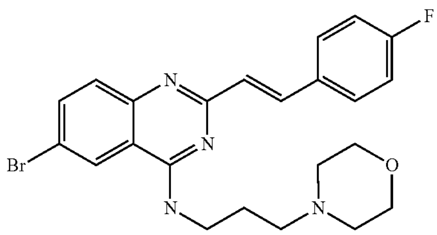 [SMILES: Fc1ccc(/C=C/c2nc(NCCCN3CCOCC3)c3cc(Br)ccc3n2)cc1] | 6-bromo-2-[(E)-2-(4-fluorophenyl)vinyl]-N-(3-morpholin-4-ylpropyl)quinazolin-4-amine | C23H24BrFN4O | |
| 25 | 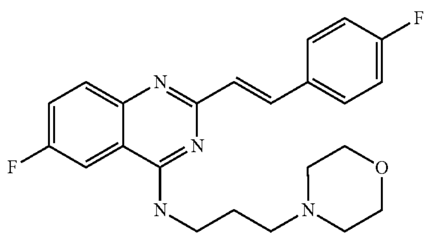 [SMILES: Fc1ccc(/C=C/c2nc(NCCCN3CCOCC3)c3cc(F)ccc3n2)cc1] | 6-fluoro-2-[(E)-2-(4-fluorophenyl)vinyl]-N-(3-morpholin-4-ylpropyl)quinazolin-4-amine | C23H24F2N4O | |
| 26 | 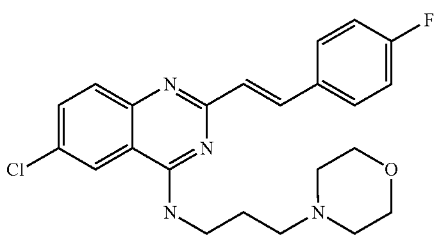 [SMILES: Fc1ccc(/C=C/c2nc(NCCCN3CCOCC3)c3cc(Cl)ccc3n2)cc1] | 6-chloro-2-[(E)-2-(4-fluorophenyl)vinyl]-N-(3-morpholin-4-ylpropyl)quinazolin-4-amine | C23H24ClFN4O | |
| 27 | 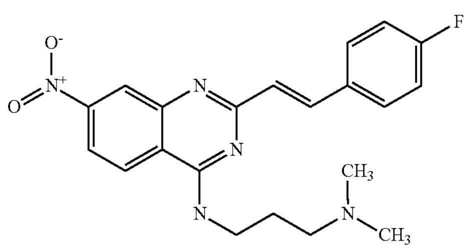 [SMILES: CN(C)CCCNc1nc(/C=C/c2ccc(F)cc2)nc2cc([N+](=O)[O-])ccc12] | N'-{2-[(E)-2-(4-fluorophenyl)vinyl]-7-nitroquinazolin-4-yl}-N,N-dimethylpropane-1,3-diamine | C21H22FN5O2 | |
| 28 | 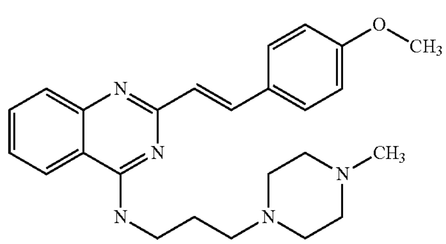 [SMILES: COc1ccc(/C=C/c2nc(NCCCN3CCN(C)CC3)c3ccccc3n2)cc1] | 2-[(E)-2-(4-methoxyphenyl)vinyl]-N-[3-(4-methylpiperazin-1-yl)propyl]quinazolin-4-amine | C25H31N5O | Oxalate |
| 29 | 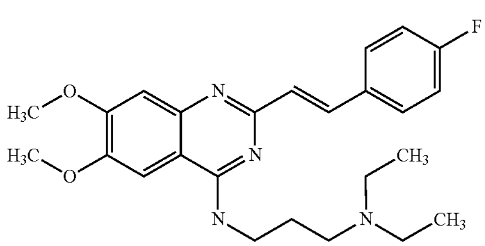 [SMILES: CCN(CC)CCCNc1nc(/C=C/c2ccc(F)cc2)nc2cc(OC)c(OC)cc12] | N,N-diethyl-N'-{2-[(E)-2-(4-fluorophenyl)vinyl]-6,7-dimethoxyquinazolin-4-yl}propane-1,3-diamine | C25H31FN4O2 | Oxalate |

TABLE 1-continued

Identification of the prepared compounds.

| Example | Structure | Name | Formula | Salt |
|---|---|---|---|---|
| 30 | 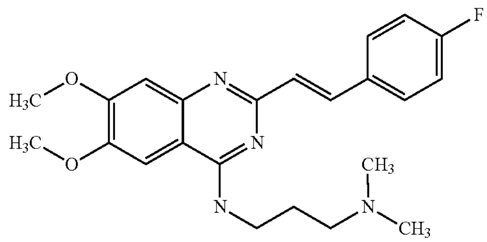 [SMILES: COc1cc2nc(/C=C/c3ccc(F)cc3)nc(NCCCN(C)C)c2cc1OC] | N'-{2-[(E)-2-(4-fluorophenyl)vinyl]-6,7-dimethoxyquinazolin-4-yl}-N,N-dimethylpropane-1,3-diamine | C23H27FN4O2 | Oxalate |
| 31 | 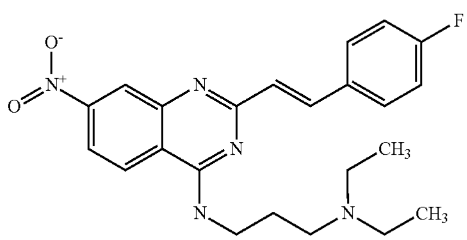 [SMILES: CCN(CC)CCCNc1nc(/C=C/c2ccc(F)cc2)nc2cc([N+](=O)[O-])ccc12] | N,N-diethyl-N'-{2-[(E)-2-(4-fluorophenyl)vinyl]-7-nitroquinazolin-4-yl}propane-1,3-diamine | C23H26FN5O2 | Oxalate |
| 32 | 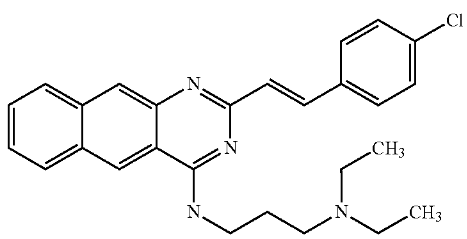 [SMILES: CCN(CC)CCCNc1nc(/C=C/c2ccc(Cl)cc2)nc2cc3ccccc3cc12] | N'-{2-[(E)-2-(4-chlorophenyl)vinyl]benzo[g]quinazolin-4-yl}-N,N-diethylpropane-1,3-diamine | C27H29ClN4 | Oxalate |
| 33 | 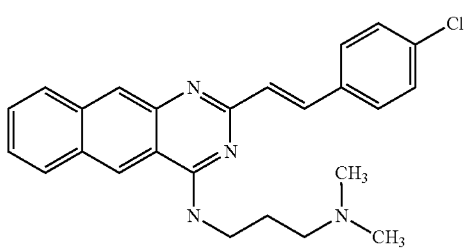 [SMILES: CN(C)CCCNc1nc(/C=C/c2ccc(Cl)cc2)nc2cc3ccccc3cc12] | N'-{2-[(E)-2-(4-chlorophenyl)vinyl]benzo[g]quinazolin-4-yl}-N,N-dimethylpropane-1,3-diamine | C25H25ClN4 | Oxalate |
| 34 | 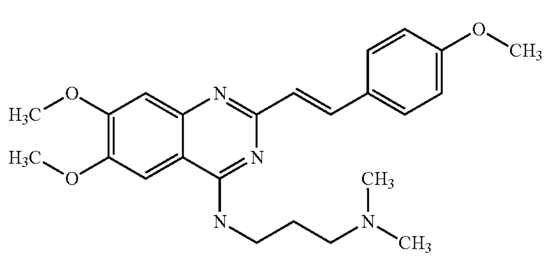 | N'-{6,7-dimethoxy-2-[(E)-2-(4-methoxphenyl)vinyl]quinazolin-4-yl}-N,N-dimethylpropane-1,3-diamine | C24H30N4O3 | Citrate |
| 35 | 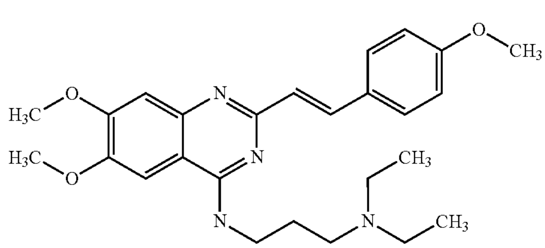 | N'-{6,7-dimethoxy-2-[(E)-2-(4-methoxyphenyl)vinyl]quinazolin-4-yl}-N,N-diethylpropane-1,3-diamine | C26H34N4O3 | Citrate |

TABLE 1-continued

Identification of the prepared compounds.

| Example | Structure | Name | Formula | Salt |
|---|---|---|---|---|
| 36 | 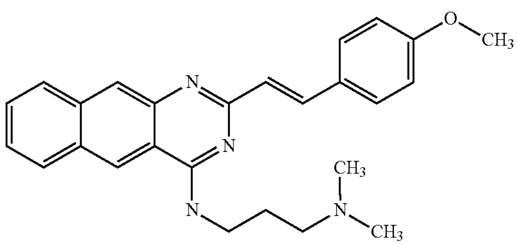 [SMILES: COc1ccc(/C=C/c2nc(NCCCN(C)C)c3cc4ccccc4cc3n2)cc1] | N'-{2-[(E)-2-(4-methoxyphenyl)vinyl]benzo[g]quinazolin-4-yl}-N,N-dimethylpropane-1,3-diamine | C26H28N4O | Citrate |
| 37 | 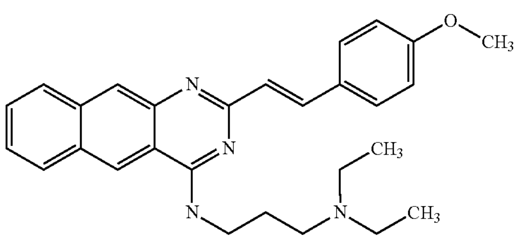 [SMILES: CCN(CC)CCCNc1nc(/C=C/c2ccc(OC)cc2)nc2cc3ccccc3cc12] | N,N-diethyl-N'-{2-[(E)-2-(4-methoxyphenyl)vinyl]benzo[g]quinazolin-4-yl}propane-1,3-diamine | C28H32N4O | Citrate |
| 38 | 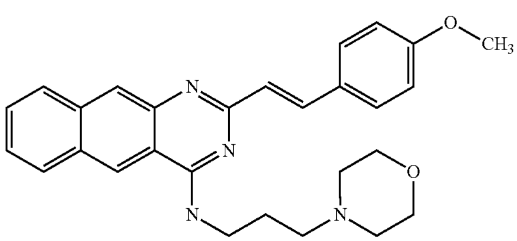 [SMILES: COc1ccc(/C=C/c2nc(NCCCN3CCOCC3)c3cc4ccccc4cc3n2)cc1] | 2-[(E)-2-(4-methoxyphenyl)vinyl]-N-(3-morpholin-4-ylpropyl)benzo[g]quinazolin-4-amine | C28H30N4O2 | Citrate |
| 39 | 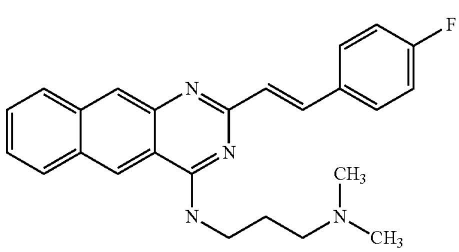 [SMILES: CN(C)CCCNc1nc(/C=C/c2ccc(F)cc2)nc2cc3ccccc3cc12] | N'-{2-[(E)-2-(4-fluorophenyl)vinyl]benzo[g]quinazolin-4-yl}-N,N-dimethylpropane-1,3-diamine | C25H25FN4 | Fumarate |
| 40 | 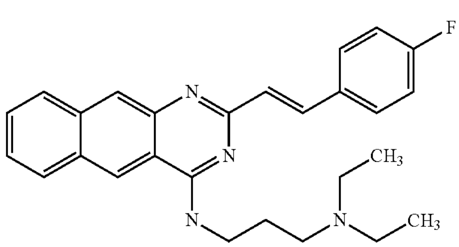 [SMILES: CCN(CC)CCCNc1nc(/C=C/c2ccc(F)cc2)nc2cc3ccccc3cc12] | N,N-diethyl-N'-{2-[(E)-2-(4-fluorophenyl)vinyl]benzo[g]quinazolin-4-yl}propane-1,3-diamine | C27H29FN4 | Citrate |
| 41 | 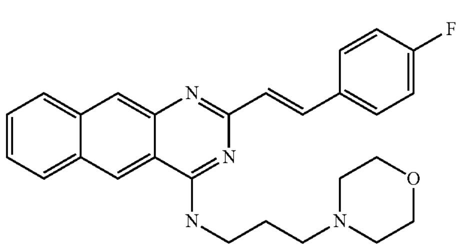 [SMILES: Fc1ccc(/C=C/c2nc(NCCCN3CCOCC3)c3cc4ccccc4cc3n2)cc1] | 2-[(E)-2-(4-fluorophenyl)vinyl]-N-(3-morpholin-4-ylpropyl)benzo[g]quinazolin-4-amine | C27H27FN4O | Oxalate |

TABLE 1-continued

Identification of the prepared compounds.

| Example | Structure | Name | Formula | Salt |
|---|---|---|---|---|
| 42 | 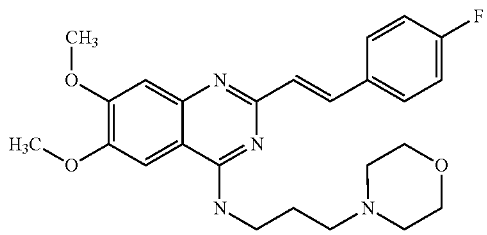 [SMILES: COc1cc2nc(/C=C/c3ccc(F)cc3)nc(NCCCN3CCOCC3)c2cc1OC] | 2-[(E)-2-(4-fluorophenyl)vinyl]-6,7-dimethoxy-N-(3-morpholin-4-ylpropyl)quinazolin-4-amine | C25H29FN4O3 | |
| 43 | 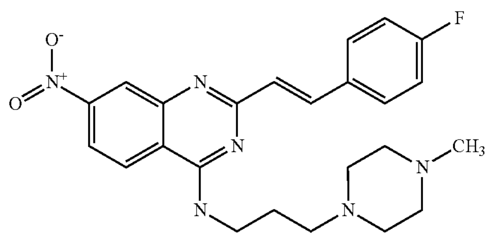 [SMILES: CN1CCN(CCCNc2nc(/C=C/c3ccc(F)cc3)nc3cc([N+](=O)[O-])ccc23)CC1] | 2-[(E)-2-(4-fluorophenyl)vinyl]-N-[3-(4-methylpiperazin-1-yl)propyl]-7-nitroquinazolin-4-amine | C24H27FN6O2 | |
| 44 | 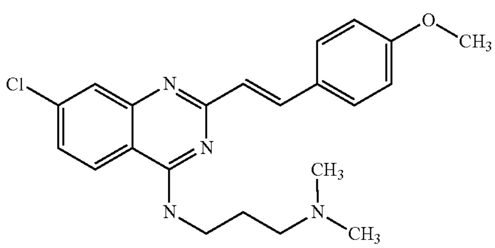 [SMILES: COc1ccc(/C=C/c2nc(NCCCN(C)C)c3ccc(Cl)cc3n2)cc1] | N'-{7-chloro-2-[(E)-2-(4-methoxyphenyl)vinyl]quinazolin-4-yl}-N,N-dimethylpropane-1,3-diamine | C22H25ClN4O | |
| 45 | 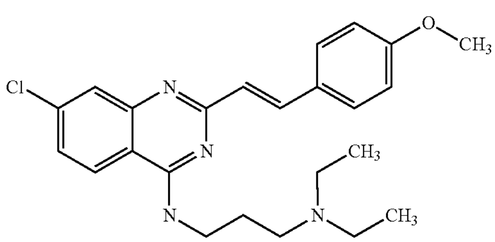 [SMILES: CCN(CC)CCCNc1nc(/C=C/c2ccc(OC)cc2)nc2cc(Cl)ccc12] | N'-{7-chloro-2-[(E)-2-(4-methoxyphenyl)vinyl]quinazolin-4-yl}-N,N-dimethylpropane-1,3-diamine | C24H29ClN4O | |
| 46 | 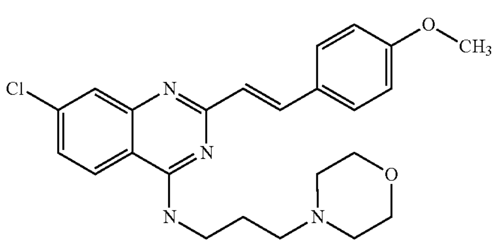 [SMILES: COc1ccc(/C=C/c2nc(NCCCN3CCOCC3)c3ccc(Cl)cc3n2)cc1] | 7-chloro-2-[(E)-2-(4-methoxyphenyl)vinyl]-N-(3-morpholin-4-ylpropyl)quinazolin-4-amine | C24H27ClN4O2 | |
| 47 | 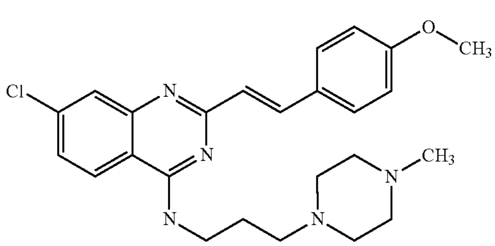 [SMILES: COc1ccc(/C=C/c2nc(NCCCN3CCN(C)CC3)c3ccc(Cl)cc3n2)cc1] | 7-chloro-2-[(E)-2-(4-methoxyphenyl)vinyl]-N-[3-(4-methylpiperazin-1-yl)propyl]quinazolin-4-amine | C25H30ClN5O | |

TABLE 1-continued

Identification of the prepared compounds.

| Example | Structure | Name | Formula | Salt |
|---|---|---|---|---|
| 48 | 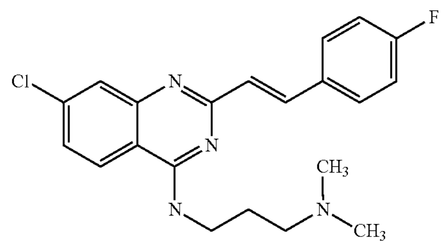 [SMILES: CN(C)CCCNc1nc(/C=C/c2ccc(F)cc2)nc2cc(Cl)ccc12] | N'-{7-chloro-2-[(E)-2-(4-fluorophenyl)vinyl]quinazolin-4-yl}-N,N-dimethylpropane-1,3-diamine | C21H22ClFN4 | |
| 49 | 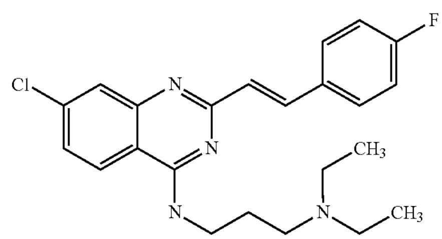 [SMILES: CCN(CC)CCCNc1nc(/C=C/c2ccc(F)cc2)nc2cc(Cl)ccc12] | N'-{7-chloro-2-[(E)-2-(4-fluorophenyl)vinyl]quinazolin-4-yl}-N,N-diethylpropane-1,3-diamine | C23H26ClFN4 | |
| 50 | 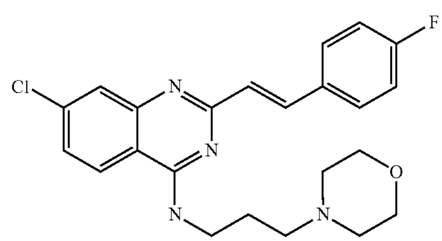 [SMILES: Fc1ccc(/C=C/c2nc(NCCCN3CCOCC3)c3ccc(Cl)cc3n2)cc1] | 7-chloro-2-[(E)-2-(4-fluorophenyl)vinyl]-N-(3-morpholin-4-ylpropyl)quinazolin-4-amine | C23H24ClFN4O | |
| 51 | 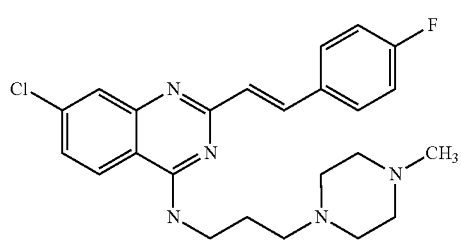 [SMILES: CN1CCN(CCCNc2nc(/C=C/c3ccc(F)cc3)nc3cc(Cl)ccc23)CC1] | 7-chloro-2-[(E)-2-(4-fluorophenyl)vinyl]-N-[3-(4-methylpiperazin-1-yl)propyl]quinazolin-4-amine | C24H27ClFN5 | |
| 52 | 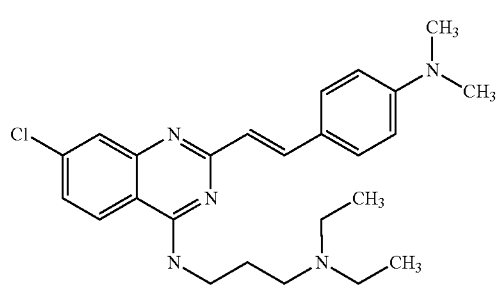 [SMILES: CCN(CC)CCCNc1nc(/C=C/c2ccc(N(C)C)cc2)nc2cc(Cl)ccc12] | N'-(7-chloro-2-{(E)-2-[4-(dimethylamino)phenyl]vinyl}quinazolin-4-yl)-N,N-diethylpropane-1,3-diamine | C25H32ClN5 | |

TABLE 1-continued

Identification of the prepared compounds.

| Example | Structure | Name | Formula | Salt |
|---|---|---|---|---|
| 53 | 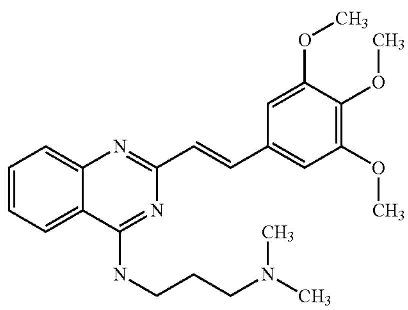 [SMILES: COc1cc(/C=C/c2nc(NCCCN(C)C)c3ccccc3n2)cc(OC)c1OC] | N,N-dimethyl-N'-{2-[(E)-2-(3,4,5-trimethoxyphenyl)vinyl]quinazolin-4-yl}propane-1,3-diamine | C24H30N4O3 | |
| 54 | 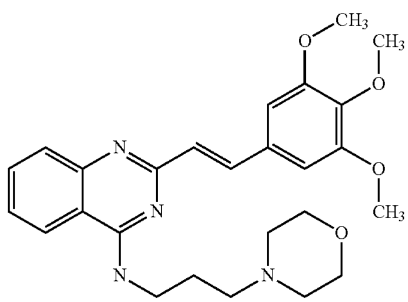 [SMILES: COc1cc(/C=C/c2nc(NCCCN3CCOCC3)c3ccccc3n2)cc(OC)c1OC] | N-(3-morpholin-4-ylpropyl)-2-[(E)-2-(3,4,5-trimethoxyphenyl)vinyl]quinazolin-4-amine | C26H32N4O4 | Citrate |
| 55 | 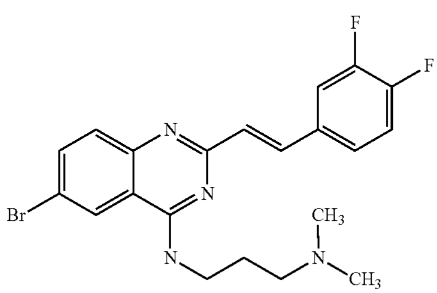 [SMILES: CN(C)CCCNc1nc(/C=C/c2ccc(F)c(F)c2)nc2ccc(Br)cc12] | N'-{6-bromo-2-[(E)-2-(3,4-difluorophenyl)vinyl]quinazolin-4-yl}-N,N-dimethylpropane-1,3-diamine | C21H21BrF2N4 | |
| 56 | 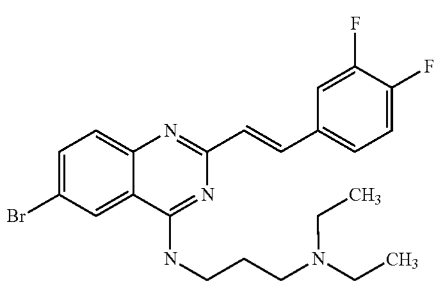 [SMILES: CCN(CC)CCCNc1nc(/C=C/c2ccc(F)c(F)c2)nc2ccc(Br)cc12] | N'-{6-bromo-2-[(E)-2-(3,4-difluorophenyl)vinyl]quinazolin-4-yl}-N,N-diethylpropane-1,3-diamine | C23H25BrF2N4 | |
| 57 | 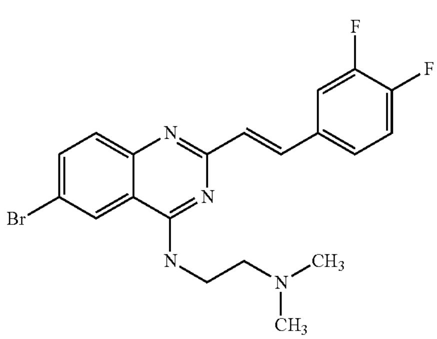 [SMILES: CN(C)CCNc1nc(/C=C/c2ccc(F)c(F)c2)nc2ccc(Br)cc12] | N'-{6-bromo-2-[(E)-2-(3,4-difluorophenyl)vinyl]quinazolin-4-yl}-N,N-dimethylethane-1,2-diamine | C20H19BrF2N4 | |

TABLE 1-continued

Identification of the prepared compounds.

| Example | Structure | Name | Formula | Salt |
|---|---|---|---|---|
| 58 | 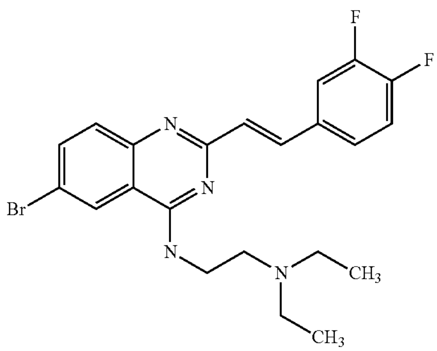 [SMILES: CCN(CC)CCNc1nc(/C=C/c2ccc(F)c(F)c2)nc2ccc(Br)cc12] | N'-{6-bromo-2-[(E)-2-(3,4-difluorophenyl)vinyl]quinazolin-4-yl}-N,N-diethylethane-1,2-diamine | C22H23BrF2N4 | |
| 59 | 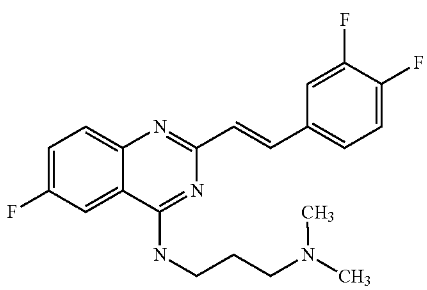 [SMILES: CN(C)CCCNc1nc(/C=C/c2ccc(F)c(F)c2)nc2ccc(F)cc12] | N'-{2-[(E)-2-(3,4-difluorophenyl)vinyl]-6-fluoroquinazolin-4-yl}-N,N-dimethylpropane-1,3-diamine | C21H21F3N4 | |
| 60 | 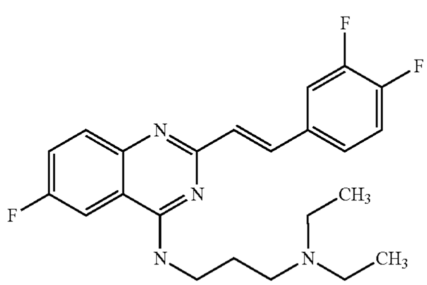 [SMILES: CCN(CC)CCCNc1nc(/C=C/c2ccc(F)c(F)c2)nc2ccc(F)cc12] | N'-{2-[(E)-2-(3,4-difluorophenyl)vinyl]-6-fluoroquinazolin-4-yl}-N,N-diethylpropane-1,3-diamine | C23H25F3N4 | |
| 61 | 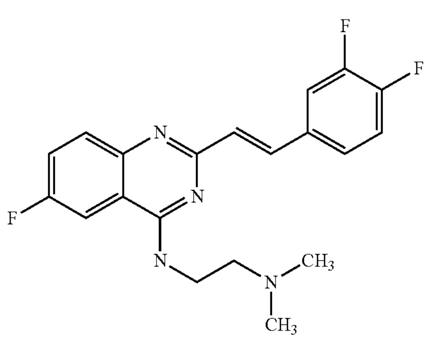 [SMILES: CN(C)CCNc1nc(/C=C/c2ccc(F)c(F)c2)nc2ccc(F)cc12] | N'-{2-[(E)-2-(3,4-difluorophenyl)vinyl]-6-fluoroquinazolin-4-yl}-N,N-dimethylethane-1,2-diamine | C20H19F3N4 | |

TABLE 1-continued

Identification of the prepared compounds.

| Example | Structure | Name | Formula | Salt |
|---|---|---|---|---|
| 62 | 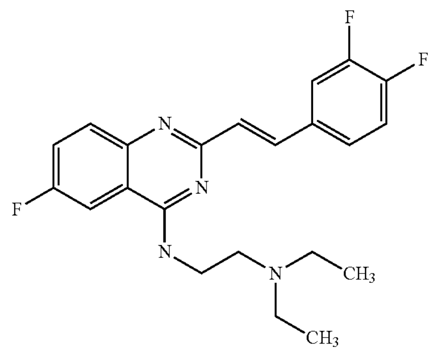 [SMILES: CCN(CC)CCNc1nc(/C=C/c2ccc(F)c(F)c2)nc2ccc(F)cc12] | N'-{2-[(E)-2-(3,4-difluorophenyl)vinyl]-6-fluoroquinazolin-4-yl}-N,N-diethylethane-1,2-diamine | C22H23F3N4 | |
| 63 | 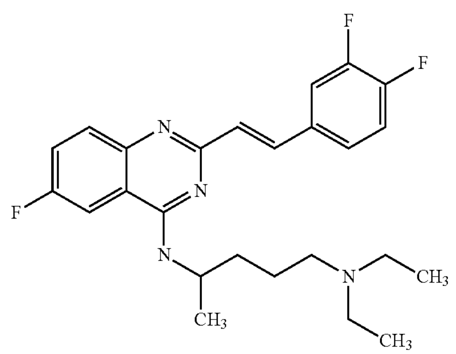 [SMILES: CCN(CC)CCCC(C)Nc1nc(/C=C/c2ccc(F)c(F)c2)nc2ccc(F)cc12] | N4-{2-[(E)-2-(3,4-difluorophenyl)vinyl]-6-fluoroquinazolin-4-yl}-N1,N1-diethylpentane-1,4-diamine | C25H29F3N4 | |
| 64 | 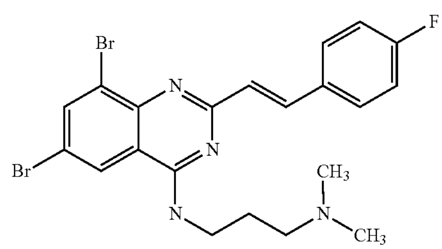 [SMILES: CN(C)CCCNc1nc(/C=C/c2ccc(F)cc2)nc2c(Br)cc(Br)cc12] | N'-{6,8-dibromo-2-[(E)-2-(4-fluorophenyl)vinyl]quinazolin-4-yl}-N,N-dimethylpropane-1,3-diamine | C21H21Br2FN4 | |
| 65 | 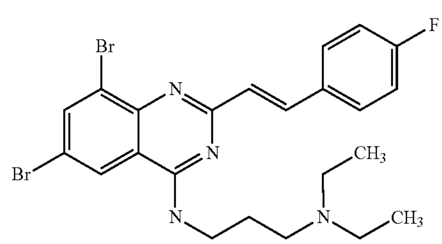 [SMILES: CCN(CC)CCCNc1nc(/C=C/c2ccc(F)cc2)nc2c(Br)cc(Br)cc12] | N'-{6,8-dibromo-2-[(E)-2-(4-fluorophenyl)vinyl]quinazolin-4-yl}-N,N-diethylpropane-1,3-diamine | C23H25Br2FN4 | |
| 66 | 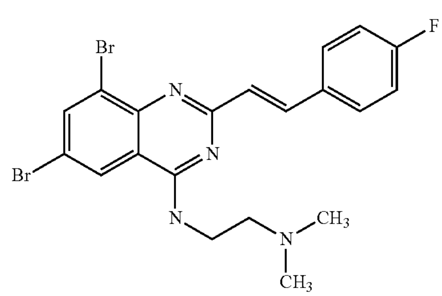 [SMILES: CN(C)CCNc1nc(/C=C/c2ccc(F)cc2)nc2c(Br)cc(Br)cc12] | N'-{6,8-dibromo-2-[(E)-2-(4-fluorophenyl)vinyl]quinazolin-4-yl}-N,N-dimethylethane-1,2-diamine | C20H19Br2FN4 | |

TABLE 1-continued

Identification of the prepared compounds.

| Example | Structure | Name | Formula | Salt |
|---|---|---|---|---|
| 67 | 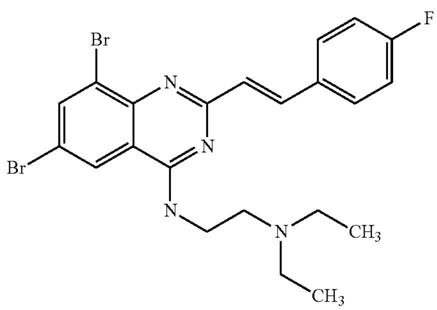 [SMILES: CCN(CC)CCNc1nc(/C=C/c2ccc(F)cc2)nc2c(Br)cc(Br)cc12] | N'-{6,8-dibromo-2-[(E)-2-(4-fluorophenyl)vinyl]quinazolin-4-yl}-N,N-diethylethane-1,2-diamine | C22H23Br2FN4 | |
| 68 | 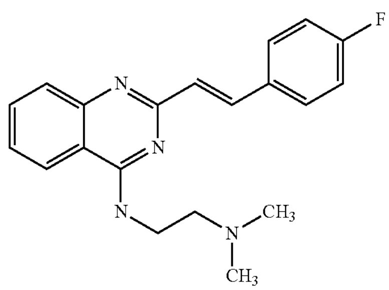 [SMILES: CN(C)CCNc1nc(/C=C/c2ccc(F)cc2)nc2ccccc12] | N'-{2-[(E)-2-(4-fluorophenyl)vinyl]quinazolin-4-yl}-N,N-dimethylethane-1,2-diamine | C20H21FN4 | |
| 69 | 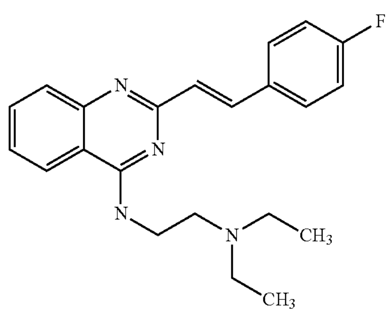 [SMILES: CCN(CC)CCNc1nc(/C=C/c2ccc(F)cc2)nc2ccccc12] | N,N-diethyl-N'-{2-[(E)-2-(4-fluorophenyl)vinyl]quinazolin-4-yl}ethane-1,2-diamine | C22H25FN4 | |
| 70 | 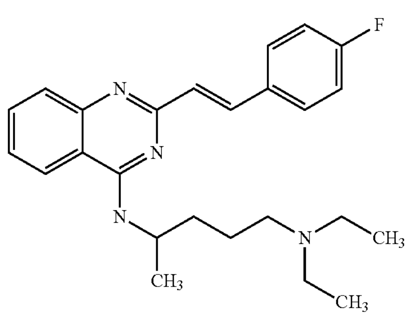 [SMILES: CCN(CC)CCCC(C)Nc1nc(/C=C/c2ccc(F)cc2)nc2ccccc12] | N1,N1-diethyl-N4-{2-[(E)-2-(4-fluorophenyl)vinyl]quinazolin-4-yl}pentane-1,4-diamine | C25H31FN4 | |
| 71 | 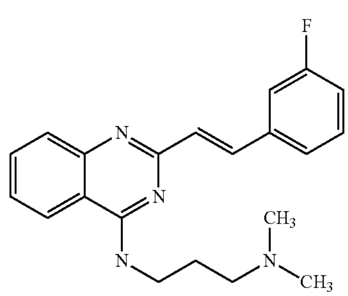 [SMILES: CN(C)CCCNc1nc(/C=C/c2cccc(F)c2)nc2ccccc12] | N'-{2-[(E)-2-(3-fluorophenyl)vinyl]quinazolin-4-yl}-N,N-dimethylpropane-1,3-diamine | C21H23FN4 | |

TABLE 1-continued

Identification of the prepared compounds.

| Example | Structure | Name | Formula | Salt |
|---|---|---|---|---|
| 72 | 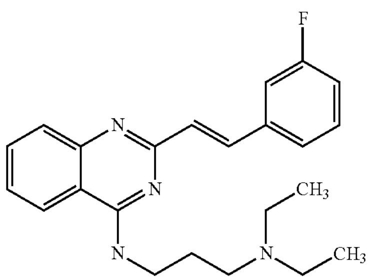 [SMILES: CCN(CC)CCCNc1nc(/C=C/c2cccc(F)c2)nc2ccccc12] | N,N-diethyl-N'-{2-[(E)-2-(3-fluorophenyl)vinyl]quinazolin-4-yl}propane-1,3-diamine | C23H27FN4 | HCl |
| 73 | 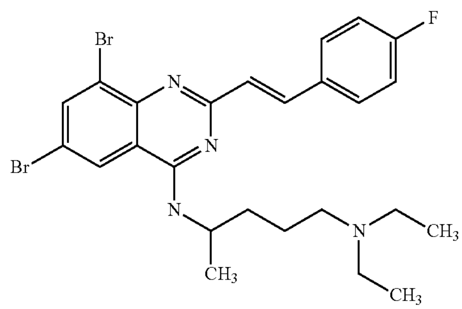 [SMILES: CCN(CC)CCCC(C)Nc1nc(/C=C/c2ccc(F)cc2)nc2c(Br)cc(Br)cc12] | N4-{6,8-dibromo-2-[(E)-2-(4-fluorophenyl)vinyl]quinazolin-4-yl}-N1,N1-diethylpentane-1,4-diamine | C25H29Br2FN4 | HCl |
| 74 | 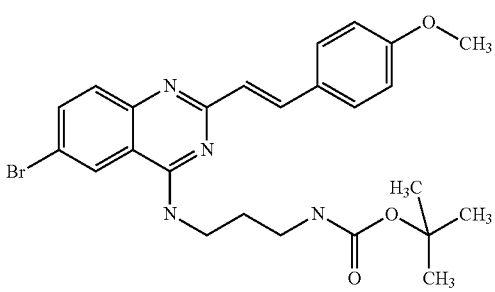 [SMILES: COc1ccc(/C=C/c2nc(NCCCNC(=O)OC(C)(C)C)c3cc(Br)ccc3n2)cc1] | tert-butyl [3-({6-bromo-2-[(E)-2-(4-methoxyphenyl)vinyl]quinazolin-4-yl}amino)propyl]carbamate | C25H29BrN4O3 | |
| 75 | 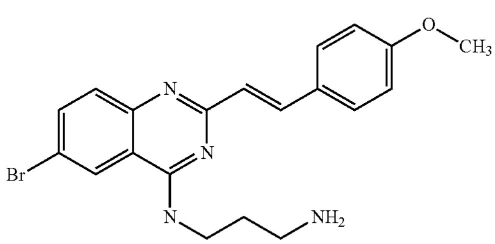 [SMILES: COc1ccc(/C=C/c2nc(NCCCN)c3cc(Br)ccc3n2)cc1] | N-{6-bromo-2-[(E)-2-(4-methoxyphenyl)vinyl]quinazolin-4-yl}propane-1,3-diamine | C20H21BrN4O | TFA |
| 76 | 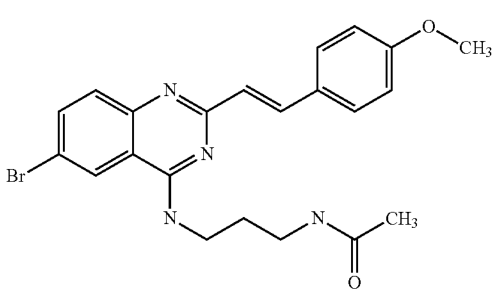 [SMILES: COc1ccc(/C=C/c2nc(NCCCNC(C)=O)c3cc(Br)ccc3n2)cc1] | N-[3-({6-bromo-2-[(E)-2-(4-methoxyphenyl)vinyl]quinazolin-4-yl}amino)propyl]acetamide | C22H23BrN4O2 | |

TABLE 1-continued

Identification of the prepared compounds.

| Example | Name | Formula | Salt |
|---|---|---|---|
| 77 | N,N-diethyl-N'-(2-{(E)-2-[4-(methylthio)phenyl]vinyl}quinazolin-4-yl)ethane-1,2-diamine | C23H28N4S | TFA |
| 78 | N,N-dimethyl-N'-(2-{(E)-2-[4-(methylthio)phenyl]vinyl}quinazolin-4-yl)propane-1,3-diamine | C22H26N4S | Oxalate |
| 79 | N'-{6-chloro-2-[(E)-2-(3,4-difluorophenyl)vinyl]quinazolin-4-yl}-N,N-dimethylpropane-1,3-diamine | C21H21ClF2N4 | Oxalate |
| 80 | N'-{6-chloro-2-[(E)-2-(3,4-difluorophenyl)vinyl]quinazolin-4-yl}-N,N-diethylpropane-1,3-diamine | C23H25ClF2N4 | |
| 81 | N'-{6-chloro-2-[(E)-2-(3,4-difluorophenyl)vinyl]quinazolin-4-yl}-N,N-dimethylethane-1,2-diamine | C20H19ClF2N4 | Oxalate |

TABLE 1-continued

Identification of the prepared compounds.

| Example | Structure | Name | Formula | Salt |
|---|---|---|---|---|
| 82 | 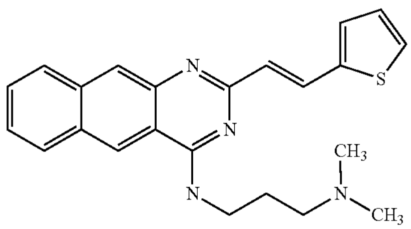 [SMILES: CN(C)CCCNc1nc(/C=C/c2cccs2)nc2cc3ccccc3cc12] | N,N-dimethyl-N'-{2-[(E)-2-(2-thienyl)vinyl]benzo[g]quinazolin-4-yl}propane-1,3-diamine | C23H24N4S | |
| 83 | 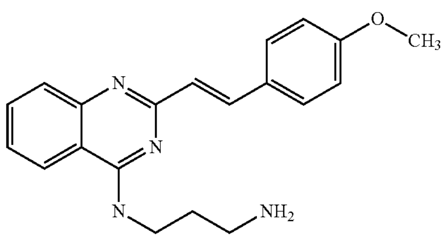 [SMILES: COc1ccc(/C=C/c2nc(NCCCN)c3ccccc3n2)cc1] | N-{2-[(E)-2-(4-methoxyphenyl)vinyl]quinazolin-4-yl}propane-1,3-diamine | C20H22N4O | Oxalate |
| 84 | 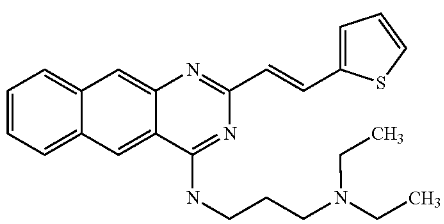 [SMILES: CCN(CC)CCCNc1nc(/C=C/c2cccs2)nc2cc3ccccc3cc12] | N,N-diethyl-N'-{2-[(E)-2-(2-thienyl)vinyl]benzo[g]quinazolin-4-yl}propane-1,3-diamine | C25H28N4S | Fumarate |
| 85 | 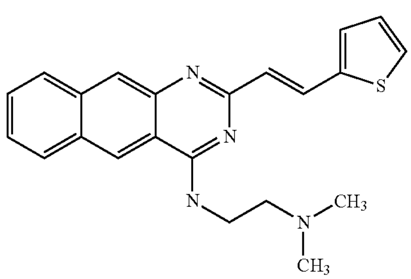 [SMILES: CN(C)CCNc1nc(/C=C/c2cccs2)nc2cc3ccccc3cc12] | N,N-dimethyl-N'-{2-[(E)-2-(2-thienyl)vinyl]benzo[g]quinazolin-4-yl}ethane-1,2-diamine | C22H22N4S | Fumarate |
| 86 | 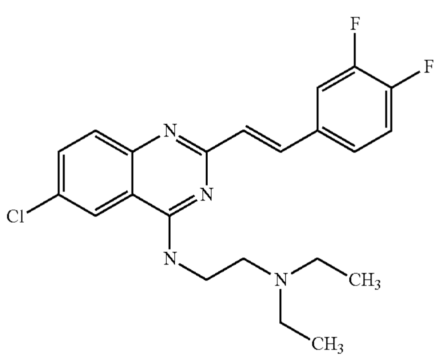 [SMILES: CCN(CC)CCNc1nc(/C=C/c2ccc(F)c(F)c2)nc2ccc(Cl)cc12] | N'-{6-chloro-2-[(E)-2-(3,4-difluorophenyl)vinyl]quinazolin-4-yl}-N,N-diethylethane-1,2-diamine | C22H23ClF2N4 | Oxalate |

TABLE 1-continued

Identification of the prepared compounds.

| Example | Structure | Name | Formula | Salt |
|---|---|---|---|---|
| 87 | 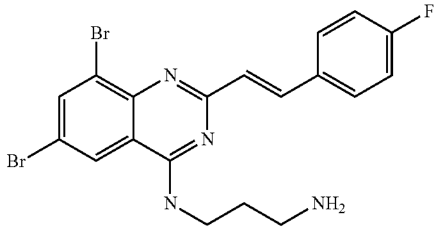 [SMILES: NCCCNc1nc(/C=C/c2ccc(F)cc2)nc2c(Br)cc(Br)cc12] | N-{6,8-dibromo-2-[(E)-2-(4-fluorophenyl)vinyl]quinazolin-4-yl}propane-1,3-diamine | C19H17Br2FN4 | TFA |
| 88 | 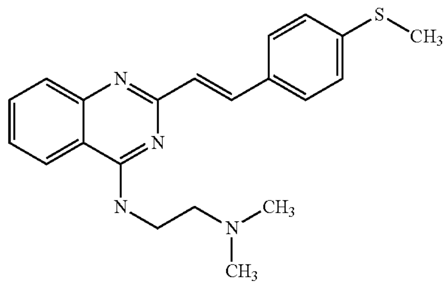 [SMILES: CSc1ccc(/C=C/c2nc(NCCN(C)C)c3ccccc3n2)cc1] | N,N-dimethyl-N'-(2-{(E)-2-[4-(methylthio)phenyl]vinyl}quinazolin-4-yl)ethane-1,2-diamine | C21H24N4S | Fumarate |
| 89 | 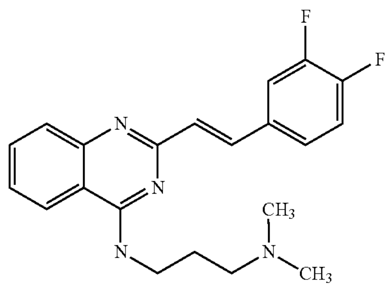 [SMILES: CN(C)CCCNc1nc(/C=C/c2ccc(F)c(F)c2)nc2ccccc12] | N'-{2-[(E)-2-(3,4-difluorophenyl)vinyl]quinazolin-4-yl}-N,N-dimethylpropane-1,3-diamine | C21H22F2N4 | |
| 90 | 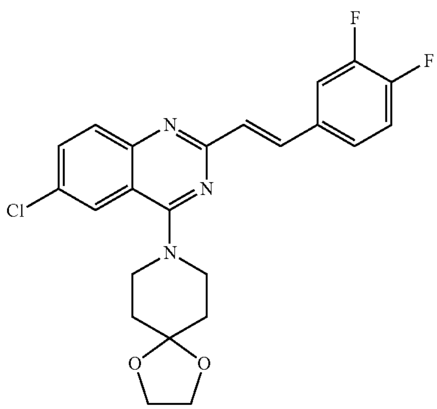 [SMILES: Fc1ccc(/C=C/c2nc(N3CCC4(CC3)OCCO4)c3cc(Cl)ccc3n2)cc1F] | 6-chloro-2-[(E)-2-(3,4-difluorophenyl)vinyl]-4-(1,4-dioxa-8-azaspiro[4.5]dec-8-yl)quinazoline | C23H20ClF2N3O2 | |
| 91 | 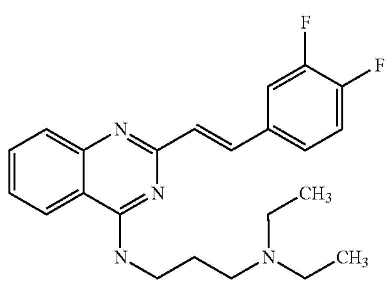 [SMILES: CCN(CC)CCCNc1nc(/C=C/c2ccc(F)c(F)c2)nc2ccccc12] | N'-{2-[(E)-2-(3,4-difluorophenyl)vinyl]quinazolin-4-yl}-N,N-diethylpropane-1,3-diamine | C23H26F2N4 | |

TABLE 1-continued

Identification of the prepared compounds.

| Example | Structure | Name | Formula | Salt |
|---|---|---|---|---|
| 92 | 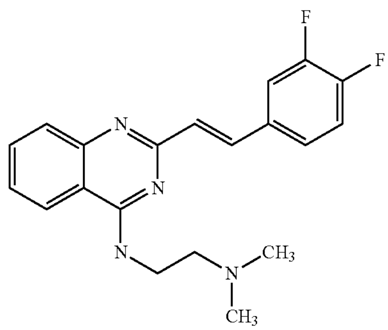 [SMILES: CN(C)CCNc1nc(/C=C/c2ccc(F)c(F)c2)nc2ccccc12] | N'-{2-[(E)-2-(3,4-difluorophenyl)vinyl]quinazolin-4-yl}-N,N-dimethylethane-1,2-diamine | C20H20F2N4 | |
| 93 | 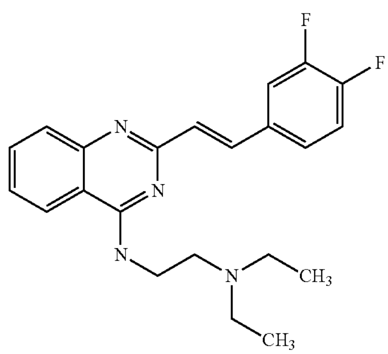 [SMILES: CCN(CC)CCNc1nc(/C=C/c2ccc(F)c(F)c2)nc2ccccc12] | N'-{2-[(E)-2-(3,4-difluorophenyl)vinyl]quinazolin-4-yl}-N,N-diethylethane-1,2-diamine | C22H24F2N4 | |
| 94 | 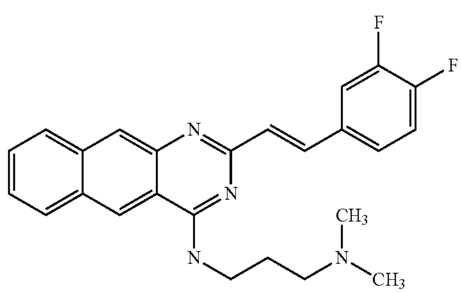 [SMILES: CN(C)CCCNc1nc(/C=C/c2ccc(F)c(F)c2)nc2cc3ccccc3cc12] | N'-{2-[(E)-2-(3,4-difluorophenyl)vinyl]benzo[g]quinazolin-4-yl}-N,N-dimethylpropane-1,3-diamine | C25H24F2N4 | |
| 95 | 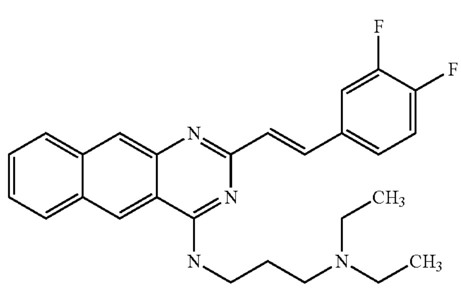 [SMILES: CCN(CC)CCCNc1nc(/C=C/c2ccc(F)c(F)c2)nc2cc3ccccc3cc12] | N'-{2-[(E)-2-(3,4-difluorophenyl)vinyl]benzo[g]quinazolin-4-yl}-N,N-diethylpropane-1,3-diamine | C27H28F2N4 | |

TABLE 1-continued

Identification of the prepared compounds.

| Example | Structure | Name | Formula | Salt |
|---|---|---|---|---|
| 96 | 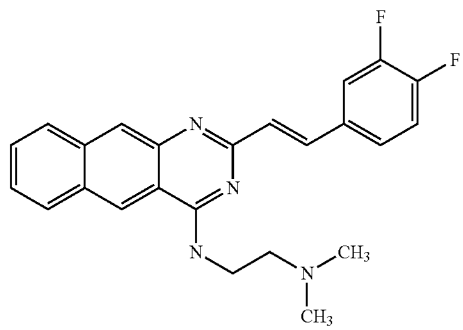 [SMILES: CN(C)CCNc1nc(/C=C/c2ccc(F)c(F)c2)nc2cc3ccccc3cc12] | N'-{2-[(E)-2-(3,4-difluorophenyl)vinyl]benzo[g]quinazolin-4-yl}-N,N-dimethylethane-1,2-diamine | C24H22F2N4 | |
| 97 | 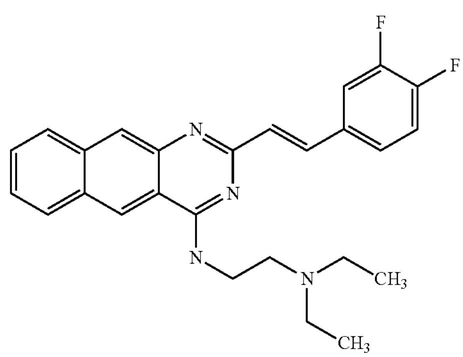 [SMILES: CCN(CC)CCNc1nc(/C=C/c2ccc(F)c(F)c2)nc2cc3ccccc3cc12] | N'-{2-[(E)-2-(3,4-difluorophenyl)vinyl]benzo[g]quinazolin-4-yl}-N,N-diethylethane-1,2-diamine | C26H26F2N4 | |
| 98 | 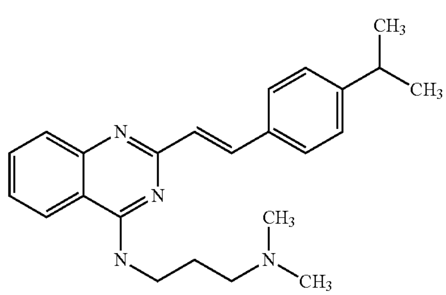 [SMILES: CC(C)c1ccc(/C=C/c2nc(NCCCN(C)C)c3ccccc3n2)cc1] | N'-{2-[(E)-2-(4-isopropylphenyl)vinyl]quinazolin-4-yl}-N,N-dimethylpropane-1,3-diamine | C24H30N4 | Fumarate |
| 99 | 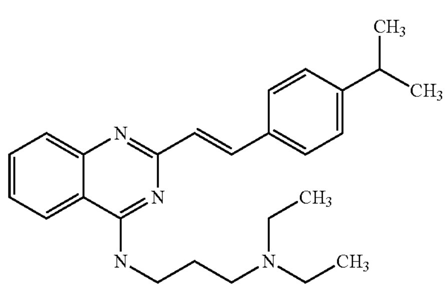 [SMILES: CCN(CC)CCCNc1nc(/C=C/c2ccc(C(C)C)cc2)nc2ccccc12] | N,N-diethyl-N'-{2-[(E)-2-(4-isopropylphenyl)vinyl]quinazolin-4-yl}propane-1,3-diamine | C26H34N4 | Fumarate |

TABLE 1-continued

Identification of the prepared compounds.

| Example | Structure | Name | Formula | Salt |
|---|---|---|---|---|
| 100 | 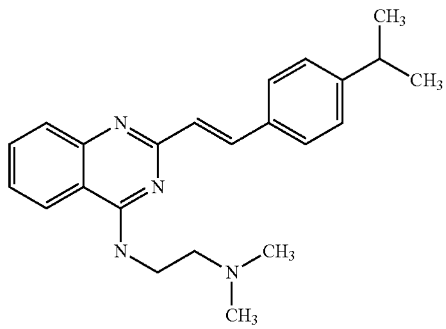 [SMILES: CC(C)c1ccc(/C=C/c2nc(NCCN(C)C)c3ccccc3n2)cc1] | N'-{2-[(E)-2-(4-isopropylphenyl)vinyl]quinazolin-4-yl}-N,N-dimethylethane-1,2-diamine | C23H28N4 | Fumarate |
| 101 | 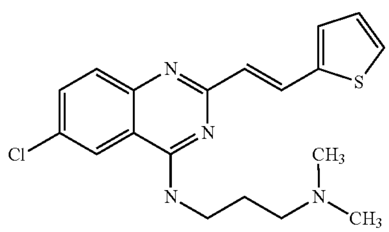 [SMILES: CN(C)CCCNc1nc(/C=C/c2cccs2)nc2ccc(Cl)cc12] | N'-{6-chloro-2-[(E)-2-(2-thienyl)quinazolin-4-yl]-N,N-dimethylpropane-1,3-diamine} | C19H21ClN4S | |
| 102 | 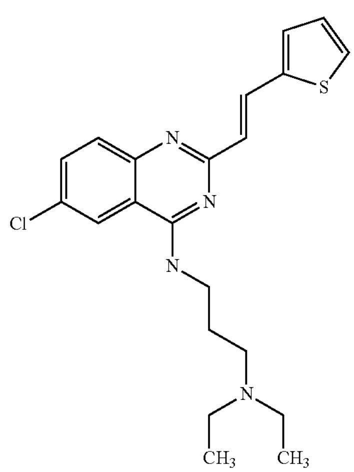 [SMILES: CCN(CC)CCCNc1nc(/C=C/c2cccs2)nc2ccc(Cl)cc12] | N'-{6-chloro-2-[(E)-2-(2-thienyl)vinyl]quinazolin-4-yl}-N,N-diethylpropane-1,3-diamine | C21H25ClN4S | |
| 103 | 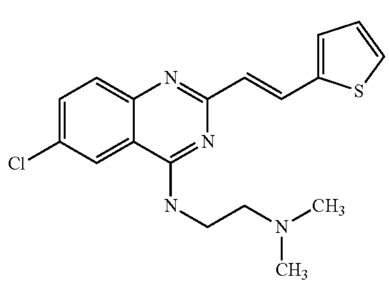 [SMILES: CN(C)CCNc1nc(/C=C/c2cccs2)nc2ccc(Cl)cc12] | N'-{6-chloro-2-[(E)-2-(2-thienyl)vinyl]quinazolin-4-yl}-N,N-dimethylethane-1,2-diamine | C18H19ClN4S | |

TABLE 1-continued

Identification of the prepared compounds.

| Example | Structure | Name | Formula | Salt |
|---|---|---|---|---|
| 104 | 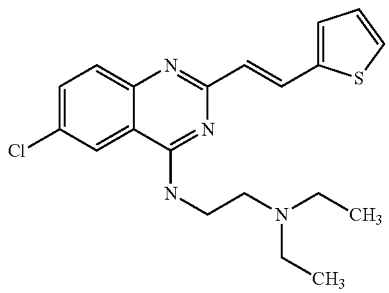 [SMILES: CCN(CC)CCNc1nc(/C=C/c2cccs2)nc2ccc(Cl)cc12] | N'-{6-chloro-2-[(E)-2-(2-thienyl)vinyl]quinazolin-4-yl}-N,N-diethylethane-1,2-diamine | C20H23ClN4S | |
| 105 | 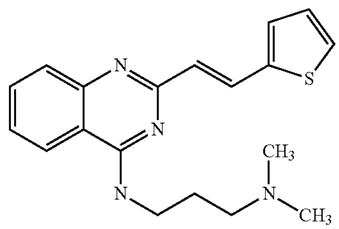 [SMILES: CN(C)CCCNc1nc(/C=C/c2cccs2)nc2ccccc12] | N,N-dimethyl-N'-{2-[(E)-2-(2-thienyl)vinyl]quinazolin-4-yl}propane-1,3-diamine | C19H22N4S | Fumarate |
| 106 | 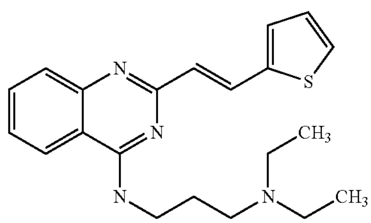 [SMILES: CCN(CC)CCCNc1nc(/C=C/c2cccs2)nc2ccccc12] | N,N-diethyl-N'-{2-[(E)-2-(2-thienyl)vinyl]quinazolin-4-yl}propane-1,3-diamine | C21H26N4S | Fumarate |
| 107 | 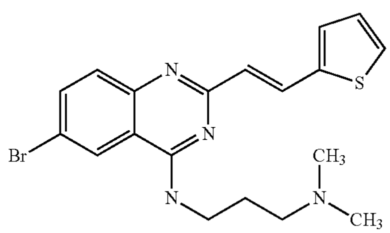 | N'-{6-bromo-2-[(E)-2-(2-thienyl)vinyl]quinazolin-4-yl}-N,N-dimethylpropane-1,3-diamine | C19H21BrN4S | |
| 108 | 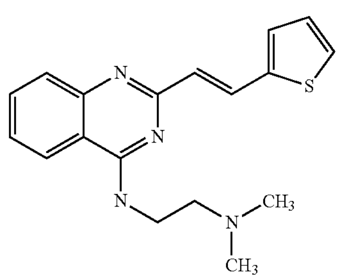 [SMILES: CN(C)CCNc1nc(/C=C/c2cccs2)nc2ccccc12] | N,N-dimethyl-N'-{2-[(E)-2-(2-thienyl)vinyl]quinazolin-4-yl)ethane-1,2-diamine} | C18H20N4S | Fumarate |
| 109 | 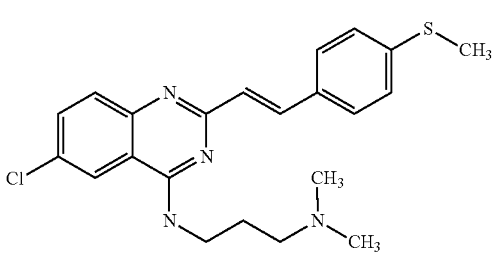 | N'-(6-chloro-2-{(E)-2-[4-(methylthio)phenyl]vinyl}quinazolin-4-yl)-N,N-dimethylpropane-1,3-diamine | C22H25ClN4S | Fumarate |

TABLE 1-continued

Identification of the prepared compounds.

| Example | Structure | Name | Formula | Salt |
|---|---|---|---|---|
| 110 | 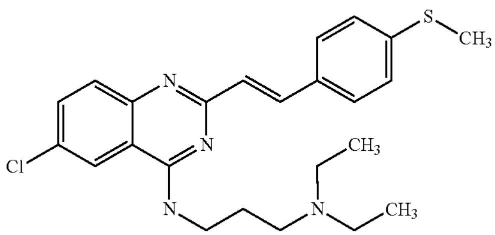 [SMILES: CCN(CC)CCCNc1nc(/C=C/c2ccc(SC)cc2)nc2ccc(Cl)cc12] | N'-(6-chloro-2-{(E)-2-[4-(methylthio)phenyl]vinyl}quinazolin-4-yl)-N,N-diethylpropane-1,3-diamine | C24H29ClN4S | Fumarate |
| 111 | 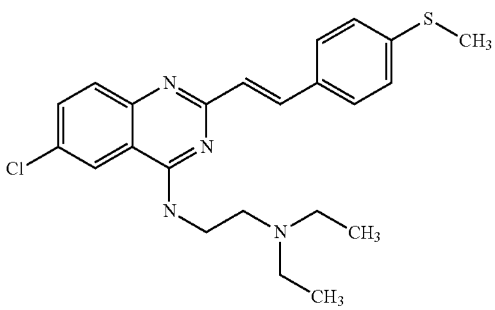 [SMILES: CCN(CC)CCNc1nc(/C=C/c2ccc(SC)cc2)nc2ccc(Cl)cc12] | N'-(6-chloro-2-{(E)-2-[4-(methylthio)phenyl]vinyl}quinazolin-4-yl)-N,N-diethylethane-1,2-diamine | C23H27ClN4S | Fumarate |
| 112 | 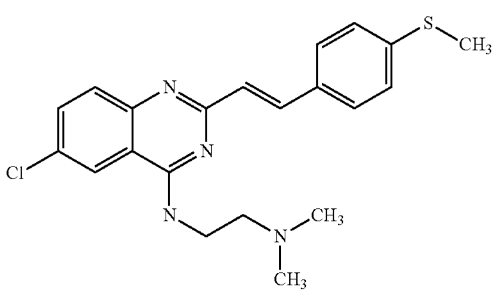 [SMILES: CSc1ccc(/C=C/c2nc(NCCN(C)C)c3cc(Cl)ccc3n2)cc1] | N'-(6-chloro-2-{(E)-2-[4-(methylthio)phenyl]vinyl}quinazolin-4-yl)-N,N-dimethylethane-1,2-diamine | C21H23ClN4S | Fumarate |
| 113 | 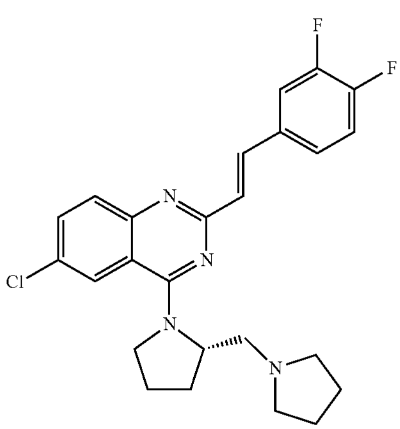 [SMILES: Fc1ccc(/C=C/c2nc(N3CCC[C@H]3CN3CCCC3)c3cc(Cl)ccc3n2)cc1F] | 6-chloro-2-[(E)-2-(3,4-difluorophenyl)vinyl]-4-[(2S)-2-(pyrrolidin-1-ylmethyl)pyrrolidin-1-yl]quinazoline | C25H25ClF2N4 | |

TABLE 1-continued

Identification of the prepared compounds.

| Example | Structure | Name | Formula | Salt |
|---|---|---|---|---|
| 114 | 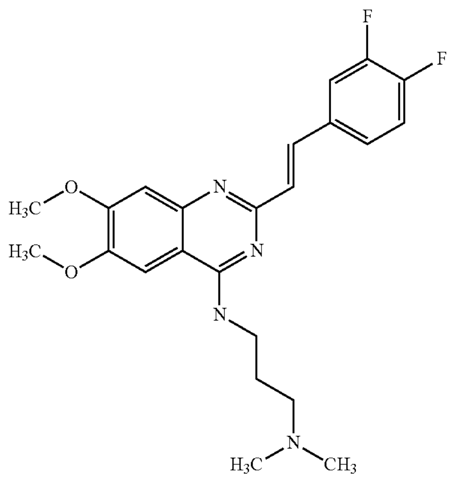 [SMILES: COc1cc2nc(/C=C/c3ccc(F)c(F)c3)nc(NCCCN(C)C)c2cc1OC] | N'-{2-[(E)-2-(3,4-difluorophenyl)vinyl]-6,7-dimethoxyquinazolin-4-yl}-N,N-dimethylpropane-1,3-diamine | C23H26F2N4O2 | Fumarate |
| 115 | 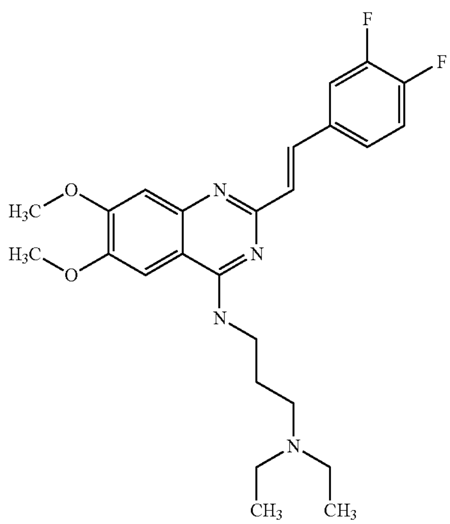 [SMILES: CCN(CC)CCCNc1nc(/C=C/c2ccc(F)c(F)c2)nc2cc(OC)c(OC)cc12] | N'-{2-[(E)-2-(3,4-difluorophenyl)vinyl]-6,7-dimethoxyquinazolin-4-yl}-N,N-diethylpropane-1,3-diamine | C25H30F2N4O2 | |
| 116 | 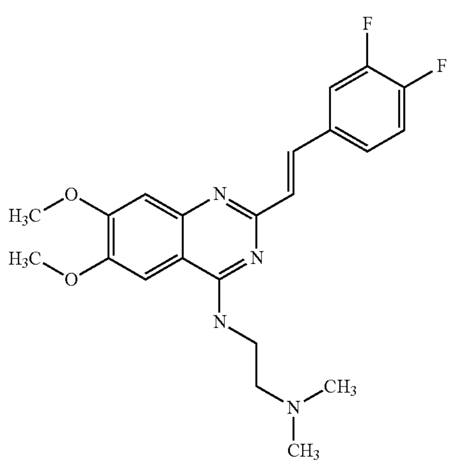 [SMILES: COc1cc2nc(/C=C/c3ccc(F)c(F)c3)nc(NCCN(C)C)c2cc1OC] | N'-{2-[(E)-2-(3,4-difluorophenyl)vinyl]-6,7-dimethoxyquinazolin-4-yl}-N,N-dimethylethane-1,2-diamine | C22H24F2N4O2 | |

TABLE 1-continued

Identification of the prepared compounds.

| Example | Structure | Name | Formula | Salt |
|---|---|---|---|---|
| 117 | 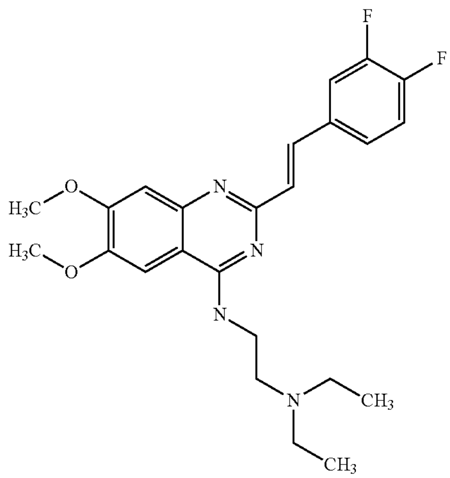 [SMILES: CCN(CC)CCNc1nc(/C=C/c2ccc(F)c(F)c2)nc2cc(OC)c(OC)cc12] | N'-{2-[(E)-2-(3,4-difluorophenyl)vinyl]-6,7-dimethoxyquinazolin-4-yl}-N,N-diethylamine-1,2-diamine | C24H28F2N4O2 | |
| 118 | 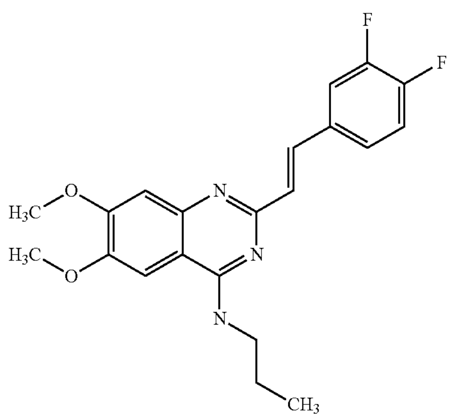 [SMILES: CCCNc1nc(/C=C/c2ccc(F)c(F)c2)nc2cc(OC)c(OC)cc12] | 2-[(E)-2-(3,4-difluorophenyl)vinyl]-6,7-dimethoxy-N-propylquinazolin-4-amine | C21H21F2N3O2 | |
| 119 | 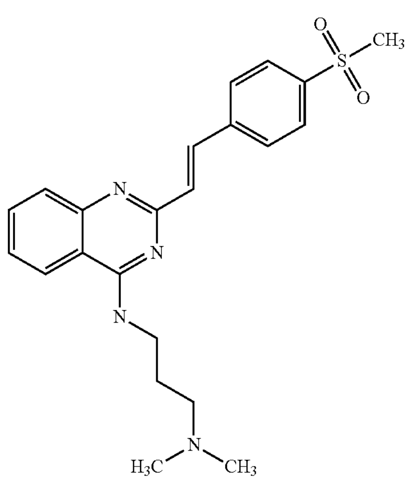 [SMILES: CN(C)CCCNc1nc(/C=C/c2ccc(S(C)(=O)=O)cc2)nc2ccccc12] | N,N-dimethyl-N'-(2-{(E)-2-[4-(methylsulfonyl)phenyl]vinyl}quinazolin-4-yl)propane-1,3-diamine | C22H26N4O2S | |

TABLE 1-continued

Identification of the prepared compounds.

| Example | Structure | Name | Formula | Salt |
|---|---|---|---|---|
| 120 | 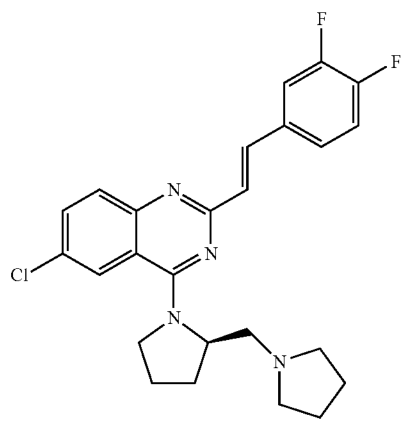 [SMILES: Fc1ccc(/C=C/c2nc(N3CCC[C@@H]3CN3CCCC3)c3cc(Cl)ccc3n2)cc1F] | 6-chloro-2-[(E)-2-(3,4-difluorophenyl)vinyl]-4-[(2R)-2-(pyrrolidin-1-ylmethyl)pyrrolidin-1-yl]quinazoline | C25H25ClF2N4 | |
| 121 | 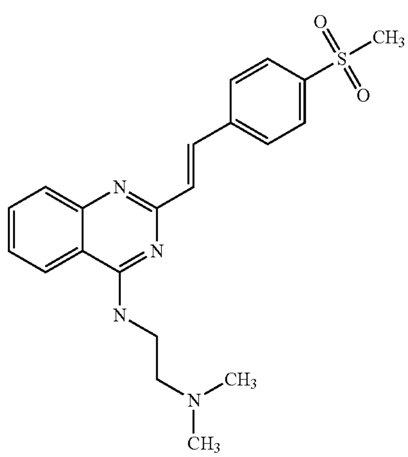 [SMILES: CN(C)CCNc1nc(/C=C/c2ccc(S(C)(=O)=O)cc2)nc2ccccc12] | N,N-dimethyl-N'-(2-{(E)-2-[4-(methylsulfonyl)phenyl]vinyl}quinazolin-4-yl)ethane-1,2-diamine | C21H24N4O2S | |
| 122 | 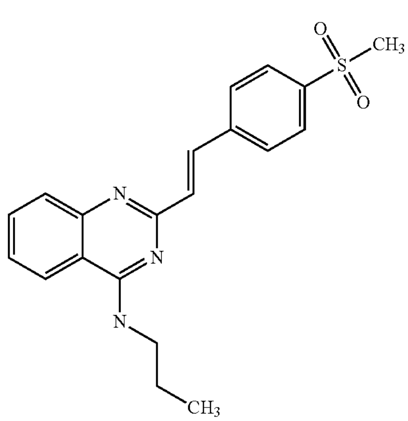 [SMILES: CCCNc1nc(/C=C/c2ccc(S(C)(=O)=O)cc2)nc2ccccc12] | 2-{(E)-2-[4-(methylsulfonyl)phenyl]vinyl}-N-propylquinazolin-4-amine | C20H21N3O2S | |

TABLE 1-continued

Identification of the prepared compounds.

| Example | Structure | Name | Formula | Salt |
|---|---|---|---|---|
| 123 | 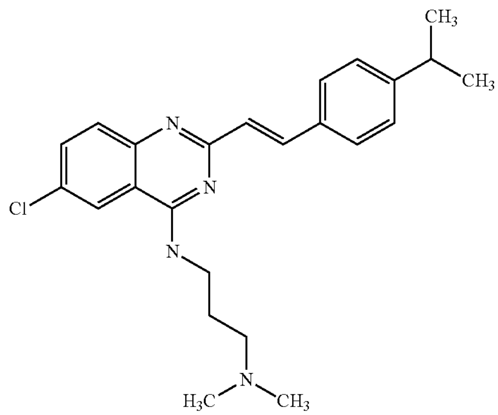 [SMILES: CC(C)c1ccc(/C=C/c2nc(NCCCN(C)C)c3cc(Cl)ccc3n2)cc1] | N'-{6-chloro-2-[(E)-2-(4-isopropylphenyl)vinyl]quinazolin-4-yl}-N,N-dimethylpropane-1,3-diamine | C24H29ClN4 | Fumarate |
| 124 | 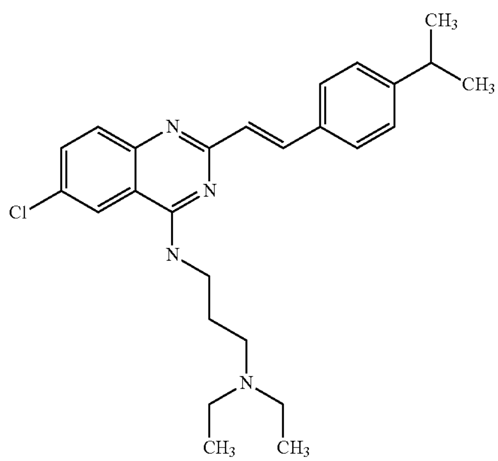 [SMILES: CCN(CC)CCCNc1nc(/C=C/c2ccc(C(C)C)cc2)nc2ccc(Cl)cc12] | N'-{6-chloro-2-[(E)-2-(4-isopropylphenyl)vinyl]quinazolin-4-yl}-N,N-diethylpropane-1,3-diamine | C26H33ClN4 | Fumarate |
| 125 | 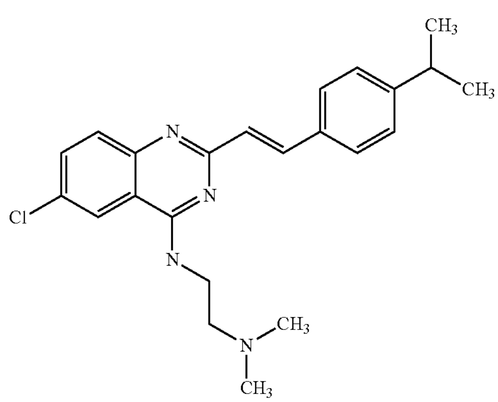 [SMILES: CC(C)c1ccc(/C=C/c2nc(NCCN(C)C)c3cc(Cl)ccc3n2)cc1] | N'-{6-chloro-2-[(E)-2-(4-isopropylphenyl)vinyl]quinazolin-4-yl}-N,N-dimethylethane-1,2-diamine | C23H27ClN4 | Fumarate |

TABLE 1-continued

Identification of the prepared compounds.

| Example | Structure | Name | Formula | Salt |
|---|---|---|---|---|
| 126 | 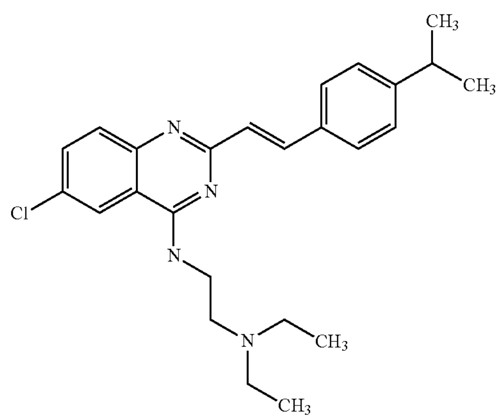 [SMILES: CCN(CC)CCNc1nc(/C=C/c2ccc(C(C)C)cc2)nc2ccc(Cl)cc12] | N'-{6-chloro-2-[(E)-2-(4-isopropylphenyl)vinyl]quinazolin-4-yl}-N,N-diethylethane-1,2-diamine | C25H31ClN4 | Fumarate |
| 127 | 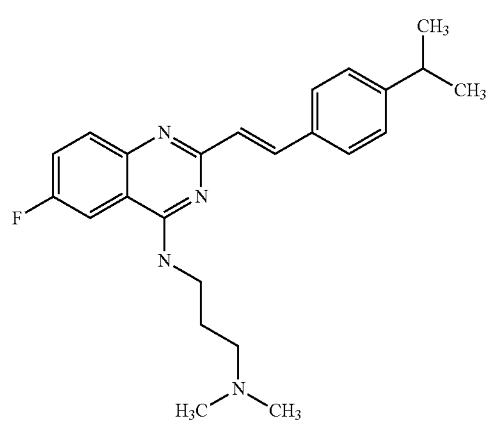 [SMILES: CC(C)c1ccc(/C=C/c2nc(NCCCN(C)C)c3cc(F)ccc3n2)cc1] | N'-{6-fluoro-2-[(E)-2-(4-isopropylphenyl)vinyl]quinazolin-4-yl}-N,N-dimethylpropane-1,3-diamine | C24H29FN4 | Fumarate |
| 128 | 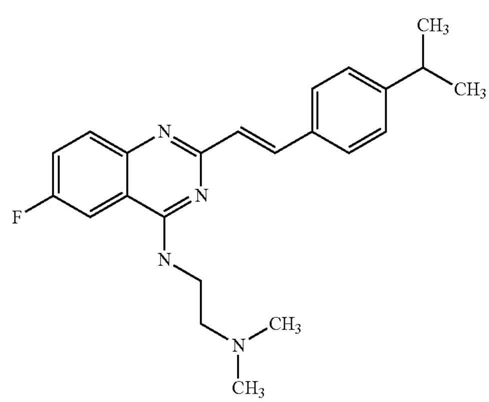 [SMILES: CC(C)c1ccc(/C=C/c2nc(NCCN(C)C)c3cc(F)ccc3n2)cc1] | N'-{6-fluoro-2-[(E)-2-(4-isopropylphenyl)vinyl]quinazolin-4-yl}-N,N-dimethylethane-1,2-diamine | C23H27FN4 | Fumarate |

TABLE 1-continued

Identification of the prepared compounds.

| Example | Structure | Name | Formula | Salt |
|---|---|---|---|---|
| 129 | 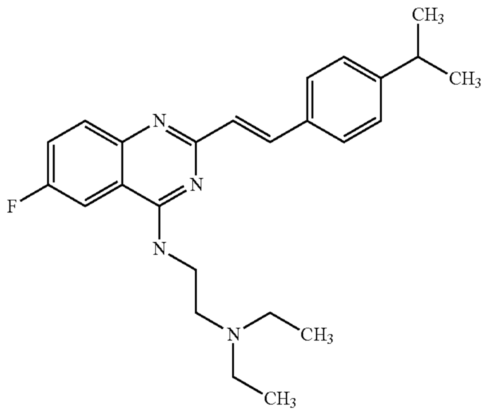 [SMILES: CCN(CC)CCNc1nc(/C=C/c2ccc(C(C)C)cc2)nc2ccc(F)cc12] | N,N-diethyl-N'-{6-fluoro-2-[(E)-2-(4-isopropylphenyl)vinyl]quinazolin-4-yl}ethane-1,2-diamine | C25H31FN4 | Fumarate |
| 130 | 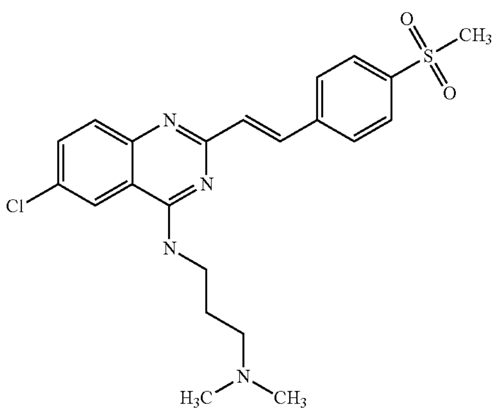 [SMILES: CN(C)CCCNc1nc(/C=C/c2ccc(S(C)(=O)=O)cc2)nc2ccc(Cl)cc12] | N'-(6-chloro-2-{(E)-2-[4-(methylsulfonyl)phenyl]vinyl}quinazolin-4-yl)-N,N-dimethylpropane-1,3-diamine | C22H25ClN4O2S | |
| 131 | 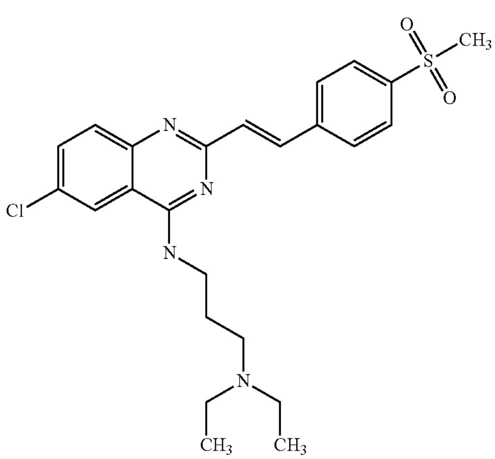 [SMILES: CCN(CC)CCCNc1nc(/C=C/c2ccc(S(C)(=O)=O)cc2)nc2ccc(Cl)cc12] | N'-(6-chloro-2-{(E)-2-[4-(methylsulfonyl)phenyl]vinyl}quinazolin-4-yl)-N,N-diethylpropane-1,3-diamine | C24H29ClN4O2S | Fumarate |

TABLE 1-continued

Identification of the prepared compounds.

| Example | Structure | Name | Formula | Salt |
|---|---|---|---|---|
| 132 | 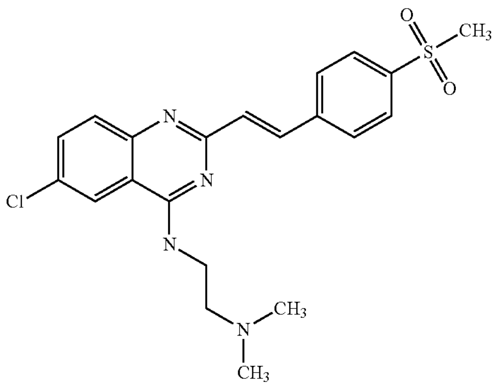 [SMILES: CN(C)CCNc1nc(/C=C/c2ccc(S(C)(=O)=O)cc2)nc2ccc(Cl)cc12] | N'-(6-chloro-2-{(E)-2-[4-(methylsulfonyl)phenyl]vinyl}quinazolin-4-yl)-N,N-dimethylethane-1,2-diamine | C21H23ClN4O2S | |
| 133 | 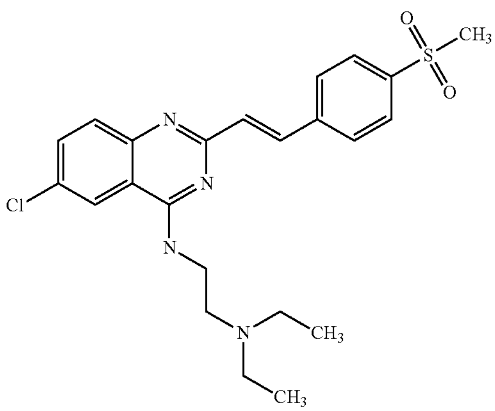 [SMILES: CCN(CC)CCNc1nc(/C=C/c2ccc(S(C)(=O)=O)cc2)nc2ccc(Cl)cc12] | N'-(6-chloro-2-{(E)-2-[4-(methylsulfonyl)phenyl]vinyl}quinazolin-4-yl)-N,N-diethylethane-1,2-diamine | C23H27ClN4O2S | Fumarate |

Analytical Characterization

All of the prepared compounds were characterized by two independent analytical method.

NMR

The 300 MHz $^1$H-NMR analysis was performed with an apparatus of type Bruker AVANCE-300 at 25° C., exact frequency was 300.14 MHz. Generally DMSO-$d_6$ was used as solvent, exceptions given. Chemical shifts are given in parts per million (δ) referenced to TMS (δ=0.00 ppm).

LCMS

The LCMS analysis was performed with a liquid chromatography mass-spectrometer Waters chromatograph with the following parameters:

Waters HPLC/MS:

MS detector. Waters SQD
  UV detector: Waters 996 DAD
  Separation module: Waters Alliance 2795

HPLC:
  Column: Waters XBridge C18, 50 mm×4.6 mm, 3.5 μm
  Solvent I: Water/0.1% HCOOH
  Solvent II: AcCN
  Acetonitrile: Riedel-deHaën; G Chromesolv (34998)
  Water: Mili-Q Academic
  Formic acid: Riedel-deHaën; extra pure (27001)
  Flow rate: 2 ml/min
  Injection: 5 μg
  Gradient:

| time | Solv. I. | Solv. II. |
|---|---|---|
| 0.00 min | 95% | 5% |
| 0.50 min | 95% | 5% |
| 5.50 min | 5% | 95% |
| 6.00 min | 5% | 95% |
| 6.50 min | 95% | 5% |
| 7.00 min | 95% | 5% |

MS: Ionization: ES$^+$/ES$^-$
  Source block temperature: 110° C.
  Desolvation temperature: 250° C.
  Desolvation gas: 500 L/h
  Cone gas: 80 L/h
  Capillary voltage: 3000 V
  Cone voltage: 30 V
  Extractor voltage: 6 V
  Rf lens voltage: 0.1 V
  Scan: 80 to 1000 m/z in 1 sec.
  Inter-scan delay: 0.1 s

TABLE 2

The analytical data of the prepared compounds

| Example | $^1$H-NMR | Rt [min] | MW calculated, monoisotopic | MW measured [−] | MW measured [+] | Purity % |
|---|---|---|---|---|---|---|
| 1 | 8.46(bs, NH); 8.35(s, 1H); 7.91(d, 1H); 7.77(d, 1H); 7.70-7.66(m, 3H); 7.04-6.98(m, 3H); 3.81(s, 3H); 2.73-2.71(m, 2H); 3.21-3.18(m, 2H); 2.79(s, 6H); 2.1-2.07(m, 2H) | 0.46; 1.95; 2.13 | 396 | 395 | 397 | 99 |
| 2 | 8.25(s, 1H); 7.85(d, 1H); 7.72(d, 1H); 7.66-7.62(m, 3H); 7.00-6.95(m, 3H); 3.8(s, 3H); 3.70-3.63(m, 2H); 3.58(1, 4H); 2.45-2.39(m, 6H); 1.91-1.82(m, 2H) | 0.45; 2.04; 2.30 | 438 | 437 | 439 | 98 |
| 3 | 8.48(bs, NH); 8.41(s, 1H); 7.91(d, 1H); 7.75-7.68(m, 4H); 7.02-6.97(m, 3H); 3.8(s, 3H); 3.74-3.72(m, 2H); 3.18-3.1(m, 6H); 2.12-2.10(m, 2H); 1.2(t, 6H) | 0.48; 2.18; 2.36 | 424 | 423 | 425 | 99 |
| 4 | 8.11(bs, NH); 8.05(d, 1H); 7.84(d, 1H); 7.74-7.69(m, 1H); 7.61-7.59(m, 3H); 7.00-6.95(m, 3H); 3.8(s, 3H); 3.70-3.64(m, 2H); 3.59-3.56(m, 4H); 2.45-2.39(m, 6H); 1.91-1.82(m, 2H) | 0.45; 1.93; 2.25 | 422 | 421 | 423 | 98 |
| 5 | 8.28(bs, NH); 8.08(d, 1H); 7.87(d, 1H); 7.75-7.70(m, 1H); 7.66-7.57(m, 3H); 7.02-6.96(m, 3H); 3.80(s, 3H); 3.70-3.68(m, 2H); 3.42-3.35(m, 6H); 1.98-1.91(m, 2H); 1.11-1.07(m, 6H) | 0.47; 2.05; 2.30 | 408 | 407 | 409 | 100 |
| 6 | 8.16(bs, NH); 8.03(d, 1H); 7.85(d, 1H); 7.74-7.69(m, 1H); 7.65-7.57(m, 3H); 7.10-6.95(m, 3H); 3.8(s, 3H); 3.68-3.61(m, 2H); 2.41-2.36(m, 2H); 2.2(s, 6H); 1.89-1.80(m, 2H) | 0.48; 1.98; 2.21 | 380 | 379 | 381 | 99 |
| 7 | 8.48(s, 1H); 8.32(bs, 1H); 7.9-7.82(m, 2H); 7.65-7.57(m, 3H); 7.00-6.95(m, 3H); 3.8(s, 3H); 3.68-3.64(m, 2H); 2.28(s, 6H); 1.92-1.85(m, 2H) | 0.46; 1.96; 2.36 | 440 | 439 | 441 | 100 |
| 8 | 8.48(s, 1H); 8.27(t, 1H); 7.84(m, 2H); 7.60(m, 3H); 6.97(m, 3H); 3.80(s, 3H); 3.65(m, 2H); 3.59(bs, 4H); 2.41(m, 6H); 1.87(m, 2H) | 0.45; 2.12; 2.37 | 482 | 481 | 482 | 98 |
| 9 | 8.66(bs, 1H); 8.41(d, 1H); 8.34(d, 1H); 8.15(dd, 1H); 7.93(d, 1H); 7.66(d.2H); 7.01(m, 3H); 3.81(s, 3H); 3.67(q, 2H); 2.41(t, 2H); 2.22(s, 6H); 1.86(m, 2H) | 0.45; 2.20; 2.38 | 407 | 406 | 408 | 99 |
| 10 | 10.10(bs, 1H); 8.84(t, 1H); 8.53(d, 1H); 8.36(d, 1H); 8.17(dd, 1H); 7.98(d, 1H); 7.70(d, 2H); 7.01(m, 3H); 3.81(s, 3H); 3.17(m, 2H); 3.10(bs, 4H); 2.12(bs, 2H); 1.20(t, 6H) | 0.44; 2.29; 2.49 | 435 | 434 | 436 | 99 |
| 11 | 8.49(s, 1H); 8.41(t, 1H); 7.88(m, 2H); 7.62(m, 3H); 6.99(m, 3H); 3.80(s, 3H); 3.68(q, 2H); 2.90(bs, 6H); 1.98(bs, 2H); 1.11(bs, 6H) | 0.45; 2.26; 2.45 | 468 | 467 | 469 | 99 |
| 12 | 8.30(bs, 1H); 8.90(d, 1H); 7.87(d, 1H); 7.72(t, 1H); 7.65(m, 3H); 7.43(t, 1H); 7.00(m, 3H); 6.57(s, 3H); 3.80(s, 3H); 3.69(q, 2H); 2.84(t, 2H); 2.50(s, 6H); 1.99(m, 2H) | 0.45; 2.19 | 362 | 361 | 363 | 100 |
| 13 | 8.66(bs, 1H); 8.24(d, 1H); 7.96(d, 1H); 7.79(t, 1H); 7.69(m, 3H); 7.51(t, 1H); 7.03(m, 3H); 3.81(s, 3H); 3.73(bs, 6H); 2.95(bs, 6H); 2.05(m, 2H) | 0.46; 2.03; 2.21 | 404 | 403 | 405 | 97 |
| 14 | 8.69(bs, 1H); 8.48(bs, 1H); 8.36(bs, 1H); 8.18(bs, 1H); 7.69(m, 2H); 7.00(m, 4H); 3.80(s, 3H); 3.75(bs, 6H); 3.05(bs, 6H); 2.07(bs, 2H) | 0.45; 2.17; 2.40 | 449 | 448 | 450 | 99 |
| 15 | 8.50(d, 1H); 8.39(t, 1H); 7.87(m, 2H); 7.77(m, 2H); 7.61(d, 1H); 7.25(t, 2H); 7.08(d, 1H); 3.87(q, 2H); 2.65(m, 2H); 2.39(s, 6H); 1.92(m, 2H) | 0.45; 2.17; 2.33 | 428 | 427 | 429 | 99 |
| 16 | 8.29(t, 1H); 8.16(d, 1H); 7.89(d, 1H); 7.73(m, 4H); 7.45(t, 1H); 7.25(t, 2H); 7.09(d, 1H); 3.66(q, 2H); 2.43(t, 2H); 2.23(6H); 1.86(m, 2H) | 0.46; 2.19 | 350 | 349 | 351 | 99 |
| 17 | 8.36(s, 1H); 8.30(s, 1H); 7.89(d, 1H); 7.75(m, 3H); 7.67(d, 1H); 7.25(m, 2H); 7.08(d, 1H); 3.66(m, 2H); 3.57(m, 4H); 2.38(bs, 6H); 1.86(m, 2H) | 0.45; 1.97; 2.28 | 378 | 377 | 379 | 99 |
| 18 | 8.47(s, 1H); 8.41(t, 1H); 7.87(m, 2H); 7.76(m, 2H); 7.60(d, 1H); 7.25(t, 2H); 7.08(d, 1H); 3.66(q, 2H); 2.64(bs, 6H); 1.87(m, 2H); 1.01(t.6H) | 0.44; 2.24; 2.44 | 456 | 455 | 457 | 98 |
| 19 | 8.54(t, 1H); 8.23(d, 1H); 7.95(d, 1H); 7.79(m, 3H); 7.71(d, 1H); 7.50(t, 1H); 7.27(t, 2H); 7.14(d, 1H); 3.75(bs, 6H); 3.01(bs, 6H); 2.06(m, 2H) | 0.46; 1.93; 2.21 | 392 | 391 | 393 | 97 |
| 20 | 8.37(bs, 2H); 7.91(d, 1H); 7.75(m, 3H); 7.68(d, 1H); 7.25(t, 2H); 7.09(d, 1H); 6.55(s, 2H); 3.67(q, 2H); 2.17(t, 2H); 2.42(s, 6H); 1.95(m, 2H) | 0.46; 1.96; 2.29 | 384 | 383 | 385 | 100 |
| 21 | 8.37(bs, 1H); 8.33(s, 1H); 7.90(d, 1H); 7.75(m, 3H); 7.68(d, 1H); 7.25(t, 2H); 7.08(d, 1H); 3.65(q, 2H); 2.58(bs, 6H); 1.85(bs, 2H); 0.99(t, 6H) | 0.46; 2.21; 2.39 | 412 | 411 | 413 | 98 |
| 22 | 8.24(t, 1H); 8.07(dd, 1H); 7.89(d, 1H); 7.76(m, 3H); 7.65(t, 1H); 7.24(t, 1H); 7.08(d, 1H); 3.66(q, 2H); 2.55(t, 2H); 2.32(s, 6H); 1.91(m, 2H) | 0.45; 1.85; 2.22 | 368 | 367 | 369 | 98 |

TABLE 2-continued

The analytical data of the prepared compounds

| Example | ¹H-NMR | Rt [min] | MW calculated, monoisotopic | MW measured [−] | MW measured [+] | Purity % |
|---|---|---|---|---|---|---|
| 23 | 10.15(bs, 1H); 8.42(bs, 1H); 8.15(dd, 1H); 7.93(d, 1H); 7.75(m, 3H); 7.67(t, 1H); 7.25(t, 2H); 7.10(d, 1H); 3.73(q, 2H); 3.05(bs, 6H); 2.08(bs, 2H); 1.18(t, 6H) | 0.46; 2.01; 2.29 | 396 | 395 | 397 | 100 |
| 24 | 8.50(s, 1H); 8.34(t, 1H); 7.88(d, 1H); 7.83(s, 1H); 7.76(t, 2H); 7.60(d, 1H); 7.25(t, 2H); 7.07(d, 1H); 3.66(m, 1H); 3.59(bs, 4H); 2.43(bs, 6H); 1.87(m, 2H) | 0.45; 2.05; 2.37 | 470 | 469 | 471 | 99 |
| 25 | 8.17(t, 1H); 8.06(dd, 1H); 7.87(d, 1H); 7.74(m, 3H); 7.64(dt, 1H); 7.25(t, 2H); 7.08(d, 1H); 3.67(q, 2H); 3.57(t, 4H); 2.40(m, 6H); 1.86(m, 2H) | 0.47; 2.22 | 410 | 409 | 411 | 96 |
| 26 | 8.36(s, 1H); 8.30(s, 1H); 7.89(d, 1H); 7.75(m, 3H); 7.67(t, 1H); 7.25(t, 2H); 7.08(d, 1H); 3.66(m, 2H); 3.57(m, 4H); 2.38(bs, 6H); 1.86(m, 2H) | 0.58; 2.08; 2.41 | 426 | 425 | 427 | 99 |
| 27 | 8.73(t, 1H); 8.43(d, 1H); 8.35(s, 1H); 8.18(d, 1H); 7.96(d, 1H); 7.78(bs, 2H); 7.26(t, 2H); 7.12(d, 1H); 3.67(q, 2H); 2.47(t, 2H); 2.56(bs, 6H); 1.88(m, 2H) | 0.44; 2.24; 2.45 | 395 | 394 | 396 | 95 |
| 28 | 8.55(bs, 1H); 8.29(d, 1H); 8.14(d, 1H); 7.93(t, 1H); 7.72(m, 3H); 7.64(t, 1H); 7.04(m, 3H); 3.64(bs, 2H); 3.04(bs, 4H); 2.76(bs, 2H); 2.66(bs, 7H); 1.94(m, 2H) | 0.46; 1.71; 2.13 | 417 | 416 | 418 | 100 |
| 29 | 8.34(bs, 1H); 7.91(d, 1H); 7.76(bs, 2H); 7.65(s, 1H); 7.27(t, 2H(; 7.16(s, 1H); 7.09(d, 1H); 3.73(bs, 2H); 3.21(bs, 2H); 3.13(bs, 4H); 2.08(bs, 2H); 1.18(bs, 6H) | 0.46; 2.10; 2.38 | 438 | 437 | 439 | 98 |
| 30 | 8.31(bs, 1H); 7.95(d, 1H); 7.77(bs, 2H); 7.64(s, 1H); 7.27(t, 2H); 7.16(s, 1H); 7.09(d, 1H); 3.91(s, 6H); 3.73(bs, 2H); 3.20(bs, 2H); 2.79(s, 6H); 2.07(bs, 2H) | 0.45; 1.98; 2.30 | 410 | 409 | 411 | 95 |
| 31 | 10.(bs, 1H); 8.86(bs, 1H); 8.52(d, 1H); 8.38(s, 1H); 8.20(d, 1H); 8.02(d, 1H); 7.82(bs, 2H); 7.27(t, 2H); 7.14(d, 1H); 3.77(bs, 2H); 3.22(bs, 2H); 8.13(bs, 4H); 2.11(bs, 2H); 1.19(bs, 6H) | 0.45; 2.45; 2.60 | 423 | 422 | 424 | 100 |
| 32 | 8.97(bs, 2H); 8.28(s, 1H); 8.04(m, 3H); 7.79(d, 2H); 7.59(m, 2H); 7.50(d, 2H); 7.24(d, 1H); 3.84(bs, 2H); 3.26(bs, 2H); 3.14(bs, 4H); 2.15(bs, 2H); 1.92(bs, 6H) | 0.44; 2.54; 2.70 | 444 | 443 | 445 | 100 |
| 33 | 8.93(s, 1H); 8.83(bs, 1H); 8.28(s, 1H); 8.07(m, 2H(; 7.98(d, 1H); 7.79(bs, 2H); 7.59(m, 2H); 7.50(m, 2H); 7.23(d, 1H); 3.95(bs, 2H); 3.23(bs, 2H); 2.79(6H); 2.15(bs, 2H) | 0.45; 2.45; 2.62 | 416 | 415 | 417 | 100 |
| 34 | 10.8(bs, 2H); 8.08(bs, 1H); 7.84(d, 1H); 7.63(m, 3H); 7.10(s, 1H); 6.98(m, 3H); 3.90(s, 6H); 3.80(s, 3H); 3.59(bs, 2H); 3.15(bs, 2H); 2.76(s, 6H); 2.59(m, 6H); 2.07(bs, 2H) | 0.45; 2.08; 2.35 | 422 | 421 | 423 | 99 |
| 35 | 11.8(bs, 3H); 8.05(bs, 1H); 7.83(d, 1H); 7.62(m, 3H); 7.10(s, 1H); 6.95(m, 3H); 3.90(s, 6H); 3.80(s, 3H); 3.45(bs, 2H); 3.25(bs, 2H); 2.59(m, 4H); 1.18(bs.6H) | 0.46; 2.28; 2.43 | 450 | 449 | 451 | 100 |
| 36 | 11, (bs, 2H); 8.86(s, 1H); 8.69(bs, 1H); 8.24(s, 1H); 7.97(m, 3H); 7.69(bs, 2H); 7.59(m, 2H); 7.05(m, 3H); 3.81(s, 3H); 3.52(bs, 2H); 3.17(bs, 2H); 2.76(s, 6H); 2.57(m, 6H); 2.12(bs, 2H) | 0.46; 2.42; 2.57 | 412 | 411 | 413 | 97 |
| 37 | 11.(bs, 2H); 8.89(s, 1H); 8.72(bs, 1H); 8.24(s, 1H); 7.99(m, 3H); 7.68(d, 2H); 7.58(m, 2H); 7.06(m, 3H); 3.81(s, 3H); 3.30(bs, 2H); 3.22(bs, 2H); 3.11(bs, 4H); 2.56(m, 4H); 2.12(bs, 2H); 1.18(bs, 6H) | 0.45; 2.50; 2.65 | 440 | 439 | 441 | 97 |
| 38 | 8.90(s, 1H); 8.80(m, 1H); 822(s, 1H); 8.00(m, 3H); 7.60(m, 4H); 7.01(bs, 3H); 3.81(bs, 3H); 3.64(bs, 4H); 2.64(m, 8H); 1.99(bs, 2H) | 2.56 | 454 | 453 | 455 | 97 |
| 39 | 8.90(s, 1H); 8.73(bs, 1H); 8.25(s, 1H); 8.02(m, 3H); 7.80(m, 2H); 7.57(m, 2H); 7.26(t, 2H); 7.17(d, 1H); 6.57(s, 3H); 3.77(q, 2H); 2.85(t, 2H); 2.50(s, 6H); 2.04(m, 2H) | 0.46; 2.18; 2.48 | 400 | 399 | 401 | 99 |
| 40 | 11.(bs(2H); 8.89(s, 1H); 8.74(bs, 1H); 8.27(s, 1H); 8.02(m, 3H); 7.81(bs, 2H); 7.57(m, 2H); 7.27(bs, 2H); 7.16(d, 1H); 3.82(bs, 2H): 3.24(bs, 2H); 3.12(bs, 4H); 2.59(m, 4H); 2.11(bs, 2H); 1.18(bs, 6H) | 0.45; 2.45; 2.60 | 428 | 427 | 429 | 100 |
| 41 | 9.01(bs, 1H); 8.95(s, 1H); 8.28(s, 1H); 8.06(m, 3H); 7.82(bs, 2H); 7.65(s, 1H); 7.58(s, 1H); 7.30(m, 2H); 7.19(d, 1H); 3.84(bs, 2H); 3.73(bs, 4H); 2.82(bs, 6H); 2.10(bs, 2H) | 2.52 | 442 | 441 | 443 | 95 |
| 42 | 7.86-7.71(m, 4H); 7.58(bs, 1H); 7.24(m, 2H); 7.09(s, 1H); 7.02(d, 1H); 3.89(s, 6H); 3.64(bs, 2H); 3.58(bs, 4H); 2.40(bs, 6H); 1.87(m, 2H) | 0.45; 2.28 | 452 | 451 | 453 | 98 |

TABLE 2-continued

The analytical data of the prepared compounds

| Example | ¹H-NMR | Rt [min] | MW calculated, monoisotopic | MW measured [−] | MW measured [+] | Purity % |
|---|---|---|---|---|---|---|
| 43 | 8.63(bs, 1H); 8.45(d, 1H); 8.36(s, 1H); 8.16(d, 1H); 7.95(d, 1H); 7.79(bs, 2H); 7.26(bs, 2H); 7.10(d, 1H); 3.69(bs, 2H); 2.42(bs, 6H); 2.30(bs, 4H); 2.12(s, 3H); 1.86(bs, 2H) | 0.43; 2.08; 2.30 | 450 | 449 | 451 | 100 |
| 44 | 8.39(bs, 1H); 8.19(d, 1H); 7.88(d, 1H); 7.64(m, 3H); 7.47(d, 1H); 6.99(m, 3H); 3.80(s, 3H); 3.64(bs, 2H); 2.42(bs, 2H); 2.23(s, 6H); 1.85(bs, 2H) | 0.44; 2.01; 2.29 | 396 | 395 | 397 | 100 |
| 45 | 10.10(bs, 1H); 8.57(bs, 1H); 8.30(d, 1H); 7.92(d, 1H); 7.67(bs, 3H); 7.49(d, 1H); 6.99(d, 3H); 3.80(s, 3H); 3.72(bs, 2H); 3.09(bs, 6H); 2.09(bs, 2H); 1.19(bs, 6H) | 0.45; 2.05; 2.37 | 424 | 423 | 425 | 100 |
| 46 | 8.31(bs, 1H); 8.21(d, 1H); 7.86(d, 1H); 7.64(m, 3H); 7.47(d, 1H); 6.96(m, 3H); 3.80(s, 3H); 3.66(bs, 2H); 3.57(bs, 4H); 2.40(m, 6H); 1.86(bs, 2H) | 0.45; 1.95; 2.30 | 438 | 437 | 439 | 99 |
| 47 | 8.29(bs, 1H); 8.20(d, 1H); 7.87(d, 1H); 7.65(bs, 3H); 7.46(d, 1H); 6.95(m, 3H); 3.81(s, 3H); 3.66(bs, 2H); 2.41(bs, 6H); 2.32(bs, 4H); 1.85(bs, 2H) | 0.45; 1.91; 2.25 | 451 | 450 | 452 | 100 |
| 48 | 8.43(bs, 1H); 8.21(d, 1H); 7.09(d, 1H); 7.76(bs, 2H); 7.68(s, 1H); 7.49(d, 1H); 7.25(t, 2H); 7.08(d, 1H); 3.64(bs, 2H); 2.42(bs, 2H); 2.22(s, 6H); 1.85(bs, 2H) | 2.13; 2.29 | 384 | 383 | 385 | 99 |
| 49 | 8.44(s, 1H); 8.20(d, 1H); 7.90(d.1H); 7.75(bs, 2H); 7.68(s, 1 H); 7.50(d, 1H); 7.25(bs, 2H); 7.07(d, 1H); 3.65(bs, 2H); 2.57(bs, 6H); 1.85(bs, 2H); 0.98(bs, 6H) | 2.36 | 412 | 411 | 413 | 100 |
| 50 | 8.35(t, 1H); 8.23(d, 1H); 7.89(d, 1H); 7.76(m, 2H); 7.568(s, 1H); 7.50(d, 1H); 7.25(m, 2H); 7.07(d, 1H); 3.66(bs, 2H); 3.56(bs, 4H); 2.39(bs, 6H); 1.86(m, 2H) | 2.31 | 426 | 425 | 427 | 100 |
| 51 | 8.35(bs, 1H); 8.22(d, 1H); 7.89(d, 1H); 7.76(bs, 2H); 7.68(s, 1H); 7.49(d, 1H); 7.25(m, 2H); 7.07(d, 1H); 3.68(bs, 2H); 2.41(bs, 6H); 2.31(bs, 4H); 1.84(bs, 2H) | 2.23 | 439 | 438 | 440 | 99 |
| 52 | 14.6(bs, 1H); 10.25(bs, 1H); 10.10(bs, 1H); 8.55(bs, 1H); 8.25(d, 1H); 7.86(s, 1H); 7.70(bs, 1H); 7.63(bs, 2H); 6.93(d.1H); 6.80(bs, 2H); 3.88(bs, 2H); 3.10(bs, 2H); 3.04(s, 6H); 2.14(bs, 2H); 1.21(s, 6H) | 0.46; 2.36; 2.53 | 437 | 436 | 438 | 99 |
| 53 | 8.32(bs, 1H); 8.19(d, 1H); 7.85(d, 1H); 7.73(m, 1H); 7.65(d, 1H); 7.45(t, 1H); 7.14(d, 1H); 7.02(s, 2H); 3.86(s, 6H); 3.70(s, 5H); 2.68(bs, 2H); 2.41 (s, 6H); 1.94(m, 2H) | 0.44; 2.12 | 422 | 421 | 423 | 100 |
| 54 | 8.30(bs, 1H); 8.19(bs, 1H); 7.86(d, 1H); 7.74(m, 1H); 7.67(m, 1H); 7.47(bs, 1H); 7.13(d, 1H); 7.02(s, 2H); 3.87(s, 6H); 3.70(m, 12H); 2.68(m, 8H) | 0.45; 1.86; 2.13 | 464 | 483 | 465 | 99 |
| 55 | 8.49(s, 1H); 8.36(bs, 1H); 7.85(m, 3H); 7.61(d, 1H); 7.53(bs, 1H); 7.46(m, 1H); 7.15(d, 1H); 3.64(bs, 2H); 2.41(bs, 2H); 2.22(s, 6H); 1.85(bs, 2H) | 0.46; 2.13; 2.36 | 446 | 445 | 447 | 98 |
| 56 | 8.48(s, 1H); 8.44(bs, 1H); 7.86(m, 3H); 7.61(d, 1H); 7.53(bs, 1H); 7.47(bs, 1H); 7.16(d, 1H); 3.65(bs, 2H); 2.63(bs, 6H); 1.87(bs, 2H); 1.01(bs, 6H) | 0.46; 2.26; 2.47 | 474 | 473 | 475 | 97 |
| 57 | 8.52(s, 1H); 8.28(bs, 1H); 7.86(m, 3H); 7.61(d, 1H); 7.51(bs, 1H); 7.46(m, 1H); 7.15(d, 1H); 3.73(bs, 2H); 2.58(bs, 2H); 2.25(s, 6H) | 0.46; 2.16; 2.38 | 432 | 431 | 433 | 99 |
| 58 | 8.47(s, 1H); 8.34(bs, 1H); 7.86(m, 3H); 7.61(d, 1H); 7.48(bs, 2H); 7.16(d, 1H); 3.70(bs, 2H); 2.72(2H); 2.61(bs, 4H); 1.02(bs, 6H) | 0.46; 2.29; 2.51 | 460 | 459 | 461 | 97 |
| 59 | 8.21(bs, 1H); 8.06(d, 1H); 7.86(bs, 1H); 7.82(s, 1H); 7.73(m, 1H); 7.67(m, 1H); 7.52(m, 1H); 7.45(m, 1H); 7.15(d, 1H); 3.64(bs, 2H); 2.40(bs, 2H); 2.21(s, 6H); 1.85(bs, 2H) | 0.45; 1.99; 2.22 | 386 | 385 | 387 | 99 |
| 60 | 8.26(bs, 1H); 8.06(d, 1H); 7.86(m, 2H); 7.74(s, 1H); 7.66(d, 1H); 7.52(bs, 1H); 7.46(d, 1H); 7.16(d, 1H); 3.66(bs, 2H); 2.62(bs, 6H); 1.88(bs, 2H); 1.01(bs, 6H) | 0.45; 1.97; 2.32 | 414 | 413 | 415 | 98 |
| 61 | 8.09(m, 2H); 7.87(bs, 1H); 7.82(s, 1H); 7.73(m, 1H); 7.67(m, 1H); 7.51(bs, 1H); 7.47(m, 1H); 7.16(d, 1H); 3.74(bs, 2H); 2.59(bs, 2H); 2.26(s, 6H) | 0.44; 1.76; 2.18 | 372 | 371 | 373 | 100 |
| 62 | 8.18(bs, 1H); 8.04(d, 1H); 7.85(m, 2H); 7.73(d, 1H); 7.66(d, 1H); 7.48(bs, 2H); 7.16(d, 1H); 3.71(bs, 2H); 2.732(bs, 2H); 2.62(bs, 4H); 1.02(bs, 6H) | 0.45; 2.02; 2.28 | 400 | 399 | 401 | 99 |
| 63 | 8.21(d, 1H); 7.85(m, 3H); 7.72(d, 1H); 7.66(d, 1H); 7.53(bs, 1H); 7.46(d, 1H); 7.15(d, 1H); 4.63(bs, 1H); 3.31(bs, 2H); 2.50(bs, 4H); 1.61(bs, 4H); 1.28(bs, 3H); 0.91(bs, 6H) | 0.45; 2.20; 2.50 | 442 | 441 | 443 | 99 |

TABLE 2-continued

The analytical data of the prepared compounds

| Example | ¹H-NMR | Rt [min] | MW calculated, monoisotopic | MW measured [−] | MW measured [+] | Purity % |
|---|---|---|---|---|---|---|
| 64 | 8.50(bs, 2H); 8.25(s, 1H); 7.94(d, 1H); 7.79(bs, 2H); 7.25(bs, 2H); 7.09(d, 1H); 3.65)bs, 2H); 2.39(bs, 2H); 2.21(s, 6H); 1.84(bs, 2H) | 3.35 | 506 | 505 | 507 | 99 |
| 65 | 8.54(s, 1H); 8.49(s, 1H); 8.26(s, 1H); 7.95(d, 1H); 7.78(bs, 2H); 7.25(t, 2H); 7.09(d, 1H); 3.66(bs, 2H); 2.56(bs, 6H); 1.84(bs, 2H); 0.99(bs, 6H) | 3.52 | 534 | 533 | 535 | 98 |
| 66 | 8.53(s, 1H); 8.42(bs, 1H); 8.26(s, 1H); 7.96(d, 1H); 7.78(bs, 2H); 7.25(t, 2H); 7.09(d, 1H); 3.74(bs, 2H); 2.58(bs, 2H); 2.25(s, 6H) | 3.43 | 492 | 491 | 493 | 98 |
| 67 | 8.48(bs, 2H); 8.26(s, 1H); 7.94(d, 1H); 7.76(bs, 2H); 7.25(t, 2H); 7.09(d, 1H); 3.69(bs, 2H); 2.70(bs, 2H); 2.58(bs, 4H); 1.01(bs, 6H) | 3.61 | 520 | 519 | 521 | 98 |
| 68 | 8.17(bs, 1H); 8.16(bs, 1H); 7.90(d, 1H); 7.73(bs, 2H); 7.68(s, 1H); 7.45(m, 1H); 7.27(bs, 2H); 7.10(d, 1H); 3.75(bs, 2H); 2.60(bs, 2H); 2.28(s, 6H) | 0.45; 2.03 | 336 | 335 | 337 | 100 |
| 69 | 8.21(bs, 1H); 8.15(d, 1H); 8.90(m, 4H); 7.45(s, 1H); 7.25(bs, 2H); 7.12(d, 1H); 3.72(bs, 2H); 2.73(bs, 2H); 2.63(bs, 4H); 1.04(bs, 6H) | 0.44; 2.11 | 364 | 363 | 365 | 100 |
| 70 | 8.30(d, 1H); 7.73(m, 6H); 7.44(t, 1H); 7.24(bs, 2H); 7.08(d, 1H); 4.66(bs, 1H); 2.50(bs, 6H); 1.62(bs, 4H); 1.29(bs, 3H); 0.90(bs, 6H) | 0.45; 2.08; 2.40 | 406 | 405 | 407 | 100 |
| 71 | 8.32(bs, 1H); 8.18(d, 1H); 7.89(d, 1H); 7.72(m, 2H); 7.53(m, 4H); 7.20(d, 1H); 7.18(s, 1H); 3.67(bs, 2H); 2.49(bs, 2H); 2.26(s, 6H); 1.88(bs, 2H) | 0.45; 2.13 | 350 | 349 | 351 | 100 |
| 72 | 14.55(bs, 1H); 10.49(bs, 1H); 10.41(bs, 1H); 8.64(d, 1H); 7.98(m, 2H); 7.66(m, 4H); 7.40(m, 2H); 3.95(bs, 2H); 3.24(bs, 2H); 3.10(bs, 4H); 2.17(bs, 2H); 1.21(bs, 6H) | 0.45; 1.90; 2.27 | 378 | 377 | 379 | 100 |
| 73 | 9.71(bs, 1H); 8.67(s, 1H); 8.27(s, 1H); 8.19(d, 1H); 7.95(d, 1H); 7.83(bs, 2H); 7.25(bs, 2H); 7.10(d, 1H); 4.68(bs, 1H); 3.02(bs, 6H); 1.72(bs, 4H); 1.31(bs, 3H); 1.11(bs, 6H) | 3.69 | 562 | 561 | 563 | 97 |
| 74 | 8.48(s, 1H); 8.20(bs, 1H); 7.85(m, 2H); 7.66(d, 1H); 7.58(d, 1H); 6.98(d, 2H); 6.85(s, 1H); 3.80(s, 3H); 3.61(bs, 2H); 3.07(bs, 2H); 1.82(bs, 2H); 1.36(s, 9H) | 3.54 | 512 | 511 | 513 | 98 |
| 75 | 9.62(bs, 1H); 8.65(s, 1H); 8.19(d, 1H); 8.09(s, 1H); 7.84(bs, 2H); 7.73(m, 3H); 7.08(m, 3H); 3.84(s, 3H); 3.60(bs, 2H); 2.99(bs, 2H); 2.02(bs, 2H) | 0.45; 2.05; 2.28 | 412 | 411 | 413 | 100 |
| 76 | 8.49(s, 1H); 8.27(bs, 1H); 7.90(s, 1H); 7.65(m, 3H); 7.66(d, 2H); 7.58(d, 1H); 6.98(m, 2H); 3.80(s, 3H); 3.63(bs, 2H); 3.17(bs, 2H); 1.81(s, 5H) | 0.47; 2.67; 2.82 | 454 | 453 | 455 | 98 |
| 77 | 9.99(bs, 1H); 9.73(bs, 1H); 8.36(d, 1H); 8.27(d, 1H); 8.02(t, 1H); 7.83(d, 1H); 7.73(d, 3H); 7.40(d, 2H); 7.25(d, 1H); 4.21(bs, 2H); 3.47(bs, 2H); 3.32(bs, 4H); 2.55(s, 3H); 1.24(t.6H) | 0.45; 2.05; 2.35 | 392 | 391 | 393 | 99 |
| 78 | 8.43(bs, 1H); 8.23(bs, 1H); 7.9(d, 1H); 7.68(m, 5H); 7.48-7.15(m, 5H); 7.13(d, 1H); 3.74(bs, 2H); 3.20(bs, 2H); 2.78(bs, 6H); 2.11(bs, 2H) | 0.45; 1.89; 2.15; 2.34 | 378 | 377 | 379 | 100 |
| 79 | 8.44(bs, 1H); 8.36(s, 1H); 7.89(m, 2H); 7.74(m, 2H); 7.59(bs, 1H); 7.47(m, 1H); 7.18(d, 1H); 3.72(bs, 2H); 3.18(bs, 2H); 2.77(bs, 6H); 2.07(bs, 2H) | 0.46; 2.03; 2.36 | 402 | 401 | 403 | 100 |
| 80 | 8.40(bs, 1H); 8.34(s, 1H); 7.87(m, 2H); 7.76(d, 1H); 7.68(d, 1H); 7.53(bs, 1H); 7.47(m, 1H); 7.16(d, 1H); 3.66(bs, 2H); 2.60(bs, 6H); 1.72(bs, 2H); 1.00(bs, 6H) | 0.45; 2.20; 2.45 | 430 | 429 | 431 | 95 |
| 81 | 8.56(bs, 1H); 8.32(s, 1H); 7.92(m, 2H); 7.77(m, 2H); 7.59(bs, 1H); 7.47(d, 1H); 7.20(d, 1H); 4.00(bs, 2H); 3.41(bs, 2H); 2.89(s, 6H) | 0.45; 2.05; 2.37 | 388 | 387 | 389 | 100 |
| 82 | 8.90(s, 1H); 8.78(bs, 1H); 8.23(s, 1H); 8.06(m, 3H); 7.54(m, 3H); 7.43(s, 1H); 7.15(s, 1H); 6.88(d, 1H); 6.54(s, 1H); 3.75(bs, 2H); 2.64(bs, 2H); 2.37(m, 6H); 1.96 (bs, 2H) | 0.45; 2.13; 2.33 | 388 | 387 | 389 | 99 |
| 83 | 8.36(bs, 1H); 8.20(d, 1H); 8.06(bs, 2H); 7.74(m, 5H); 7.45(t, 1H); 7.00(m, 3H); 3.81(s, 3H); 3.72(bs, 2H); 2.95(m, 2H); 2.01(m, 2H) | 0.45; 1.88; 2.13 | 334 | 333 | 335 | 99 |
| 84 | 8.90(s, 1H); 8.78(bs, 1H); 8.24(s, 1H); 8.08(m, 3H); 7.57(m, 3H); 7.43(s, 1H); 7.15(s, 1H); 6.89(d, 1H); 6.57(s, 2.5H); 3.77(bs, 2H); 2.96(bs, 2H); 2.88(m, 4H); 2.04(bs, 2H); 1.12(bs, 6H) | 0.44; 2.39 | 416 | 415 | 417 | 93 |
| 85 | 8.88(s, 1H); 8.68(bs, 1H); 8.24(s, 1H); 8.07(m, 3H); 7.60(s, 1H); 7.54(m, 2H); 7.43(s, 1H): 7.14(s.1H); 6.89(d, 1H); 6.58(s, 2H); 3.92(bs, 2H); 2.94(bs, 2H); 2.56(s.6H) | 0.44; 1.89; 2.22 | 374 | 373 | 375 | 100 |

TABLE 2-continued

The analytical data of the prepared compounds

| Example | ¹H-NMR | Rt [min] | MW calculated, monoisotopic | MW measured [−] | MW measured [+] | Purity % |
|---|---|---|---|---|---|---|
| 86 | 8.60(bs, 1H); 8.31(s, 1H); 7.94-7.72(m, 4H); 7.57(bs, 1H); 7.49(m, 1H); 7.20(d, 1H); 6.(bs, 1H); 4.01(bs, 2H); 3.40(bs, 2H); 3.27(bs, 4H); 1.23(bs, 6H) | 0.45; 2.25; 2.50; 2.83 | 416 | 415 | 417 | 100 |
| 87 | 8.55(bs, 1H); 8.52(s, 1H); 8.29(s, 1H); 7.82(m, 4H); 7.75(bs, 2H); 7.28(m, 2H); 7.12(d, 1H); 3.73(bs, 2H); 2.98(bs, 2H); 1.83(bs, 2H) | 3.28 | 478 | 477 | 479 | 93 |
| 88 | 8.28(bs, 1H); 8.17(d, 1H); 7.88(d, 1H); 7.71(t, 1H); 7.65(m, 3H); 7.44(t, 1H); 7.29(m, 2H); 7.10(d, 1H); 7.10(d, 1H); 6.57)s, 2H); 3.85(bs, 2H); 3.90(bs, 2H); 2.48(s, 9H) | 0.46; 2.25 | 364 | 363 | 365 | 100 |
| 89 | 8.30(bs, 1H); 8.17(d, 1H); 7.87(d, 1H); 7.83(s, 1H); 7.71(m, 2H); 7.47(m, 3H); 7.16(d, 1H); 3.66(q, 2H); 2.40(t, 2H); 2.21(s, 6H); 1.85(m, 2H) | 0.45; 1.95; 2.20 | 368 | 367 | 369 | 100 |
| 90 | 7.90(m, 3H); 7.80(s, 2H); 7.58(m, 1H); 7.48(q, 1H); 7.23(d, 1H); 3.98(s, 4H); 3.83(bs, 4H); 1.88(bs, 4H) | 3.63 | 443 | 442 | 444 | 93 |
| 91 | 8.37(s, 1H); 8.19(d, 1H); 7.87(m, 2H); 7.70(m, 2H); 7.47(m, 3H); 7.17(d, 1H); 3.70(bs, 2H); 2.76(bs, 6H); 1.94(bs, 2H); 1.06(bs.6H) | 0.48; 2.07; 2.31 | 396 | 395 | 397 | 100 |
| 92 | 8.17(m, 2H); 7.86(m, 2H); 7.74(t, 1H); 7.67(d, 1H); 7.47(m, 3H); 7.17(d, 1H); 3.76(m, 2H); 2.59(t, 2H); 2.26(s, 6H) | 0.46; 1.77; 2.14 | 354 | 353 | 355 | 100 |
| 93 | 8.29(bs, 1H); 8.18(d, 1H); 7.87(m, 2H); 7.75(t, 1H); 7.68(d, 1H); 7.48(m, 3H); 7.18(d, 1H); 3.80(bs, 2H), 2.76(bs, 6H); 1.09(bs, 6H) | 0.45; 1.87; 2.24 | 382 | 381 | 383 | 100 |
| 94 | 8.87(s, 1H); 8.67(bs, 1H); 8.25(s, 1H); 8.04(m, 2H); 7.88(m, 2H); 7.52(m, 4H); 7.10(d, 1H); 3.74(q, 2H); 2.46(t, 2H); 2.24(s, 3H); 1.92(m, 2H) | 0.45; 2.25; 2.50 | 418 | 417 | 419 | 99 |
| 95 | 8.87(s, 1H); 8.75(bs, 1H); 8.26(s, 1H); 8.06(m, 2H); 7.92(m, 2H); 7.54(m, 4H); 7.21(d, 1H); 3.765(q, 2H); 2.71(bs, 6H); 1.95(bs, 2H); 1.05(s, 6H) | 0.46; 2.38; 2.56 | 446 | 445 | 447 | 100 |
| 96 | 8.90(s, 1H); 8.51(t, 1H); 8.26(s, 1H); 8.05(t, 2H); 7.90(m, 2H); 7.54(m, 4H); 7.21 (d, 1H); 3.83(q.2H); 2.65(t, 2H); 2.29(s, 3H) | 0.46; 2.17; 2.41 | 404 | 403 | 405 | 100 |
| 97 | 8.87(s, 1H); 8.60(t, 1H); 8.26(s, 1H); 8.07(d, 1H); 8.02(d, 1H); 7.92(d, 1H); 7.84(d, 1H); 7.63-7.43(m, 4H); 7.22(d, 1H); 3.81(q, 2H); 2.86(bs, 2H); 2.68(bs, 4H); 1.06(t, 6H) | 0.46; 2.32; 2.49 | 432 | 431 | 433 | 100 |
| 98 | 8.52(bs, 1H); 8.20(d, 1H); 7.89(d, 1H); 7.73(t, 1H); 7.68(d, 1H); 7.62(d, 2H); 7.45(t, 1H); 7.29(d, 2H); 7.09(d, 1H); 6.57(s, 4H); 3.69(q, 2H); 2.88(m, 3H); 2.54(s, 3H); 2.01 (m, 2H); 1.23(d, 6H) | 0.44; 2.38; 2.53 | 374 | 373 | 375 | 92 |
| 99 | 8.40(bs, 1H); 8.24(s, 1H); 7.91(d, 1H); 7.74(t, 1H); 7.69(t, 1H); 7.63(d, 2H); 7.46(t, 1H); 7.30(d, 2H); 7.09(d, 1H); 6.60(s, 3H); 3.73(m, 2H); 3.06(m, 2H); 2.95(m, 4H); 2.90(m, 1H); 2.08(bs, 2H); 1.20(d, 6H); 1.17(t, 6H) | 0.46; 2.34; 2.59 | 402 | 401 | 403 | 100 |
| 100 | 8.33(bs, 1H); 8.17(d, 1H); 7.79(d, 1H); 7.72(m, 2H); 7.61(d, 2H); 7.44(t, 1H); 7.29(d, 2H); 7.09(d, 1H); 6.58(s, 3.5H); 3.87(bs, 2H); 2.96(t, 2H); 2.91(m, 1H); 2.55(s, 6H); 1.22(d, 6H) | 0.45; 2.18; 2.45 | 360 | 359 | 361 | 100 |
| 101 | 8.33(bs, 2H); 8.03(d, 1H); 7.73(dd, 1H); 7.66(s, 1H); 7.60(d, 1H); 7.42(d, 1H); 7.13(t, 1H); 6.82(d, 1H); 3.63(q, 2H); 2.39(t, 2H); 2.21(s, 6H); 1.83(m, 2H) | 0.46; 2.07 | 372 | 371 | 373 | 98 |
| 102 | 9.8(bs, 1H); 8.47(t, 1H); 8.38(s, 1H); 8.08(d, 1H); 7.76(dd, 1H); 7.67(s, 1H); 7.61(d, 1H); 7.44(d, 1H); 7.14(t, 1H); 6.86(d, 1H); 3.70(q, 2H); 3.08(bs, 6H); 2.06(bs, 2H); 1.18(t, 6H) | 0.45; 2.17 | 400 | 399 | 401 | 98 |
| 103 | 8.36(d, 1H); 8.23(t, 1H); 8.03(d, 1H); 7.74(dd, 1H); 7.62(s, 1H); 7.60(d, 1H); 7.41(d, 1H); 7.13(dd, 1H); 6.82(d, 1H); 3.72(q, 2H); 2.57(t, 2H); 2.25(s, 6H) | 0.45; 2.00 | 358 | 357 | 359 | 100 |
| 104 | 8.31(bs, 2H); 8.04(d, 1H); 7.74(dd, 1H(; 7.87(d, 1H); 7.60(d, 1H); 7.38(d, 1H); 7.13(dd, 1H); 6.83(d, 1H); 3.68(q, 2H); 2.74(bs, 2H); 2.62(bs, 4H); 1.03(t.6H) | 0.45; 2.12 | 386 | 385 | 387 | 100 |
| 105 | 8.33(bs, 1H); 8.20(d, 1H); 8.04(d, 1H); 7.73(t, 1H); 7.65(d, 1H); 7.59(d, 1H); 7.45(m, 2H); 7.13(t, 1H); 6.84(d, 1H); 6.57(s, 2.5H); 3.68(q, 2H); 2.86(t, 2H); 2.53(s, 6H); 1.99(m, 2H) | 0.45; 2.00 | 338 | 337 | 339 | 97 |
| 106 | 8.39(bs, 1H); 8.22(d, 1H); 8.05(d, 1H); 7.72(t, 1H); 7.66(d, 1H); 7.59(d, 1H); 7.45(t, 1H); 7.43(bs, 1H); 7.13(t, 1H); 6.85(d, 1H); 6.59(s, 4H); 3.70(bs, 2H); 3.07(m, 2H); 3.00(q, 4H); 2.04(m.2H); 1.15(t, 6H) | 0.44; 2.09 | 366 | 365 | 367 | 95 |

TABLE 2-continued

The analytical data of the prepared compounds

| Example | $^1$H-NMR | Rt [min] | MW calculated, monoisotopic | MW measured [−] | MW measured [+] | Purity % |
|---|---|---|---|---|---|---|
| 107 | 8.47(s, 1H); 8.35(t, 1H); 8.04(d, 1H); 7.84(dd, 1H); 7.58(m, 2H); 7.42(d, 1H); 7.13(t, 1H); 6.82(d, 1H); 3.62(q, 2H); 2.38(t, 2H); 2.20(s, 6H); 1.83(m, 2H) | 0.46; 1.83; 2.18 | 416 | 415 | 417 | 98 |
| 108 | 8.34(bs, 1H); 8.17(d, 1H); 8.06(d, 1H); 7.74(t, 1H); 7.66(d, 1H); 7.60(d, 1H); 7.46(d, 1H); 7.41(bs, 1H); 7.13(bs, 1H)6.84(d, 1H); 6.58(s, 4H); 3.85(bs, 2H); 2.97(bs, 2H); 2.53(s, 6H) | 0.44; 1.91 | 324 | 323 | 325 | 99 |
| 109 | 8.37(bs, 2H); 7.88(d, 1H); 7.74(dd, 1H); 7.66(s, 1H); 7.65(d, 2H); 7.29(d, 2H); 7.09(d, 1H); 8.56(s, 2.6H); 3.66(q, 2H); 2.76(t, 2H); 2.51(s, 3H); 2.46(s, 3H); 1.96(m, 2H) | 0.46; 2.11; 2.46 | 412 | 411 | 413 | 100 |
| 110 | 8.43(bs, 1H); 8.38(s, 1H); 7.89(d, 1H); 7.76-7.63(m, 4H); 7.29(d, 2H); 7.09(d, 1H); 6.56(s, 2.5H); 3.69(q, 2H); 2.90(t, 2H); 2.87(m, 4H); 2.50(s, 3H); 1.99(bs, 2H); 1.09(t, 6H) | 0.46; 2.23; 2.56 | 440 | 439 | 441 | 93 |
| 111 | 8.45(bs, 1H); 8.31(s, 1H); 7.89(d, 1H); 7.76-7.60(m, 4H); 7.30(d, 2H); 7.09(d, 1H); 6.57(s, 2H); 3.79(q, 2H); 2.93(t, 2H); 2.80(q, 4H); 1.08(t, 6H) | 0.46; 2.22; 2.52 | 426 | 425 | 427 | 95 |
| 112 | 8.40(bs, 1H); 8.34(s.1H); 7.90(d, 1H); 7.69(m, 4H); 7.29(d, 2H); 7.09(d, 1H); 6.57(s, 2.6H); 3.83(bs, 2H); 2.89(bs, 2H); 2.50(s, 9H) | 0.46; 2.01; 2.41 | 398 | 397 | 399 | 100 |
| 113 | 8.21(s, 1H); 7.87(d, 1H); 7.74(m, 3H); 7.46(m, 2H); 7.17(d, 1H); 4.88(bs, 1H); 4.08(bs, 1H); 3.93(bs, 1H); 2.82(m, 1H); 2.57(m, 5H); 2.00(m, 4H); 1.71(bs, 4H) | 2.66 | 454 | 453 | 455 | 93 |
| 114 | 8.03(bs, 1H); 7.81(m, 2H); 7.59(s, 1H); 7.50(bs, 1H); 7.44(t, 1H); 7.11(d.1H); 7.10(s, 1H); 3.90(s, 6H); 3.66(q, 2H); 2.71(bs, 2H); 2.44(s, 6H); 1.95(m, 2H) | 2.44 | 428 | 427 | 429 | 98 |
| 115 | 9.90(bs, 1H); 8.17(bs, 1H); 7.86(m, 1H); 7.80(s, 1H); 7.66(s, 1H); 7.54(bs, 1H); 7.46(q, 1H); 7.10(m, 2H); 3.90(s, 6H); 3.70(q, 2H); 32.09(bs, 6H); 2.07(bs, 2H); 1.03(bs, 6H) | 2.53 | 456 | 455 | 457 | 98 |
| 116 | 8.07(bs, 1H); 7.83(m, 2H); 7.57(s, 1H); 7.50(bs, 1H); 7.47(t, 1H); 7.11(d, 1H); 7.10(s, 1H); 6.58(s, 3.5H); 3.89(s, 6H); 3.85(bs, 2H); 2.92(bs, 2H); 2.50(s, 6H) | 0.48; 2.36 | 414 | 413 | 415 | 98 |
| 117 | 10.32(bs, 1H); 8.37(bs, 1H); 7.87(m, 2H); 7.70(s, 1H); 7.54(bs, 1H); 7.47(q, 1H); 7.13(t, 2H); 4.01(bs, 2H); 3.91(s, 6H); 3.40(bs, 6H); 1.25(bs, 6H) | 0.45; 2.30; 2.45 | 442 | 441 | 443 | 100 |
| 118 | 7.85(m, 2H); 7.78(d, 1H); 7.61(s, 1H); 7.54-7.39(m, 2H); 7.09(t, 2H); 3.89(s, 6H); 3.58(q, 2H); 1.72(m, 2H); 1.02(t, 3H) | 3.62 | 385 | 384 | 386 | 98 |
| 119 | 8.35(t, 1H); 8.19(s, 1H); 7.96(m, 5H); 7.73(m, 2H); 7.48(t, 1H); 7.33(d, 1H); 3.68(q, 2H); 3.26(s, 3H); 2.43(t, 2H); 2.23(s, 6H); 1.87(m, 2H) | 0.45; 1.95 | 410 | 409 | 411 | 100 |
| 120 | 8.21(d, 1H); 7.87(d, 1H); 7.75(m, 3H); 7.47(m, 2H); 7.17(d, 1H); 4.88(bs, 1H); 4.10(m, 1H); 3.93(bs, 1H); 2.82(dd, 1H); 2.54(m, 5H); 2.00(m, 4H); 1.71(bs, 4H) | 2.62 | 454 | 453 | 455 | 97 |
| 121 | 8.22(bs, 1H); 8.19(s, 1H); 7.97(m, 5H); 7.76(t, 1H); 7.70(d, 1H); 7.48(t, 1H); 7.33(d, 1H); 3.77(q, 2H); 3.25(s, 3H); 2.60(t, 2H); 2.27(s, 6H) | 0.39; 1.78 | 396 | 395 | 397 | 100 |
| 122 | 8.27(d, 1H); 8.26(s, 1H); 7.95(m, 5H); 7.70(m, 2H); 7.50(t, 1H); 7.33(d, 1H); 3.63(q, 2H); 3.25(s, 3H); 1.74(m, 2H); 1.00(t.3H) | 2.76 | 367 | 366 | 368 | 95 |
| 123 | 8.36(bs, 2H); 7.89(d, 1H); 7.74(d, 1H); 7.67(d, 1H); 7.61(d, 2H); 7.29(d, 2H); 7.07(d, 1H); 6.56(s, 3H); 3.67(q, 2H); 2.91(m, 1H); 2.76(m, 2H), 2.46(s, 6H); 1.98(m, 2H); 1.21(d, 6H) | 2.77 | 408 | 407 | 409 | 97 |
| 124 | 8.41(t, 1H); 8.37(s, 1H); 7.90(d, 1H); 7.74(dd, 1H); 7.68(d, 1H); 7.61(d, 2H); 7.29(d, 2H); 7.07(d, 1H); 6.56(s, 2H); 3.69(q, 2H); 2.91(m, 3H); 2.84(m, 4H); 1.99(m, 2H); 1.22(d, 6H); 1.09(t, 6H) | 2.88 | 436 | 435 | 437 | 97 |
| 125 | 8.37(t, 1H); 8.33(d, 1H); 7.90(d, 1H); 7.74(dd, 1H); 7.68(d, 1H); 7.61(d, 2H); 7.29(d, 2H); 7.08(d, 1H); 6.57(s, 2.8H); 3.83(q, 2H); 2.92(m, 1H); 2.88(m, 2H); 2.47(s, 6H); 1.22(d, 6H) | 2.73 | 394 | 393 | 395 | 97 |
| 126 | 8.49(bs, 1H); 8.31(d, 1H); 7.90(d, 1H); 7.75(dd, 1H); 7.68(d, 1H); 7.59(d, 2H); 7.29(d, 2H); 7.07(d, 1H); 6.57(s, 2.4H); 3.82(q, 2H); 2.97(m, 3H); 2.84(m, 4H); 1.22(d, 6H); 1.10(t, 6H) | 2.80 | 422 | 421 | 423 | 90 |
| 127 | 8.27(bs, 1H); 8.08(dd, 1H); 7.88(d, 1H); 7.74(m, 1H); 7.67(m, 1H); 7.61(d, 2H); 7.29(d, 2H); 7.07(d, 1H); 6.56(s, 3H); 3.68(q, 2H); 2.91(m, 1H); 2.81(t, 2H); 2.49(s, 6H); 1.98(t, 2H); 1.22(d, 6H) | 2.63 | 392 | 391 | 393 | 96 |

TABLE 2-continued

The analytical data of the prepared compounds

| Example | ¹H-NMR | Rt [min] | MW calculated, monoisotopic | MW measured [−] | MW measured [+] | Purity % |
|---|---|---|---|---|---|---|
| 128 | 8.27(bs, 1H); 8.04(d, 1H); 7.89(d, 1H); 7.72(m, 1H); 7.67(m, 1H); 7.61(d, 2H); 7.29(d, 2H); 7.07(d, 1H); 6.57(s, 2.7H); 3.84(m, 2H); 2.89(m, 3H); 2.47(s, 6H); 1.22(d, 6H) | 2.51; 2.59 | 378 | 377 | 379 | 95 |
| 129 | 8.36(bs, 1H); 8.02(d, 1H); 7.89(d, 1H); 7.73(m, 1H); 7.66(m, 1H); 7.60(d, 2H); 7.30(d, 2H); 7.08(d, 1H); 6.59(s, 3H); 3.83(m, 2H); 3.01(m, 3H); 2.88(m, 4H); 1.22(d, 6H); 1.12(t, 6H) | 2.67 | 406 | 405 | 407 | 90 |
| 130 | 8.37(bs, 2H); 7.96(m, 5H); 7.77(d, 1H); 7.69(d, 1H); 7.31(d, 1H); 3.66(q, 2H); 3.24(s, 3H); 2.43(m, 2H); 2.23(s, 6H); 1.86(m, 2H) | 0.44; 1.89; 2.07 | 444 | 443 | 445 | 94 |
| 131 | 8.48(bs, 1H); 8.39(d, 1H); 7.98(m, 5H); 7.77(dd, 1H); 7.71(d, 1H); 7.31(d, 1H); 6.54(s 0.6H); 3.70(q, 2H); 3.24(s, 3H); 2.81(m, 6H); 1.95(m, 2H); 1.07(t, 6H) | 0.45; 2.04; 2.17 | 472 | 471 | 473 | 96 |
| 132 | 8.39(d, 1H); 8.29(t, 1H); 7.95(m, 5H); 7.77(dd, 1H); 7.70(d, 1H); 7.31(d, 1H); 3.75(q, 2H); 3.24(s, 3H); 2.59(t, 2H); 2.26(s, 6H) | 0.44; 1.91; 2.06 | 430 | 429 | 431 | 95 |
| 133 | 8.57(bs, 1H); 8.35(d, 1H); 7.95(m, 5H); 7.78(dd, 1H); 7.71(d, 1H); 7.33(d, 1H); 6.58(s, 2.2H); 3.84(q, 2H); 3.24(s, 3H); 3.00(t, 2H); 2.86(q, 4H); 1.10(t, 6H) | 2.18 | 458 | 457 | 459 | 99 |

Biological Methods

Biochemical Activity Assays

FLT3(ITD) biochemical assays were performed on two different assay system platforms, using Transcreener® ADP Assay FP method (BellBrook Labs, Madison, Wis., US) and IMAP® FP biochemical activity assays (Molecular Devices, Sunnyvale, Calif., US).

In each case the assays were performed in low protein binding, black, round bottom 384-well plates type 3676 (Corning, One Riverfront Plaza, NY, US). Kinase inhibitor compounds were dissolved in 100% DMSO to 5 mM and then we prepared serial dilutions in order to determine $IC_{50}$ values.

In the TranScreener® FLT3(ITD) assay we used the following materials in the following final concentrations for the reaction: 8 nM FLT3(ITD) (ProQinase, Freiburg, Germany), 0.05 mg/ml Poly Glu-Tyr peptide (Sigma-Aldrich, Budapest, Hungary) as a substrate, 20 mM HEPES pH 7.5 (Sigma-Aldrich), 1 mM DTT (Sigma-Aldrich), 3 mM $MgCl_2$ (Sigma-Aldrich), 3 mM $MnCl_2$ (Sigma-Aldrich), and 0.01 V % V Tween20 (Sigma-Aldrich) as a detergent. The kinase reaction had started by the addition of 2 μl 5× enzyme, and the reaction had been progressing in the volume of 10 μl for 1 hour at room temperature. The reaction has been stopped by adding 10 μl Transcreener® Stop and Detection Solution and had been incubated for additional 1 hour. The solution contained in every case 20 mM HEPES pH 7.5, 40 mM EDTA, 0.02 V/V % Brij35 and 3 nM ADP Alexa633 Tracer. The ADP antibody concentration was 2.08 μg/ml according to the $K_{mapp}$ value which was 1 μM. Then fluorescence polarization and fluorescence intensity was measured using Analyst GT Multimode Reader (Molecular Devices).

In the IMAP FP assay the reaction conditions were the following: 16-45 nM FLT3(ITD) (ProQinase), 400 nM 5TAMRA-GEEPLYWSFPAKKK-NH2 dyed peptide for substrate (Genecust, Dudelenge, Luxembourg), 20 mM HEPES pH 8, 1 mM DTT, 10 mM $MgCl_2$, 2 mM $MnCl_2$, and 0.01V % V Brij35 detergent (Sigma-Aldrich). The ATP concentration was 5.1 μM. The kinase reaction had started by the addition of 2 μl 5× enzyme, and the reaction had been progressing in the volume of 10 μl for 1 hour at room temperature and then was terminated by adding 10 μl IMAP Detection mixture. Fluorescence polarization and fluorescence intensity was measured using Analyst GT Multimode Reader (Molecular Devices) after 1.5 hour of incubation on room temperature.

Cell Line and Cell Viability Assays

The cell line used was MV4-11, obtained from ATCC (American Type Culture Collection, Manassas, Va., US). It is a biphenotypic B myelomonocytic leukemia macrophage cell line which expresses exclusively the mutated form of FLT3, the above described FLT3(ITD). Using MV4-11 cell line, we performed cell viability assays, where the kinase inhibitors were incubated with the cells for 72 hours on 37° C./98.6° F. in 5 V/V % CO2 atmosphere in serial dilutions in order to determine $IC_{50}$ values. For the detection of the percentage of the survived cells we used CellTiter Glo® Luminescent Cell Viability Assay (Promega, Madison, Wis., US). The assays were performed according to the manufacturer's instructions except for the volumes used: we added 33.3 μl CellTiter Glo® Reagent to 66.6 μl of media containing the treated cells. Luminescence was measured using Analyst GT Multimode Reader (Molecular Devices).

In all cases of the biochemical and cellular assays we used Microsoft Excel (Microsoft Corp., Redmond, Wash., US) for data processing and for generating $IC_{50}$ curves we used XLfit curve fitting add-in software (Guildford, UK) for Microsoft Office Excel.

Biological Results

The enzyme assay was performed using TranScreener® (BellBrook Labs) IMAP FP® (Molecular Devices) biochemical enzyme activity assay systems. Compounds were original molecules produced by Vichem Chemie Research Ltd. and were described above in detail. Primary screening was performed in one concentration (10 μM) of the compounds. Hits were subsequently measured in a twelve-point serial dilution set in order to determine compound specific $IC_{50}$ values. The assay conditions were described above. In each case we used Sunitinib, marketed as Sutent® by Pfizer, which is a broad-spectrum kinase inhibitor and a known inhibitor of FLT3 as well. Kinase assays were considered as acceptable when the Z prime value was >0.5. In each case the average of the parallel measurements is shown.

TABLE 3

IC$_{50}$ values of presented hit derivatives in biochemical activity assay.

| Example | Average IC$_{50}$ values on FLT3(ITD) in μM | standard deviation |
|---|---|---|
| 1 | 1.913 | 0.035 |
| 2 | 10.000 | 0.000 |
| 3 | 7.674 | 3.289 |
| 5 | 13.801 | 9.959 |
| 6 | 1.417 | 0.282 |
| 7 | 1.394 | 0.289 |
| 11 | 1.957 | 0.703 |
| 12 | 5.110 | 1.607 |
| 15 | 1.545 | 0.326 |
| 16 | 3.076 | 0.596 |
| 17 | 8.611 | 0.000 |
| 18 | 2.280 | 0.979 |
| 20 | 2.394 | 0.729 |
| 21 | 2.258 | 1.199 |
| 22 | 4.199 | 1.222 |
| 23 | 4.759 | 0.767 |
| 37 | 8.531 | 2.078 |
| 39 | 10.000 | 0.000 |
| 55 | 9.676 | 0.000 |
| 57 | 1.996 | 0.249 |
| 68 | 0.811 | 0.224 |
| 69 | 2.124 | 1.311 |
| 75 | 0.074 | 0.045 |
| 76 | 3.696 | 0.588 |
| 77 | 1.764 | 0.885 |
| 78 | 4.496 | 3.504 |
| 79 | 6.317 | 3.023 |
| 81 | 1.703 | 0.640 |
| 82 | 1.641 | 0.706 |
| 83 | 0.134 | 0.040 |
| 84 | 2.333 | 0.224 |
| 85 | 0.950 | 0.358 |
| 88 | 0.461 | 0.000 |
| 92 | 9.080 | 1.302 |
| 93 | 3.251 | 0.118 |
| 98 | 2.018 | 0.000 |
| 99 | 1.507 | 0.018 |
| 100 | 0.258 | 0.097 |
| 101 | 6.690 | 1.351 |
| 102 | 10.694 | 0.982 |
| 103 | 2.931 | 1.051 |
| 104 | 2.305 | 0.309 |
| 105 | 7.783 | 0.000 |
| 107 | 10.000 | 0.000 |
| 108 | 6.294 | 0.000 |
| 109 | 2.385 | 0.000 |
| 110 | 5.620 | 0.000 |
| 111 | 6.953 | 0.000 |
| 112 | 1.264 | 0.000 |
| 119 | 1.511 | 0.043 |
| 121 | 0.326 | 0.005 |
| 122 | 3.823 | 0.000 |
| 123 | 1.271 | 0.973 |
| 124 | 2.970 | 2.578 |
| 125 | 0.412 | 0.411 |
| 126 | 1.404 | 1.701 |
| 127 | 1.262 | 1.223 |
| 128 | 0.582 | 0.702 |
| 129 | 0.874 | 1.046 |
| 130 | 0.873 | 0.882 |
| 131 | 1.982 | 1.087 |
| 132 | 0.246 | 0.212 |
| 133 | 0.440 | 0.316 |

The cell viability assays were performed on the MV4-11 cell line using Promega's CellTiter-Glo® Luminescent Cell Viability Assay method following the instructions of the supplier except the conditions described above. Primary screening was performed in one concentration (10 μM) of the compounds. Hits were subsequently measured in a ten-point serial dilution set in order to determine compound specific IC$_{50}$ values.

TABLE 4

IC$_{50}$ values of presented hit derivatives in cell viability assay.

| Example | Average IC$_{50}$ values on MV4-11 cells in μM | Standard deviation |
|---|---|---|
| 3 | 0.1844 | 0.0000 |
| 7 | 0.8284 | 0.0000 |
| 10 | 2.3221 | 2.1380 |
| 11 | 2.3399 | 1.3169 |
| 12 | 1.1613 | 0.2574 |
| 13 | 2.7750 | 0.4783 |
| 14 | 10.2472 | 6.7842 |
| 15 | 0.3915 | 0.0587 |
| 18 | 1.8553 | 1.0508 |
| 20 | 0.4379 | 0.1696 |
| 21 | 1.8513 | 1.2464 |
| 22 | 1.0421 | 0.0982 |
| 23 | 2.1214 | 0.0899 |
| 29 | 4.8742 | 1.6221 |
| 32 | 1.2649 | 0.0353 |
| 35 | 2.8475 | 2.0202 |
| 36 | 1.0507 | 0.0000 |
| 39 | 1.0643 | 0.3749 |
| 42 | 6.4081 | 5.8036 |
| 46 | 9.5231 | 1.3983 |
| 52 | 4.2082 | 1.3561 |
| 53 | 4.5406 | 0.5619 |
| 54 | 10.1229 | 2.3004 |
| 57 | 0.9794 | 1.2188 |
| 61 | 1.8149 | 1.4286 |
| 65 | 6.6102 | 3.9400 |
| 68 | 0.3178 | 0.0107 |
| 69 | 0.9897 | 0.8505 |
| 71 | 2.7308 | 1.2503 |
| 74 | 4.9484 | 0.0000 |
| 75 | 0.0231 | 0.0327 |
| 76 | 3.4946 | 2.7186 |
| 77 | 0.7257 | 0.0181 |
| 78 | 0.7235 | 0.1656 |
| 79 | 1.4264 | 0.0000 |
| 80 | 1.5463 | 1.4503 |
| 81 | 0.5095 | 0.0160 |
| 82 | 0.4793 | 0.0666 |
| 83 | 0.1215 | 0.0153 |
| 84 | 0.9225 | 0.0000 |
| 85 | 0.3291 | 0.0623 |
| 86 | 1.1220 | 0.0330 |
| 87 | 2.8622 | 0.0000 |
| 88 | 0.2491 | 0.0605 |
| 89 | 1.4336 | 0.0000 |
| 91 | 2.7801 | 0.2425 |
| 92 | 1.5429 | 1.0002 |
| 93 | 1.0438 | 0.0000 |
| 95 | 1.3899 | 0.0274 |
| 96 | 2.3720 | 1.2557 |
| 97 | 1.4636 | 0.2658 |
| 98 | 0.5771 | 0.0625 |
| 99 | 0.7892 | 0.2361 |
| 100 | 0.1500 | 0.1744 |
| 101 | 1.9627 | 1.1799 |
| 102 | 2.8080 | 0.9983 |
| 103 | 0.7504 | 0.4937 |
| 104 | 0.6538 | 0.0000 |
| 105 | 1.4767 | 0.0000 |
| 106 | 2.1965 | 0.0000 |
| 107 | 0.3674 | 0.0000 |
| 108 | 0.5039 | 0.0000 |
| 109 | 0.2845 | 0.0000 |
| 110 | 0.8441 | 0.0000 |
| 111 | 0.0955 | 0.0000 |
| 112 | 0.0038 | 0.0000 |
| 113 | 9.6182 | 0.0000 |
| 115 | 1.9982 | 0.0000 |
| 119 | 0.2951 | 0.0000 |
| 120 | 13.7051 | 0.0000 |
| 121 | 0.0562 | 0.0000 |
| 122 | 0.3974 | 0.0000 |
| 123 | 0.3994 | 0.3055 |
| 124 | 0.7914 | 0.4381 |
| 125 | 0.0255 | 0.0015 |

TABLE 4-continued

IC$_{50}$ values of presented hit derivatives in cell viability assay.

| Example | Average IC$_{50}$ values on MV4-11 cells in μM | Standard deviation |
|---|---|---|
| 130 | 0.1039 | 0.0947 |
| 132 | 0.0080 | 0.0077 |

In order to define the selectivity profile of styryl quinazoline derivatives enclosed in this invention we chose a both structurally and bioactive representative compound (Example 11). The measurements were performed by DiscoveRx Corp. (Fremont, Calif., US). The compound was tested in the scanMAX™ Kinase Assay Panel which covers more than 80% of the human protein kinome. It's an activation-state specific assay in which 456 kinases were tested using the compound at the concentration of 5 μM. The results are represented here as the percentage of activity loss caused by the compound.

TABLE 5

Selectivity panel results of Example 11

| Kinase | Specification | Kinase Family | Inhibition (%) |
|---|---|---|---|
| FLT3(D835H) | TK | PDGFR | 97.1 |
| FLT3(ITD) | TK | PDGFR | 95.8 |
| FLT3(N841I) | TK | PDGFR | 96 |
| FLT3(D835Y) | TK | PDGFR | 94.6 |
| FLT3 | TK | PDGFR | 81 |
| FLT3(K663Q) | TK | PDGFR | 80 |
| CSNK1A1 | CK1 | CK1 | 77 |
| RIOK3 | Atypical | RIO | 74 |
| GAK | Other | NAK | 65 |
| MEK5 | STE | STE7 | 64 |
| RIOK1 | Atypical | RIO | 63 |
| SRMS | TK | Src | 62 |
| TYK2(JH1domain-catalytic) | TK | JakA | 60 |
| KIT(A829P) | TK | PDGFR | 60 |
| BMPR1B | TKL | STKR | 59 |
| EGFR(T790M) | TK | EGFR | 56 |
| ULK1 | Other | ULK | 56 |
| CSNK1E | CK1 | CK1 | 52 |
| FLT3(R834Q) | TK | PDGFR | 52 |
| PFCDPK1(P. falciparum) | Pathogen | P. Falciparum | 50 |
| CSNK1D | CK1 | CK1 | 49 |
| CSNK2A2 | Other | CK2 | 49 |
| VRK2 | CK1 | VRK | 47 |
| KIT(V559D) | TK | PDGFR | 46 |
| PIM2 | CAMK | PIM | 46 |
| PDGFRB | TK | PDGFR | 45 |
| CSNK1A1L | CK1 | CK1 | 45 |
| MEK4 | STE | STE7 | 44 |
| SGK | AGC | SGK | 44 |
| KIT(D816V) | TK | PDGFR | 43 |
| TAOK3 | STE | STE20 | 43 |
| IKK-epsilon | Other | IKK | 43 |
| RPS6KA4(Kin.Dom.2-C-terminal) | AGC | RSK | 42 |
| PIK3CA(M1043I) | LIPID | PI3K | 42 |
| TAOK1 | STE | STE20 | 41 |
| PIK3CA(H1047Y) | LIPID | PI3K | 41 |
| MKNK2 | CAMK | MAPKAPK | 40 |
| ALK | TK | Alk | 40 |
| p38-gamma | CMGC | MAPK | 40 |
| ULK3 | Other | ULK | 39 |
| DCAMKL1 | CAMK | DCAMKL | 39 |
| PIK3CA(E545A) | LIPID | PI3K | 39 |
| INSR | TK | InsR | 38 |
| PDPK1 | AGC | PKB | 38 |
| RSK2(Kin.Dom.1-N-terminal) | AGC | RSK | 37 |
| ABL1(F317L)-nonphosphorylated | TK | Abl | 36 |
| ABL1(F317I)-nonphosphorylated | TK | Abl | 36 |
| TRKC | TK | Trk | 36 |
| PIK3C2B | LIPID | PI3K | 36 |
| BIKE | Other | NAK | 35 |
| BLK | TK | Src | 35 |
| PIK3CD | LIPID | PI3K | 35 |
| FLT3-autoinhibited | TK | PDGFR | 34 |
| EGFR(L858R, T790M) | TK | EGFR | 34 |
| ABL1(F317I)-phosphorylated | TK | Abl | 33 |
| SRC | TK | Src | 32 |
| GRK1 | AGC | GRK | 32 |
| ABL1(H39P)-nonphosphorylated | TK | Abl | 31 |
| KIT(L576P) | TK | PDGFR | 31 |
| TNIK | TK | Ack | 31 |
| EPHA3 | TK | Eph | 31 |
| MARK2 | CAMK | CAMKL | 31 |
| PIK3CA(C420R) | LIPID | PI3K | 31 |
| PKAC-alpha | AGC | PKA | 31 |
| PIPSK1A | LIPID | PIP | 29 |
| MAP3K2 | STE | STE11 | 29 |
| FYN | TK | Src | 29 |
| KIT | TK | PDGFR | 28 |
| FGFR2 | TK | FGFR | 28 |
| BMX | TK | Tec | 28 |
| MKK7 | STE | STE7 | 28 |
| MAP4K2 | STE | STE20 | 26 |
| MYLK | CAMK | MLCK | 26 |
| TRKA | TK | Trk | 26 |
| PIK3CA(Q546K) | LIPID | PI3K | 26 |
| ABL1(F317L)-phosphorylated | TK | Abl | 24 |
| STK33 | CAMK | CAMK-Unique | 24 |
| EGFR(G719C) | TK | EGFR | 23 |
| MERTK | TK | Axl | 22 |
| RIOK2 | Atypical | RIO | 22 |
| CTK | TK | Csk | 22 |
| PLK3 | Other | PLK | 22 |
| AKT1 | AGC | AKT | 22 |
| ABL1-phosphorylated | TK | Abl | 21 |
| MELK | CAMK | CAMKL | 21 |
| RSK1(Kin.Dom.2-C-terminal) | AGC | RSK | 21 |
| PKNB(M. tuberculosis) | Pathogen | MTB | 20 |
| PLK2 | Other | PLK | 20 |
| RIPK4 | TKL | RIPK | 20 |
| ROCK2 | AGC | DMPK | 20 |
| MEK6 | STE | STE7 | 20 |
| PIK3C2G | LIPID | PI3K | 20 |
| ABL1(H396P)-phosphorylated | TK | Abl | 19 |
| JNK1 | CMGC | MAPK | 19 |
| HASPIN | Other | Haspin | 19 |
| CSNK1G1 | CK1 | CK1 | 19 |
| RSK3(Kin.Dom.1-N-terminal) | AGC | RSK | 19 |
| JAK2(JH1domain-catalytic) | TK | JakA | 18 |
| EGFR(S752-I759del) | TK | EGFR | 18 |
| OSR1 | STE | STE20 | 18 |
| TLK1 | Other | TLK | 18 |
| PAK3 | STE | STE20 | 17 |
| HUNK | CAMK | CAMKL | 17 |
| AKT3 | AGC | AKT | 17 |
| ABL1(E255K)-phosphorylated | TK | Abl | 16 |
| AXL | TK | Axl | 16 |
| EGFR(L747-S752del, P753S) | TK | EGFR | 16 |
| RIPK5 | TKL | RIPK | 16 |
| PRKG1 | AGC | PKC | 16 |
| ABL1(T315I)-nonphosphorylated | TK | Abl | 15 |
| ABL1(T315I)-phosphorylated | TK | Abl | 15 |
| KIT(D816H) | TK | PDGFR | 15 |
| LKB1 | CAMK | CAMKL | 15 |
| RET(M918T) | TK | Ret | 15 |
| CSF1R-autoinhibited | TK | PDGFR | 15 |
| ADCK3 | Atypical | ABC1 | 15 |
| GRK7 | AGC | GRK | 15 |
| CDC2L2 | CMGC | CDK | 15 |
| CSNK1G3 | CK1 | CK1 | 14 |
| NDR2 | AGC | NDR | 14 |
| RSK4(Kin.Dom.2-C-terminal) | AGC | RSK | 14 |
| CAMK1D | CAMK | CAMK1 | 13 |
| PLK4 | Other | PLK | 13 |
| FGR | TK | Src | 13 |

TABLE 5-continued

Selectivity panel results of Example 11

| Kinase | Specification | Kinase Family | Inhibition (%) |
|---|---|---|---|
| LIMK2 | TKL | LISK | 13 |
| ASK1 | STE | STE11 | 13 |
| ABL1(M351T)-phosphorylated | TK | Abl | 12 |
| PDGFRA | TK | PDGFR | 12 |
| TBK1 | Other | IKK | 12 |
| FGFR3 | TK | FGFR | 12 |
| RET(V804L) | TK | Ret | 12 |
| RSK4(Kin.Dom.1-N-terminal) | AGC | RSK | 12 |
| MAPKAPK5 | CAMK | MAPKAPK | 12 |
| ABL1-nonphosphorylated | TK | Abl | 11 |
| FLT1 | TK | VEGFR | 11 |
| STK35 | Other | NKF4 | 11 |
| DAPK3 | CAMK | DAPK | 11 |
| NEK5 | Other | NEK | 11 |
| PAK7 | STE | STE20 | 11 |
| MEK1 | STE | STE7 | 11 |
| MST3 | STE | STE20 | 11 |
| PIK3CA | LIPID | PI3K | 11 |
| NEK1 | Other | NEK | 10 |
| DMPK | AGC | DMPK | 10 |
| p38-delta | CMGC | MAPK | 10 |
| DYRK1A | CMGC | DYRK | 9 |
| JNK3 | CMGC | MAPK | 9 |
| DAPK1 | CAMK | DAPK | 9 |
| ERK8 | CMGC | MAPK | 9 |
| PIK3CA(I800L) | LIPID | PI3K | 9 |
| RIPK1 | TKL | RIPK | 9 |
| CHEK2 | CAMK | RAD53 | 9 |
| PRKD2 | AGC | PKC | 9 |
| PKAC-beta | AGC | PKA | 9 |
| EPHA2 | TK | Eph | 9 |
| DDR2 | TK | DDR | 8 |
| LATS2 | AGC | NDR | 8 |
| NEK2 | Other | NEK | 8 |
| PIK3CG | LIPID | PI3K | 8 |
| PKN1 | AGC | PKN | 8 |
| ITK | TK | Tec | 8 |
| SIK | CAMK | CAMKL | 8 |
| AURKC | Other | AUR | 7 |
| PRKR | Other | PEK | 7 |
| RIPK2 | TKL | RIPK | 7 |
| FRK | TK | Src | 7 |
| MAP3K1 | STE | STE11 | 7 |
| PFTK1 | CMGC | CDK | 7 |
| CLK4 | CMGC | CLK | 6 |
| FLT4 | TK | VEGFR | 6 |
| DRAK1 | CAMK | DAPK | 6 |
| ROCK1 | AGC | DMPK | 6 |
| CDK4-cyclinD3 | CMGC | CDK | 6 |
| PRKCQ | AGC | PKC | 6 |
| AURKA | Other | AUR | 5 |
| ABL2 | TK | Abl | 5 |
| NEK4 | Other | NEK | 5 |
| PIM1 | CAMK | PIM | 5 |
| EGFR(L747-E749del, A750P) | TK | EGFR | 4 |
| HPK1 | STE | STE20 | 4 |
| RET | TK | Ret | 4 |
| TTK | Other | TTK | 4 |
| ACVR2B | TKL | STKR | 4 |
| BRSK1 | CAMK | CAMKL | 4 |
| HCK | TK | Src | 4 |
| DMPK2 | AGC | DMPK | 4 |
| TAOK2 | STE | STE20 | 4 |
| ABL1(Y253F)-phosphorylated | TK | Abl | 3 |
| TAK1 | TKL | MLK | 3 |
| NEK6 | Other | NEK | 3 |
| TNNI3K | Other | Other | 3 |
| ZAP70 | TK | Syk | 3 |
| ABL1(Q252H)-nonphosphorylated | TK | Abl | 2 |
| CDKL5 | CMGC | CDKL | 2 |
| RPS6KA5(Kin.Dom.2-C-terminal) | AGC | RSK | 2 |
| SYK | TK | Syk | 2 |
| FAK | TK | Fak | 2 |
| PIP5K2C | LIPID | PIP | 2 |
| BRK | TK | Src | 2 |
| CDK3 | CMGC | CDK | 2 |
| ERK5 | CMGC | MAPK | 2 |
| RET(V804M) | TK | Ret | 1 |
| PAK2 | STE | STE20 | 1 |
| CDC2L5 | CMGC | CDK | 1 |
| CDM-cyclinD1 | CMGC | CDK | 1 |
| PCTK2 | CMGC | CDK | 1 |
| IRAK3 | TKL | IRAK | 1 |
| KIT(V559D, V654A) | TK | PDGFR | 0 |
| AAK1 | Other | NAK | 0 |
| ABL1(Q252H)-phosphorylated | TK | Abl | 0 |
| AURKB | Other | AUR | 0 |
| CIT | AGC | DMPK | 0 |
| CLK1 | CMGC | CLK | 0 |
| CLK2 | CMGC | CLK | 0 |
| EPHA1 | TK | Eph | 0 |
| EPHB6 | TK | Eph | 0 |
| HIPK1 | CMGC | DYRK | 0 |
| HIPK4 | CMGC | DYRK | 0 |
| IRAK1 | TKL | IRAK | 0 |
| JAK3(JH1domain-catalytic) | TK | JakA | 0 |
| JNK2 | CMGC | MAPK | 0 |
| KIT(V559D, T670I) | TK | PDGFR | 0 |
| LCK | TK | Src | 0 |
| MAP4K4 | STE | STE20 | 0 |
| MINK | STE | STE20 | 0 |
| SIK2 | CAMK | CAMKL | 0 |
| SLK | STE | STE20 | 0 |
| SNARK | CAMK | CAMKL | 0 |
| STK16 | Other | NAK | 0 |
| VEGFR2 | TK | VEGFR | 0 |
| YSK4 | STE | STE20 | 0 |
| ACVR1 | TKL | STKR | 0 |
| BMPR2 | TKL | STKR | 0 |
| BRAF(V600E) | TKL | RAF | 0 |
| BUB1 | Other | BUB | 0 |
| CAMK1 | CAMK | CAMK1 | 0 |
| CDK7 | CMGC | CDK | 0 |
| CDKL2 | CMGC | CDKL | 0 |
| CLK3 | CMGC | CLK | 0 |
| CSF1R | TK | PDGFR | 0 |
| CSNK2A1 | Other | CK2 | 0 |
| DAPK2 | CAMK | DAPK | 0 |
| DRAK2 | CAMK | DAPK | 0 |
| DYRK1B | CMGC | DYRK | 0 |
| DYRK2 | CMGC | DYRK | 0 |
| ERK3 | CMGC | MAPK | 0 |
| FGFR1 | TK | FGFR | 0 |
| GCN2(Kin.Dom.2, S808G) | Other | PEK | 0 |
| GRK4 | AGC | GRK | 0 |
| HIPK2 | CMGC | DYRK | 0 |
| HIPK3 | CMGC | DYRK | 0 |
| JAK1(JH2domain-pseudokinase) | TK | JakA | 0 |
| LOK | STE | STE20 | 0 |
| LTK | TK | Alk | 0 |
| MAP4K3 | STE | STE20 | 0 |
| MAST1 | AGC | MAST | 0 |
| MEK3 | STE | STE7 | 0 |
| MLCK | CAMK | MLCK | 0 |
| MYLK2 | CAMK | MLCK | 0 |
| MYLK4 | CAMK | MLCK | 0 |
| NEK3 | Other | NEK | 0 |
| NEK9 | Other | NEK | 0 |
| PAK4 | STE | STE20 | 0 |
| PHKG2 | CAMK | PHK | 0 |
| PIP5K2B | LIPID | PIP | 0 |
| PRKD3 | AGC | PKC | 0 |
| PRP4 | CMGC | DYRK | 0 |
| SgK110 | Other | NKF1 | 0 |
| SGK3 | AGC | SGK | 0 |
| SRPK1 | CMGC | SRPK | 0 |
| SRPK2 | CMGC | SRPK | 0 |
| SRPK3 | CMGC | SRPK | 0 |
| TIE1 | TK | Tie | 0 |
| TRKB | TK | Trk | 0 |

TABLE 5-continued

Selectivity panel results of Example 11

| Kinase | Specification | Kinase Family | Inhibition (%) |
|---|---|---|---|
| TYK2(JH2domain-pseudokinase) | TK | JakA | 0 |
| ZAK | TKL | MLK | 0 |
| ADCK4 | Atypical | ABC1 | 0 |
| AMPK-alpha1 | CAMK | CAMKL | 0 |
| AMPK-alpha2 | CAMK | CAMKL | 0 |
| ANKK1 | TKL | RIPK | 0 |
| ARK5 | CAMK | CAMKL | 0 |
| BRAF | TKL | RAF | 0 |
| BRSK2 | CAMK | CAMKL | 0 |
| CAMK2A | CAMK | CAMK2 | 0 |
| CAMK2D | CAMK | CAMK2 | 0 |
| CAMKK2 | Other | CAMKK | 0 |
| CDKL1 | CMGC | CDKL | 0 |
| CHEK1 | CAMK | CAMKL | 0 |
| CSNK1G2 | CK1 | CK1 | 0 |
| DCAMKL3 | CAMK | DCAMKL | 0 |
| EGFR | TK | EGFR | 0 |
| EGFR(E746-A750del) | TK | EGFR | 0 |
| EGFR(G719S) | TK | EGFR | 0 |
| EGFR(L747-T751del, Sins) | TK | EGFR | 0 |
| EGFR(L858R) | TK | EGFR | 0 |
| EGFR(L861Q) | TK | EGFR | 0 |
| EPHB4 | TK | Eph | 0 |
| FGFR3(G697C) | TK | FGFR | 0 |
| GSK3A | CMGC | GSK | 0 |
| GSK3B | CMGC | GSK | 0 |
| IKK-alpha | Other | IKK | 0 |
| IKK-beta | Other | IKK | 0 |
| IRAK4 | TKL | IRAK | 0 |
| KIT-autoinhibited | TK | PDGFR | 0 |
| LATS1 | AGC | NDR | 0 |
| LRRK2 | TKL | LRRK | 0 |
| LRRK2(G2019S) | TKL | LRRK | 0 |
| LYN | TK | Src | 0 |
| MAP3K15 | STE | STE11 | 0 |
| MAP3K3 | STE | STE11 | 0 |
| MARK3 | CAMK | CAMKL | 0 |
| MARK4 | CAMK | CAMKL | 0 |
| MEK2 | STE | STE7 | 0 |
| MET(M1250T) | TK | Met | 0 |
| MLK3 | TKL | MLK | 0 |
| MST2 | STE | STE20 | 0 |
| MST4 | STE | STE20 | 0 |
| MUSK | TK | Musk | 0 |
| NDR1 | AGC | NDR | 0 |
| NLK | CMGC | MAPK | 0 |
| PAK6 | STE | STE20 | 0 |
| PCTK1 | CMGC | CDK | 0 |
| PHKG1 | CAMK | PHK | 0 |
| PIK3CA(H1047L) | LIPID | PI3K | 0 |
| PIK4CB | LIPID | PI4K | 0 |
| PIP5K1C | LIPID | PIP | 0 |
| PKN2 | AGC | PKN | 0 |
| PRKD1 | AGC | PKC | 0 |
| ROS1 | TK | Sev | 0 |
| S6K1 | AGC | RSK | 0 |
| SBK1 | Other | NKF1 | 0 |
| STK39 | CAMK | CAMKL | 0 |
| TGFBR2 | TKL | STKR | 0 |
| TNK1 | TK | Ack | 0 |
| TSSK1B | CAMK | TSSK | 0 |
| TYRO3 | TK | Axl | 0 |
| ULK2 | Other | ULK | 0 |
| YSK1 | STE | STE20 | 0 |
| ACVR2A | TKL | STKR | 0 |
| ACVRL1 | TKL | STKR | 0 |
| CAMK1G | CAMK | CAMK1 | 0 |
| CAMK2B | CAMK | CAMK2 | 0 |
| CAMK2G | CAMK | CAMK2 | 0 |
| CAMK4 | CAMK | CAMK1 | 0 |
| CAMKK1 | Other | CAMKK | 0 |
| CDKL3 | CMGC | CDKL | 0 |
| DDR1 | TK | DDR | 0 |
| DLK | TKL | MLK | 0 |
| EPHA6 | TK | Eph | 0 |
| EPHB1 | TK | Eph | 0 |
| ERBB2 | TK | EGFR | 0 |
| ERBB3 | TK | EGFR | 0 |
| ERK4 | CMGC | MAPK | 0 |
| ERN1 | Other | IRE | 0 |
| FGFR4 | TK | FGFR | 0 |
| ICK | CMGC | RCK | 0 |
| INSRR | TK | InaR | 0 |
| JAK1(JH1domain-catalytic) | TK | JakA | 0 |
| LIMK1 | TKL | LISK | 0 |
| LZK | TKL | MLK | 0 |
| MAP4K5 | STE | STE20 | 0 |
| MARK1 | CAMK | CAMKL | 0 |
| MKNK1 | CAMK | MAPKAPK | 0 |
| MLK1 | TKL | MLK | 0 |
| MLK2 | TKL | MLK | 0 |
| MRCKA | AGC | DMPK | 0 |
| MRCKB | AGC | DMPK | 0 |
| MST1 | STE | STE20 | 0 |
| MST1R | TK | Met | 0 |
| NIM1 | CAMK | CAMKL | 0 |
| PAK1 | STE | STE20 | 0 |
| PIK3CA(E542K) | LIPID | PI3K | 0 |
| PIK3CA(E545K) | LIPID | PI3K | 0 |
| PIM3 | CAMK | PIM | 0 |
| PRKCD | AGC | PKC | 0 |
| PRKCE | AGC | PKC | 0 |
| PRKG2 | AGC | PKC | 0 |
| PYK2 | TK | Fak | 0 |
| QSK | CAMK | CAMKL | 0 |
| RPS6KA4(Kin.Dom.1-N-terminal) | AGC | RSK | 0 |
| RPS6KA5(Kin.Dom.1-N-terminal) | AGC | RSK | 0 |
| RSK1(Kin.Dom.1-N-terminal) | AGC | RSK | 0 |
| RSK3(Kin.Dom.2-C-terminal) | AGC | RSK | 0 |
| SNRK | CAMK | CAMKL | 0 |
| STK36 | Other | ULK | 0 |
| TLK2 | Other | TLK | 0 |
| WEE1 | Other | WEE | 0 |
| WEE2 | Other | WEE | 0 |
| WNK3 | Other | Wnk | 0 |
| YANK1 | AGC | YANK | 0 |
| YES | TK | Src | 0 |
| ACVR1B | TKL | STKR | 0 |
| AKT2 | AGC | AKT | 0 |
| ASK2 | STE | STE11 | 0 |
| BMPR1A | TKL | STKR | 0 |
| BTK | TK | Tec | 0 |
| CASK | CAMK | CASK | 0 |
| CDC2L1 | CMGC | CDK | 0 |
| CDK11 | CMGC | CDK | 0 |
| CDK2 | CMGC | CDK | 0 |
| CDK5 | CMGC | CDK | 0 |
| CDK8 | CMGC | CDK | 0 |
| CDK9 | CMGC | CDK | 0 |
| CSK | TK | Csk | 0 |
| DCAMKL2 | CAMK | DCAMKL | 0 |
| EIF2AK1 | Other | PEK | 0 |
| EPHA4 | TK | Eph | 0 |
| EPHA5 | TK | Eph | 0 |
| EPHA7 | TK | Eph | 0 |
| EPHA8 | TK | Eph | 0 |
| EPHB2 | TK | Eph | 0 |
| EPHB3 | TK | Eph | 0 |
| ERBB4 | TK | EGFR | 0 |
| ERK1 | CMGC | MAPK | 0 |
| ERK2 | CMGC | MAPK | 0 |
| FER | TK | Fer | 0 |
| FES | TK | Fer | 0 |
| IGF1R | TK | InsR | 0 |
| MAK | CMGC | RCK | 0 |
| MAP3K4 | STE | STE11 | 0 |
| MAPKAPK2 | CAMK | MAPKAPK | 0 |
| MET | TK | Met | 0 |
| MET(Y1235D) | TK | Met | 0 |
| MTOR | Atypical | PIKK | 0 |

TABLE 5-continued

Selectivity panel results of Example 11

| Kinase | Specification | Kinase Family | Inhibition (%) |
|---|---|---|---|
| MYO3A | STE | STE20 | 0 |
| MYO3B | STE | STE20 | 0 |
| NEK11 | Other | NEK | 0 |
| NEK7 | Other | NEK | 0 |
| p38-alpha | CMGC | MAPK | 0 |
| p38-beta | CMGC | MAPK | 0 |
| PCTK3 | CMGC | CDK | 0 |
| PFPK5(*P. falciparum*) | Pathogen | *P. Falciparum* | 0 |
| PFTAIRE2 | CMGC | CDK | 0 |
| PIK3CB | LIPID | PI3K | 0 |
| PKMYT1 | Other | WEE | 0 |
| PLK1 | Other | PLK | 0 |
| PRKCH | AGC | PKC | 0 |
| PRKCI | AGC | PKC | 0 |
| PRKX | AGC | PKA | 0 |
| RAF1 | TKL | RAF | 0 |
| RSK2(Kin.Dom.2-C-terminal) | AGC | RSK | 0 |
| TEC | TK | Tec | 0 |
| TESK1 | TKL | LISK | 0 |
| TGFBR1 | TKL | STKR | 0 |
| TIE2 | TK | Tie | 0 |
| TNK2 | TK | Ack | 0 |
| TRPM6 | Atypical | Alpha | 0 |
| TXK | TK | Tec | 0 |
| WNK1 | Other | Wnk | 0 |
| YANK2 | AGC | YANK | 0 |
| YANK3 | AGC | YANK | 0 |

Based on our measurements and the scientific literature we conclude that the presented styryl quinazoline derivatives are candidates for further development of signal transduction cancer therapy, especially for AML patients. The compounds are highly selective for FLT3 mutations, they have a considerably good $IC_{50}$ values in in vitro FLT3(ITD) biochemical assay and in MV11-4 cell viability assay. Together with the known effect of styryl quinazolines on P53 tumor suppressor protein the data presented shows that they are potent candidates to develop a selective and sophistically targeted therapy in case of FLT3(ITD) and other FLT3 mutations which is fairly common among leukemia patients.

Determination of Antibacterial Activity
Minimal Inhibitory Concentration (MIC)

The European Committee for Antimicrobial Susceptibility Testing (EUCAST) defines the Minimal Inhibitory Concentration (MIC) as the lowest concentration of an antibiotic that inhibits the growth of a bacterial inoculum, under defined in vitro conditions. The MICs were determined for *Escherichia coli* strains LMC500 (F, araD139, D(argF-lac) U169deoC1, flbB5301, ptsF25, rbsR, relA1, rpsIL150, lysA1) and BW25113 (F, DE(araD-araB)567, lacZ4787 (del):rmB-3, LAM, rph-1, DE(rhaD-rhaB)568, hsdR514 ΔAcrA ΔAcrB ΔtolC). The former stain is a wild type *E. coli* K12 strain and the latter strain modified in such a way that it cannot produce the TolC multidrug efflux pump. Therefore, it is expected to be more susceptible to inhibitors that may be otherwise ignored. The defined medium used was tryptone yeast-extract (TY)-medium composed of 10 g/l Tryptone (Bacto), 5 g/l yeast extract (Bacto) and 5 g/l NaCl.

The compounds were diluted to stock solutions of 1024 µg/ml in MilliQ ultrafiltrated distilled water (hereinafter MilliQ) and in DMSO and in a varying composition mixture of MilliQ and DMSO. Solubility was tested by visual inspection and poorly dissolving compounds were dissolved in higher concentrations of DMSO in the mixture but not higher than 50% to prevent adverse effects on bacterial growth by the suspension form it self. For the MIC test first the compounds were diluted to 256 µg/ml in MilliQ and two-fold serial dilutions in MilliQ were prepared from well A to D or E to H in a 96-well plate with an end volume of 75 µl. The inoculum was prepared by suspending a logarithmically growing bacterial culture in 2×TY medium to match an optical density at 600 nm wavelength ($OD^{600}$) of 0.001 (cuvettes 1 cm in diameter, VWR) using a spectrophotometer (Biochrom Libra S22). Seventy-five µl of this suspension was then added to the wells, resulting in antibiotic end concentrations ranging from 128 to 16 µg/ml in wells A to D and E to H. Groups without antibiotics but with comparable DMSO concentrations or groups without bacteria served as positive and negative controls, respectively. The 96-wells plates were incubated overnight at 37° C. and were shaken the platereader (SYNERGY BIOTEK) during which the $OD^{600}$ values were measured every 10 min. The next day the growth data were analysed and MIC values were determined. The inoculum was quantified by plating 10-fold serial dilutions in PBS ($10^{-2}$ to $10^{-7}$) on TY agar plates, which were incubated overnight at 37° C. The next day the colonies were counted and the CFU/well values were calculated. All MIC experiments were performed in duplicates. For those compounds that showed a MIC of less than 16 µg/ml, the assay was repeated with antibiotic end concentrations of 128 to 0.125 µg/ml.

Minimal Bactericidal Concentration (MBC)

The minimal bactericidal concentration (MBC) is defined as the lowest concentration of an antibiotic that, under defined in vitro conditions reduces the number of bacteria by 99.9%. All MIC experiments with compounds exhibiting growth reduction were chosen for MBC testing. MBC tests were performed by plating 10 µl of a finished liquid MIC test from the 96 well plate on TY agar. The plates were then incubated overnight at 37° C. The next day the MBC was determined as the lowest concentration at which less than 10 colonies grew (>99.99% reduction of the inoculum). All MBC experiments were performed in duplicates.

| | ΔAcrAB TolC | | LMC500 | | *Bacillus subtilis* 168 |
|---|---|---|---|---|---|
| Example | MIC (µg/ml) | MBC (µg/ml) | MIC (µg/ml) | MBC (µg/ml) | MIC (µg/ml) |
| 1 | 8 | 8 | 32 | 32 | 8 |
| 3 | 32 | 64 | >128 | ND | ND |
| 7 | 8 | 8 | 32 | 32 | 8 |
| 20 | 8 | 8 | <16 | <16 | 4 |
| 23 | 32/64 | 32 | >128 | ND | ND |
| 78 | 32 | <16 | 64 | >128 | ND |
| 99 | 32 | <16 | 64 | 64 | ND |
| 109 | <16 | <16 | 64 | 64 | ND |
| 112 | 8 | 8 | 32 | >128 | 8 |

The invention claimed is:
1. A compound of general formula (I) and pharmaceutically acceptable salts, solvates, hydrates, regioisomeric and polymorphic forms thereof,

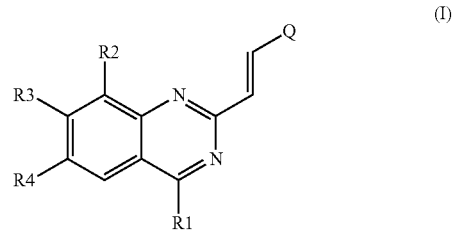

(I)

wherein
R1 is 1-dimethylamino-propane-3-ylamino, 1-diethyl-amino-propane-3-ylamino, 3-(morpholin-4-yl)propyl-amino, 3-(4-methylpiperazin-1-yl)propylamino, 1-dim-ethylamino-2-ethylamino, 1-dimethylamino-2-ethylamino, 1-diethylamino-pentane-4-yl-amino, 1-(tertbutylcarbamate)-propane-3-yl-amino, 1-amino-propane-3-yl-amino, 1-acetylamino-propane-3-yl-amino, 1-(piperidin-4-one-ethylenketal), 2-(pyrrolidin-1-ylmethyl)pyrrolidin-1-yl, propane-3-yl-amino;

R2 is hydrogen or bromine;

R3 is hydrogen, chlorine, nitro or methoxy and R4 is hydrogen, fluorine, chlorine, bromine or methoxy; or R3 and R4 together with the carbon atoms they are attached to may form an aryl fused to the quinazoline ring; and Q is 4-methoxy-phenyl, 3-fluoro-phenyl, 4-fluoro-phenyl, 4-chloro-phenyl, 4-(dimethylamino)phenyl, 3,4,5-trimethoxyphenyl, 3,4-difluorophenyl, 4-(methylthio)phenyl, 2-thienyl, 4-isopropylphenyl or 4-(methylsulfonyl)phenyl.

2. A method for the treatment of a disease related to dysfunction of hematopoiesis and/or a cancerous, neoplastic or hyperplastic disease, wherein the dysfunction of hematopoiesis and the cancerous, neoplastic or hyperplastic disease are related to the Fms-like tyrosine kinase 3 (FLT3) containing Internal Tandem Duplications (ITD) or other FLT3 mutation, said method comprising administering a compound of general formula (I) or a pharmaceutically acceptable salt, solvate, hydrate, or regioisomeric or polymorphic form thereof, to an individual in need thereof

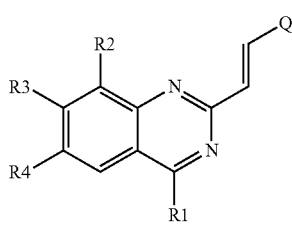

(I)

wherein
R1 is 1-dimethylamino-propane-3-ylamino, 1-diethyl-amino-propane-3-ylamino, 3-(morpholin-4-yl)propyl-amino, 3-(4-methylpiperazin-1-yl)propylamino, 1-dim-ethylamino-2-ethylamino, 1-dimethylamino-2-ethylamino, 1-diethylamino-pentane-4-yl-amino, 1-(tertbutylcarbamate)-propane-3-yl-amino, 1-amino-propane-3-yl-amino, 1-acetylamino-propane-3-yl-amino, 1-(piperidin-4-one-ethylenketal), 2-(pyrrolidin-1-ylmethyl)pyrrolidin-1-yl, propane-3-yl-amino;

R2 is hydrogen or bromine;

R3 is hydrogen, chlorine, nitro or methoxy and R4 is hydrogen, fluorine, chlorine, bromine or methoxy; or R3 and R4 together with the carbon atoms they are attached to may form an aryl fused to the quinazoline ring; and Q is 4-methoxy-phenyl, 3-fluoro-phenyl, 4-fluoro-phenyl, 4-chloro-phenyl, 4-(dimethylamino)phenyl, 3,4,5-trimethoxyphenyl, 3,4-difluorophenyl, 4-(methylthio)phenyl, 2-thienyl, 4-isopropylphenyl or 4-(methylsulfonyl)phenyl.

3. The method of claim 2 wherein the dysfunction of hematopoiesis and cancerous, neoplastic or hyperplastic disease depend on the Fms-like tyrosine kinase 3 (FLT3) containing Internal Tandem Duplications (ITD).

4. The method of claim 2, wherein R3 is hydrogen, chlorine, nitro or methoxy and R4 is hydrogen, fluorine, chlorine, bromine or methoxy.

5. The method of claim 2, wherein
R3 and R4 together with the carbon atoms they attached to may form an aryl fused to the quinazoline ring.

6. A method for the treatment of a disease related to dysfunction of hematopoiesis and/or a cancerous, neoplastic or hyperplastic disease, said method comprising administering a compound of general formula (I) or a pharmaceutically acceptable salt, solvate, hydrate, or regioisomeric or polymorphic form thereof, to an individual in need thereof

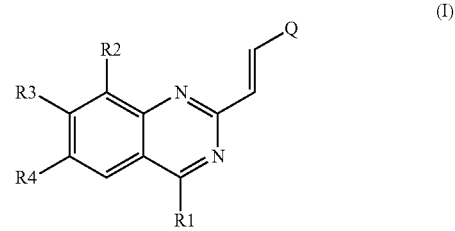

(I)

wherein
R1 is 1-dimethylamino-propane-3-ylamino, 1-diethyl-amino-propane-3-ylamino, 3-(morpholin-4-yl)propyl-amino, 3-(4-methylpiperazin-1-yl)propylamino, 1-dim-ethylamino-2-ethylamino, 1-dimethylamino-2-ethylamino, 1-diethylamino-pentane-4-yl-amino, 1-(tertbutylcarbamate)-propane-3-yl-amino, 1-amino-propane-3-yl-amino, 1-acetylamino-propane-3-yl-amino, 1-(piperidin-4-one-ethylenketal), 2-(pyrrolidin-1-ylmethyl)pyrrolidin-1-yl, propane-3-yl-amino;

R2 is hydrogen or bromine, R3 is hydrogen, chlorine, nitro or methoxy and R4 is hydrogen, fluorine, chlorine, bromine or methoxy; or R3 and R4 together with the carbon atoms they attached to may form an aryl fused to the quinazoline ring;

Q is 4-methoxy-phenyl, 3-fluoro-phenyl, 4-fluoro-phenyl, 4-chloro-phenyl, 4-(dimethylamino)phenyl, 3,4,5-trimethoxyphenyl, 3,4-difluorophenyl, 4-(methylthio)phenyl, 2-thienyl, 4-isopropylphenyl or 4-(methylsulfonyl)phenyl.

7. The method of claim 2, said method comprising administering a pharmaceutical composition to the individual, said pharmaceutical composition containing as active ingredient one or more compound(s) of general formula (I) according to claim 2 together with one or more usual pharmaceutical auxiliary material(s).

8. The method of claim 6 wherein the dysfunction of hematopoiesis and the cancerous, neoplastic or hyperplastic disease depend on the Fms-like tyrosine kinase 3 (FLT3) containing Internal Tandem Duplications (ITD).

9. The method of claim 6 for the treatment of a cancerous, neoplastic or hyperplastic disease related to dysfunction of hematopoiesis.

10. The method of claim 6 for the treatment of myeloid leukemia.

11. The method of claim 6, wherein R3 is hydrogen, chlorine, nitro or methoxy and R4 is hydrogen, fluorine, chlorine, bromine or methoxy.

12. The method of claim 6, wherein R3 and R4 together with the carbon atoms they attached to may form an aryl fused to the quinazoline ring.

* * * * *